(12) United States Patent
Douglas et al.

(10) Patent No.: US 11,207,133 B1
(45) Date of Patent: *Dec. 28, 2021

(54) METHOD AND APPARATUS FOR THE INTERACTION OF VIRTUAL TOOLS AND GEO-REGISTERED TOOLS

(71) Applicants: David Byron Douglas, Winter Park, FL (US); Robert Edwin Douglas, Winter Park, FL (US); Kathleen Mary Douglas, Winter Park, FL (US)

(72) Inventors: David Byron Douglas, Winter Park, FL (US); Robert Edwin Douglas, Winter Park, FL (US); Kathleen Mary Douglas, Winter Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,985

(22) Filed: Sep. 9, 2019

Related U.S. Application Data

(60) Provisional application No. 62/728,934, filed on Sep. 10, 2018.

(51) Int. Cl.
| | |
|---|---|
| *A61B 34/10* | (2016.01) |
| *G06F 3/0484* | (2013.01) |
| *G06T 19/20* | (2011.01) |
| *G06F 3/01* | (2006.01) |
| *A61B 34/00* | (2016.01) |
| *G06T 15/08* | (2011.01) |

(52) U.S. Cl.
CPC ............. *A61B 34/10* (2016.02); *A61B 34/25* (2016.02); *G06F 3/013* (2013.01); *G06F 3/04842* (2013.01); *G06F 3/04845* (2013.01); *G06T 15/08* (2013.01); *G06T 19/20* (2013.01); *A61B 2034/102* (2016.02); *A61B 2034/105* (2016.02); *G06T 2210/41* (2013.01)

(58) Field of Classification Search
None
See application file for complete search history.

(56) References Cited

U.S. PATENT DOCUMENTS

| | | | |
|---|---|---|---|
| 8,349,183 | B2 | 1/2013 | Field |
| 8,384,771 | B1 | 2/2013 | Douglas |
| 9,473,766 | B2 | 10/2016 | Douglas |
| 9,980,691 | B2 | 5/2018 | Douglas |

(Continued)

FOREIGN PATENT DOCUMENTS

WO  WO-2020041693 A1 * 2/2020 ............ G16H 30/40

OTHER PUBLICATIONS

Brandon Yee, Yuan Ning, Hod Lipson, "Augmented Reality In-Situ 3D Sketching of Physical Objects," 2009, CHI 2009 (Year: 2009).*

(Continued)

*Primary Examiner* — Michael J Cobb

(57) ABSTRACT

Virtual objects can be affixed to geo-registered tools (e.g., platform, knife, etc.) that interact with items (e.g., anatomic structures) within 3D volumes. For example, a 27-foot virtual wand can be affixed to a 1-foot long geo-registered wand and the resulting multi-part wand can be moved another two feet within a 3D volume in response to movement of the geo-registered wand to reach an object 30 feet away in the 3D volume. Various other interaction techniques are disclosed. The techniques may be used in a variety of applications possibly including, but not limited to, medicine, gaming, education, carpentry, manufacturing, or other industries.

28 Claims, 44 Drawing Sheets

(56) References Cited

U.S. PATENT DOCUMENTS

| | | | |
|---|---|---|---|
| 10,586,400 B2 | 3/2020 | Douglas | |
| 10,671,241 B1* | 6/2020 | Jia | G09G 5/37 |
| 10,795,457 B2 | 10/2020 | Douglas | |
| 2010/0305928 A1* | 12/2010 | Cohen | G06F 19/321 |
| | | | 703/11 |
| 2011/0144658 A1* | 6/2011 | Wenderow | A61B 34/30 |
| | | | 606/130 |
| 2013/0065211 A1* | 3/2013 | Amso | G09B 23/286 |
| | | | 434/262 |
| 2019/0247121 A1 | 8/2019 | Douglas | |
| 2019/0251755 A1 | 8/2019 | Douglas | |
| 2019/0311542 A1 | 10/2019 | Douglas | |

OTHER PUBLICATIONS

Julian Looser, Raphael Grasset, Mark Billinghurst, "A 3D Flexible and Tangible Magic Lens in Augmented Reality" 2007, 2007 6th IEEE and ACM International Symposium on Mixed and Augmented Reality, DOI: 10.1109/ISMAR.2007.4538825 (Year: 2007).*

John Viega, Matthew J. Conway, George Williams, Randy Pausch, "3D Magic Lenses," 1996, UIST '96 Proceedings of the 9th Annual ACM Symposium on User Interface Software and Technology, https://doi.org/10.1145/237091.237098 (Year: 1996).*

Christopher Andrews, Michael K. Southworth, Jennifer N. A. Silva, Jonathan R. Silva, "Extended Reality in Medical Practice," 2019, Current Treatment Options in Cardiovascular Medicine, 21:18, pp. 1-12, DOI 10.1007/s11936-019-0722-7 (Year: 2019).*

Leonard D. Brown, Hong Hua, "Magic Lenses for Augmented Virtual Environments," 2006, IEEE Computer Graphics and Applications, 26(4):July-Aug. 2006, DOI: 10.1109/MCG.2006.84 (Year: 2006).*

\* cited by examiner

OVERVIEW OF THE APPARATUS

EXAMPLE USE OF A VIRTUAL POINTER TO POINT TO KNOWLEDGE SPOTS ON VIRTUAL BODY STRUCTURE TO RETRIEVE MEDICAL TERMINOLOGY AND BODILY FUNCTIONS

EXAMPLE USE OF A VIRTUAL KNIFE, WHICH CAN BE USED BY PERSONS PLAYING THE GAME TO 'CARVE AWAY TISSUE' FROM AN EXISTING 3D MEDICAL IMAGE TO PERMIT ENHANCED VIEWING OF THE INTERIOR STRUCTURE

ILLUSTRATION OF A VIRTUAL RIDE THROUGH A VIRTUAL VASCULAR TUNNEL WITH ROAD SIGN FOR A PERSON PLAYING THE GAME USING A VISUAL TRANSPORT TOOL.
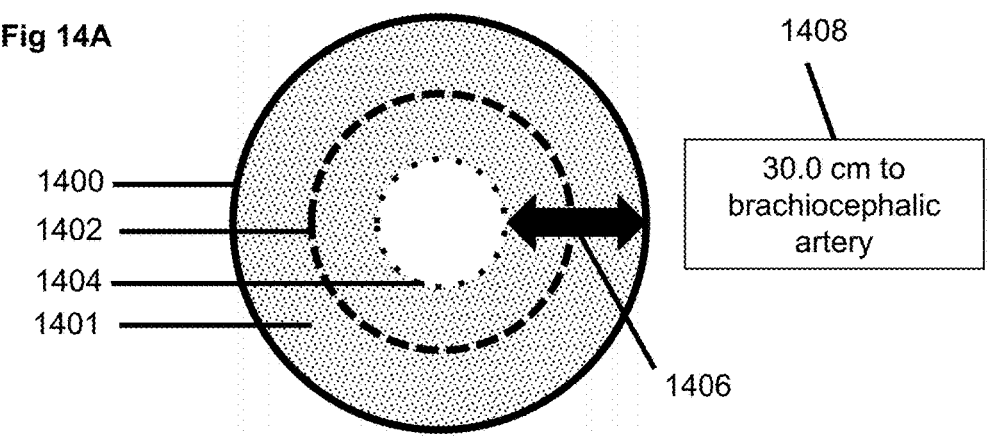
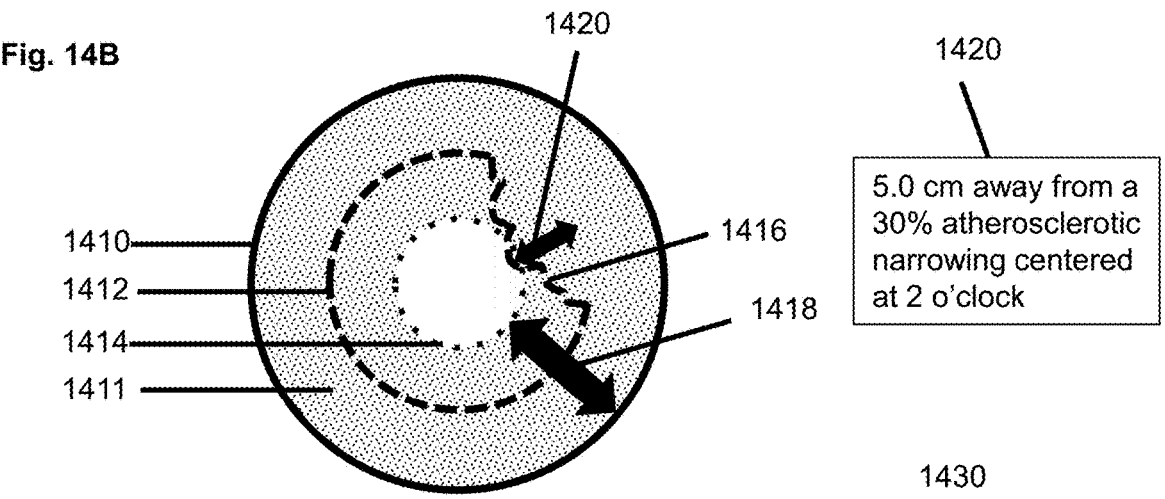
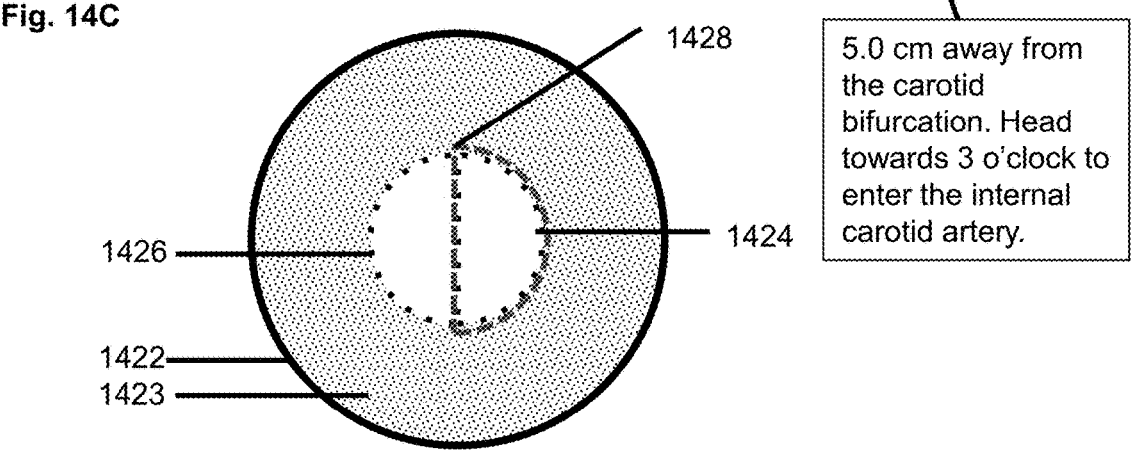

ILLUSTRATION OF A VIRTUAL CATHETER EXAMPLE, WHICH COULD BE USED IN CONJUNCTION WITH A VOLUMETRIC MEDICAL IMAGE OF THE VASCULAR STRUCTURE WITHIN THE PATIENT WITH THE ASSISTANCE OF VIRTUAL ICONS
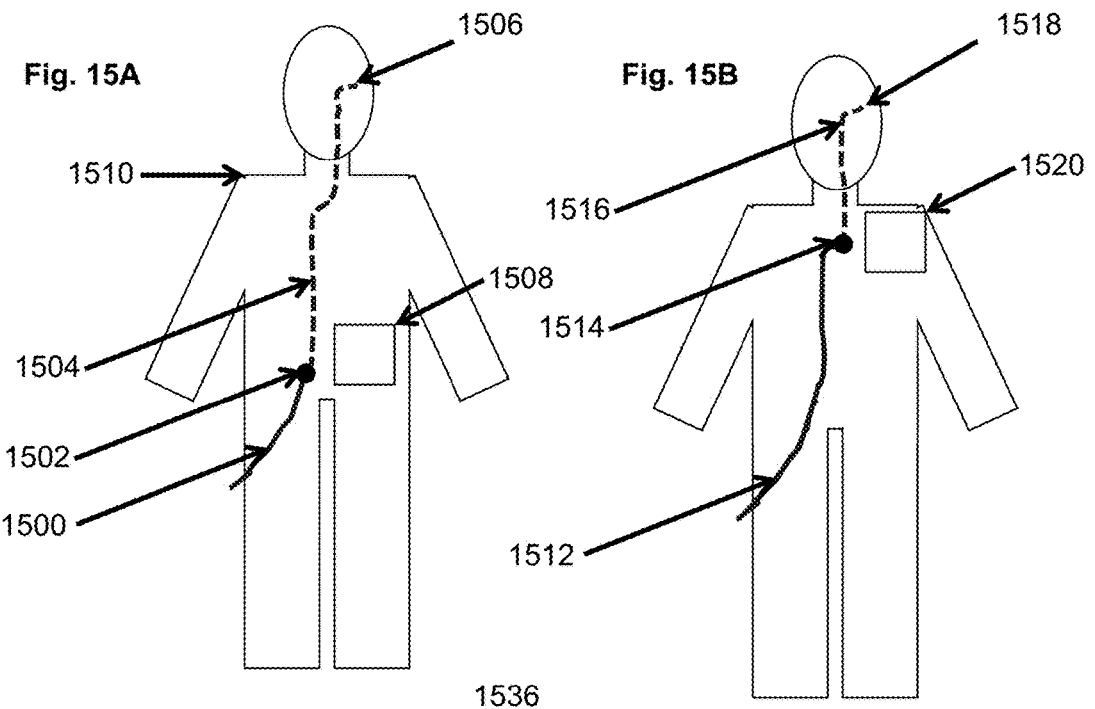
Fig. 15A
Fig. 15B
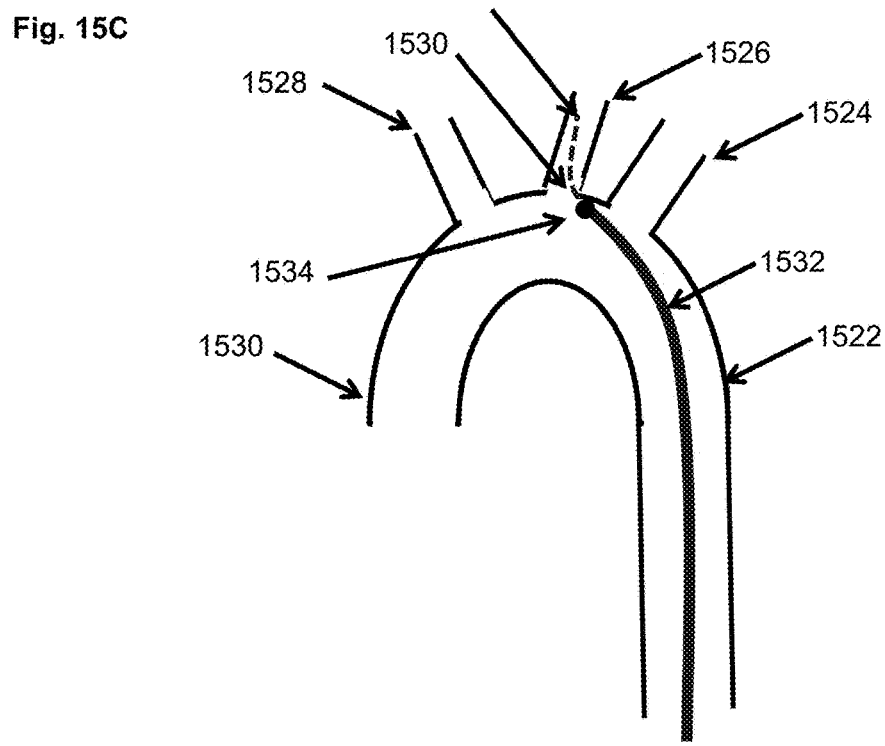
Fig. 15C ILLUSTRATES THE GENERAL CONCEPT OF 3D MEDICAL IMAGES AND EXAMPLE TECHNIQUES BEHIND THE EXPLOSION OF 3D MEDICAL IMAGES INTO MULTI SEPARATE ORGANS WHICH CAN THEN BE INDIVIDUALLY SELECTED BY PERSON PLAYING THE GAME
Fig. 16A
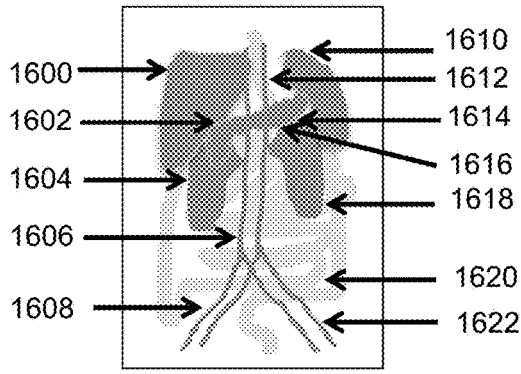
Fig. 16D
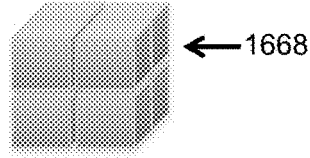
Fig. 16B
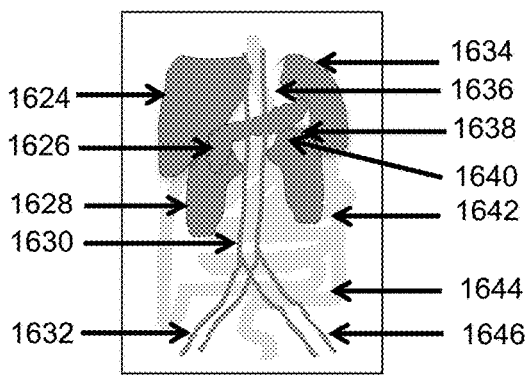
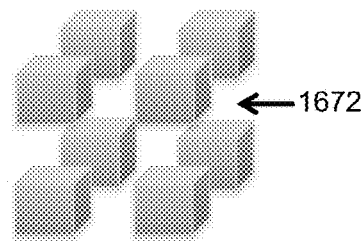
Fig. 16C
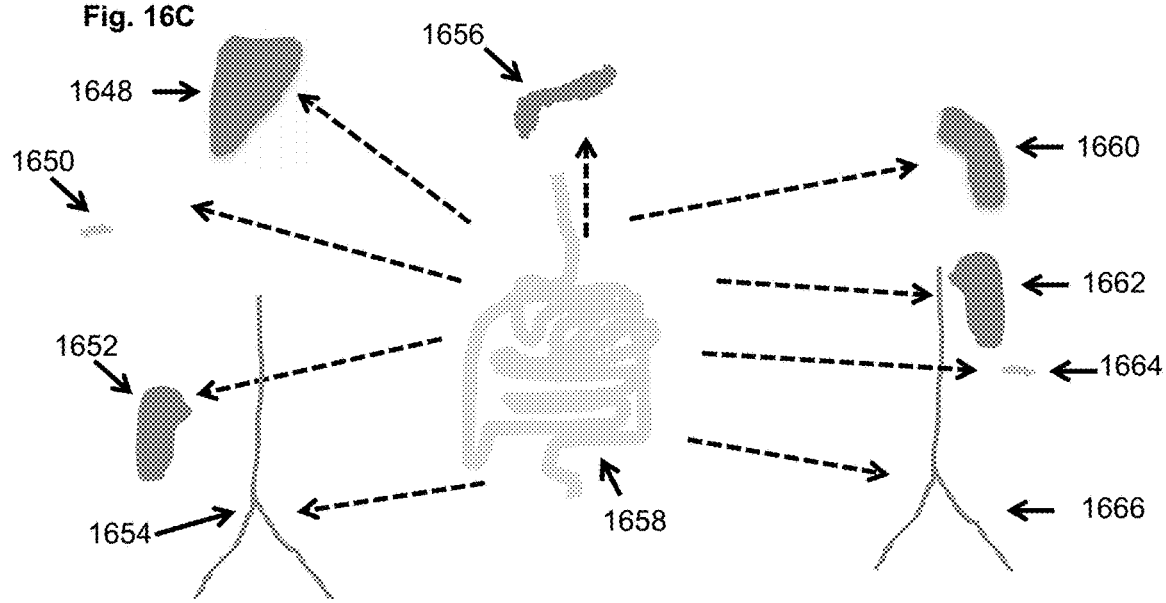

ILLUSTRATES USE OF VIRTUAL TRANSPORT VIEWER TO PERFORM A VIRTUAL COLONOSCOPY.

ILLUSTRATES AN ICON OF A HUMAN WITH THE LOCATION OF THE 3D VIRTUAL CURSOR SHOWING THE APPROXIMATE LOCATION WITHIN THE BODY

ILLUSTRATES A VIRTUAL MOVABLE TABLE FOR STORING VIRTUAL
IMAGES OF SUSPECT TISSUE STORED BY CHECKLIST CATEGORY

GEO-REGISTERED HEAD DISPLAY UNIT
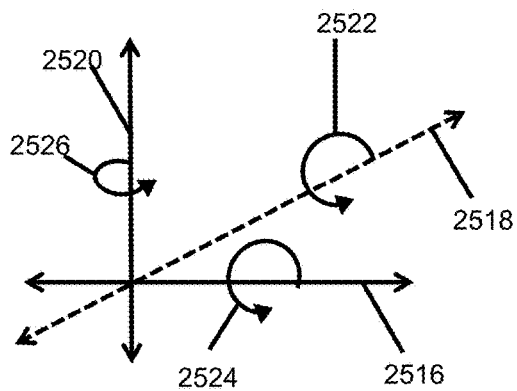
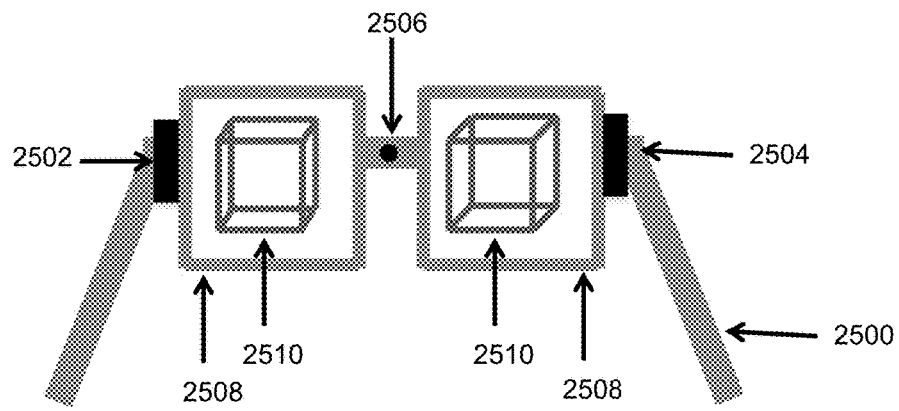
| Tangible Item | Key Design Element | Key Functions |
|---|---|---|
| Head Display Unit | Position tracking (XYZ), orientation tracking (RPY) | Provides stereoscopic vision, optimization of pixels/degree FOV based on convergence, looking direction and item of interest |
Figure 25

GEO-REGISTERED FOCAL POINT PEN

| Tangible Item | Key Design Element | Key Functions |
|---|---|---|
| Focal point pen | Position tracking (XYZ), orientation tracking (RPY) | Provides enhanced viewing (e.g., guides focal point convergence, smooth tracking). Provides ability to select tissues of interest (e.g., select blood vessels to be separated). Provides annotations. |

VIRTUAL ABLATION

GEO-REGISTERED HAND-HELD PLATFORM
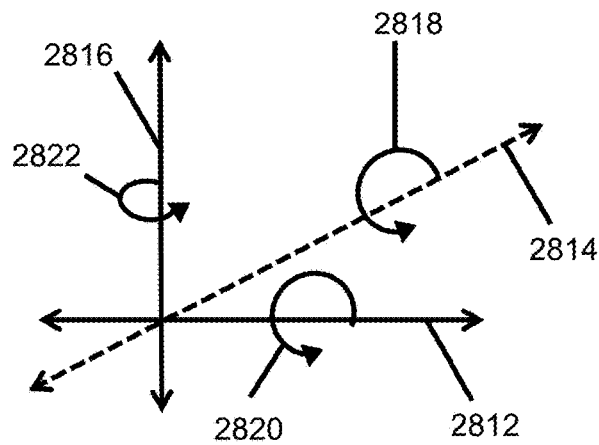
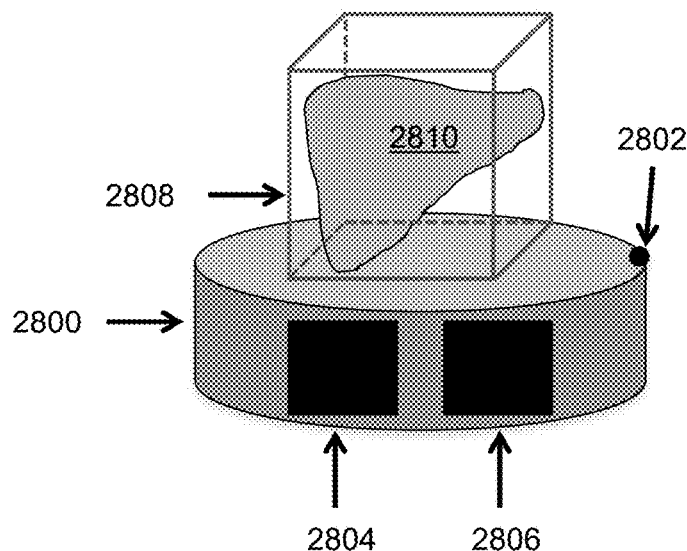
| Tangible Item | Key Design Element | Key Functions |
|---|---|---|
| Hand held platform | Position tracking (XYZ), orientation tracking (RPY) | Provides ability to fix a virtual structure to the tangible real-world object for rotate/translate whole or sub-volume in palm of hand (e.g., holding heart in one's hand) |
Figure 28

VISUAL MARKERS TO INDICATE VIEWING PARAMETERS

LEFT EYE GAZE DIRECTION VISUAL INDICATOR, RIGHT EYE GAZE DIRECTION VISUAL INDICATOR, CONVERGENCE AND CENTER LINE OF FOCUS

| Tangible Item | Key Design Element | Key Functions |
|---|---|---|
| Catheter device | Position tracking (XYZ), orientation tracking (RPY) | Provides ability to maneuver a catheter through a hollow structure in the body, such as an artery. |

VIRTUAL DASHBOARD, MANAGEMENT BOARD AND ICON
Fig. 42A
| Demographics | Prior History |
|---|---|
| • Age: 52 years<br>• Weight: 185 lbs<br>• Married | • Fractured tibia in 2009<br>• Pneumonia in 2012 |
| Current complaint | Vitals |
| • Chest pain | •Blood pressure: 140/92 mmHg<br>•Heart Rate: 85 beats/min<br>•Temperature: 99.5 ° F |
Fig. 42B
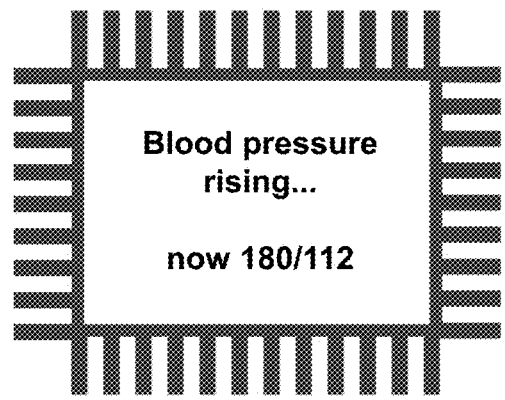
Fig. 42C
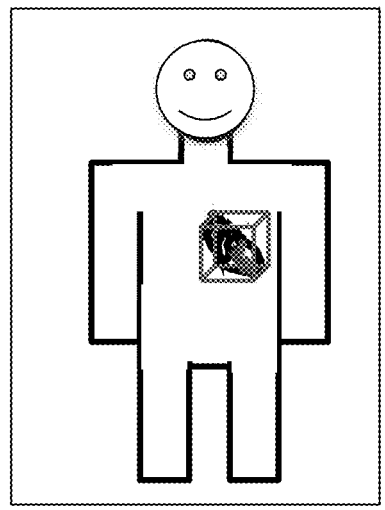

ILLUSTRATION OF COMPETITIVE GAME STRUCTURE AND
EXAMPLE SCORING PROCESS IN ANATOMY TYPE GAME AND
INVESTIGATIVE TYPE GAME

Fig. 43A

| PLAYER 1 |
|---|
| Level 1 - 10/10<br>Level 2 - 4/14<br>Level 3 - 2/28 |
| Total time - 1:32 |
| Total score - 32 points |

| PLAYER 2 |
|---|
| Level 1 - 9/10<br>Level 2 - 5/14<br>Level 3 - 2/28 |
| Total time - 1:32 |
| Total score - 1:32 |

Fig. 43B

| PLAYER 1 |
|---|
| Stage 1 - 1/5<br>Stage 2 - 2/7<br>Stage 3 - 6/8<br>Stage 4 - 10/10<br>Metastases - 4/20 |
| Total time – 3:12 |
| Total score – 34 points |

| PLAYER 2 |
|---|
| Stage 1 - 2/5<br>Stage 2 - 3/7<br>Stage 3 - 5/8<br>Stage 4 - 9/10<br>Metastases - 6/20 |
| Total time – 4:01 |
| Total score – 29 points |

| Game type | Learning objective | Example scenarios and special features |
|---|---|---|
| Virtual Anatomy | Basic understanding of normal anatomy | Head-to-toe anatomy; e.g.,, player is shown anatomical term (e.g., scaphoid) and must rapidly selecting anatomy using a pointer device |
| Jig Saw Puzzle | Learn detailed 3D anatomy geometry | Anatomical structures are separated into multiple parts (e.g., bones of the wrist) and must properly arrange them |
| Hands-on Anatomy | Comprehensive understanding of normal anatomy | Go to heart, encapsulate 3D cursor, run segmentation such that tissue external to the heart is subtracted, transport the heart via the VR 3D cursor and affix it to a geo-registered hand held platform; use geo-registered pen to point to different parts of the heart and verify the names; use geo-registered knife and carve away a portion of the left ventricle wall and look inside at the valves. |
| Moving body(4D) | Comprehensive understanding of normal mobile anatomy | Watch 3D images move over time (i.e., 4D imaging), such as heart valves opening and closing, blood flow through blood vessels; muscles contract during exercise; flash of light and signal travels to visual cortex, etc. |
| Virtual Pathology | Comprehensive understanding of pathology | Watch 4D image of the heart coupled with the heart murmur sound from a particular pathological condition (e.g., aortic regurgitation and Austin Flint murmur). May be performed with virtual tool kit (e.g., virtual stethoscope) or tangible geo-registered stethoscope. |
| Surgery | Introduction to steps required to perform a variety of surgeries | Use geo-registered tangible surgical instruments (e.g., scalpel), and intangible virtual tools (e.g., retractors, sutures) and advice given by virtual guru to complete a variety of surgeries, such as breast lumpectomy or appendectomy. |
| Interventional Radiology | Introduction to steps required to perform a variety of interventional procedures | Use geo-registered tangible surgical instruments (e.g., catheter), virtual tools (e.g., virtual contrast, virtual coil) and advice given by virtual guru to complete a variety of interventional procedures, such as brain aneurysm coiling, coronary artery stenting, chemoembolization of hypervascular liver metastases. |
| Emergency Medicine | Introduction to imminently life-threatening conditions and treatment thereof | Use geo-registered tangible surgical instruments (e.g., scalpel, central line) and virtual tools (e.g., chest tube, tracheostomy tube) to perform immediate life saving procedures for conditions such as gunshot wounds, motor vehicle accidents, pneumothorax, etc. |
| Investigation | Introduction to detecting cancer | Use actual patient imaging data with known cancers and must sift through the tissues and find the cancer. |

Figure 44

METHOD AND APPARATUS FOR THE INTERACTION OF VIRTUAL TOOLS AND GEO-REGISTERED TOOLS

TECHNICAL FIELD

This patent is related to interaction of geo-registered tools and virtual objects.

BACKGROUND

The field of augmented reality is growing and has applications in medicine, video games and other areas of industry. Within the field of medicine, it is anticipated that diagnostic radiology will benefit greatly from augmented reality due to the ability to achieve true 3D stereoscopic imaging (See U.S. Pat. No. 8,384,771), focal point convergence (See U.S. Pat. No. 9,349,183), 3D cursor usage (See U.S. Pat. No. 9,980,691) and an immersive fly-through environment. Recent patent application submissions have enabled advanced filtering and segmentation algorithms (See U.S. application Ser. No. 15/904,092), the use of geo-registered tools (See U.S. application Ser. No. 16/524,275) and virtual tools (See PCT/US19/47891).

SUMMARY

The present disclosure describes enhanced interaction of virtual tools with geo-registered tools. The inventive concepts may have applicability in medicine, videogames and other technological fields, for example, and without limitation. Regarding medicine, it is projected that there will be a major shortage of doctors within the US in the not-too-distant future. Inspiring young persons to enter the medical field will help ameliorate this shortage. In this disclosure we present a method and apparatus for using real patient anatomy and body structure in a gaming environment, yielding a fun interactive experience with acquisition of medical knowledge as a byproduct.

In some implementations, a three-dimensional image volume will be loaded into an image processing system, items within the three-dimensional image volume will be assigned an interactive feature and items within the three-dimensional image volume are manipulated based on inputs from a geo-registered tool. Items within the three-dimensional image volume include, but are not limited to, the following: a single voxel; a group of voxels; a two-dimensional slice (planar or non-planar); multiple two-dimensional slices arranged together to generate a volume; a three-dimensional cursor; a three-dimensional structure (e.g., tangible object such as a chair, non-tangible object such as air); a medical structure corresponding to a patient scan or a simulated patient image. Items can be programmed for interaction capabilities. For example, an item (e.g., liver) can be isolated via segmentation algorithms and then programmed with interactive capabilities (e.g., when liver is touched with geo-registered tool, an information box appears). Virtual tools can be used as well. For example, if a virtual object (e.g., ball) is a long distance away (e.g., 30 feet), then a 1-foot geo-registered tool (e.g. wand) can be held outward on an outstretched 2-foot long arm two feet and then connected to a 27-foot virtual wand and then the distance object is touched. Thus, the geo-registered object can be affixed to a virtual object and the two interact with a 3D volume. A voxel is a 3D pixel equivalent, which has length, width and height. For example, a single CT scan slice with a matrix of 512 pixels×512 pixels would have 262,144 voxels. An interactive feature of an item includes the capability to change based on input and include, but are not limited to the following: change in position, orientation, size, shape, color, texture, medical imaging type image alterations (e.g., windowing and leveling, segmentation, filtering, altering left eye viewing point, altering right eye viewing point, altering left eye viewing angle, altering right eye viewing angle, altering the volume of interest as a whole such as zooming, rotation, convergence, false color, explosion views, virtual dissection, etc.), metrics related to interaction with geo-registered tool (e.g., counting the number of times a target is hit, etc.), virtual question and answer or any other alteration from the initial status. A geo-registered tool comprises a tangible object. Geo-registered tools position can be determined by external video cameras or through equipped with an inertial measurement unit, battery, send/receive element, registration points, and registration process, as described in greater detail below. Inputs from a geo-registered tool may include, but are not limited to the following, movement to a particular position (with respect to the three-dimensional image volume), change in orientation (with respect to the three-dimensional imaging volume), or activating the geo-registered tool (e.g., user presses a button).

In some embodiments, 3D images would be constructed from medical images taken of actual person's anatomies and used in computer video games to engender interest in the medical profession. The data could include actual DICOM patient images which have been anonymized (e.g., CT scans, MRI scans, PET scans, SPECT scans, etc.), actual patient photographs of anatomy, actual patient vitals, actual patient laboratory reports, actual patient pathology reports, actual patient surgical reports, actual patient histories, actual patient physical examinations. Totality of imaging options would include: construction and display of 3D medical images and manipulation thereof with rotation, zooming, false color, fly through, etc. (See U.S. Pat. No. 8,384,771); focal point convergence (See U.S. Pat. No. 9,349,183); use of alternative displays (See U.S. Pat. No. 9,473,766); introduction of a 3D cursor (See U.S. Pat. No. 9,980,691); additional 3D cursor implementations (See U.S. patent application Ser. No. 15/878,463); filtering and segmentation techniques (See U.S. patent application Ser. No. 15/904,092); surgical applications (See U.S. patent application Ser. No. 15/949,202); insertion of virtual medical devices in a virtual patient structure (See U.S. patent application Ser. No. 16/010,925); voxel manipulation (See U.S. patent application Ser. No. 16/195,251); geo-registration of tools to assist with examination of medical images (See U.S. patent application Ser. No. 16/524,275); virtual tool kit including pedestal, pen, travel in blood vessels, exploded view, etc. (See PCT/US19/47891).

In some implementations, the system would comprises tangible components such as: display element (e.g., virtual reality (VR) or augmented reality (AR) or mixed reality (MR) headset; computer monitor with 3D projection; high resolution 3D TV and associated glasses); control element (e.g., joystick, game controller, mouse, or keyboard); processor unit; supporting equipment (e.g., cables, power supply, etc.).

In some implementations, real patient medical images/data would be used to create a virtual 3D medical image of the real patient's body structure. The virtual 3-D real person body structure can be used in conjunction with virtual tools in a virtual toolkit and also in conjunction with geo-registered tools and geo-registered virtual 3-D real person body structure. 3-D video type medical games would include, but are not limited to, the following: a learning experience of medical terminology of anatomy and bodily functions which can be comprehensive and/or competitive; a learning experience of pathology and its impact on bodily function which can be comprehensive and/or competitive; a learning experience of pathology and/or injuries which can be investigative and/or competitive; a 'hands-on experience' with virtual body parts; a learning experience whereby the participant(s) playing the game would perform virtual surgical operations; a learning experience whereby the participant(s) playing the game would perform virtual interventional operations; learn virtual body anatomy by putting a body back together, etc.

In some implementations for medical games, real patient medical images/data would be used to create a virtual 3D medical image of the real patient's body structure. In some implementations, a virtual tool kits would be available and tools could be selected and used by persons playing the game. Virtual tools could include a 3D cursor which could be used to encase some portion of the virtual 3D patient structure; the 3-D cursor could be resized, rotated in any particular direction and zoomed in on. Virtual tools could also be a virtual pointing device (e.g., pistol(s) with red dot(s); pointer with star at tip; laser pointer; movable check mark) would be available for the game player to designate objects of interest and obtain information about the patient's anatomy. A virtual knife tool could enable virtual operations to be performed by person(s) playing the game. A further tool could be virtual contrast added in lieu of virtual blood within the virtual vascular system. In some implementations, a tunnel view inside of an artery or vein could be provided the person(s) playing the game. Tunnel features could involve road signs for distances to key body features along with body icons to highlight location of the viewing object. Voxel manipulation could be invoked to enlarge the artery or vein such that the viewer could see the inside condition of the vein. Virtual catheters could be inserted to perform virtual operations on the on the patient. In some implementations surgical instruments could be inserted such as sewing clamps to open the surgical path in a virtual manner. A virtual hands-on anatomy could be used to help guide the person performing the virtual server virtual operation. In further implementations, virtual patient data could be presented via a virtual dashboard. And, message boards could be available to show questions and multiple-choice answers. A virtual table could be used for placement of virtual organs not currently being used.

In some implementations, image processing techniques of segmentation and filtration could assist in isolating the various organs of the body of the patient.

In some implementations, unique tangible objects would be geo-registered with the virtual 3D geo-registered medical structure and could interoperate with this structure. These tangible objects include, but are not limited to, the following: a geo-registered tangible platform/pedestal on which virtual body parts could be placed and platform/pedestal be held by the game player to examine the body parts of interest. A geo-registered knife could be used to perform a paring function of a virtual body to dissect a particular organ and peer into it. A geo-registered tangible focal point pen could be used as both a pointer and also as a instrument to interact with other game system components such as the virtual message board.

In some implementations, medical instruments could be available such as a tangible stethoscope with recorded sounds of hearts and lungs. A thermometer could be available at a version of a blood pressure sensor also. Other commonly used devices for physical examination, surgery, interventional procedures or various treatments can also be used.

In some implementations, the objective of the game would be to impart comprehensive knowledge of how the body works and how the body functions. This could include using a virtual implement such as a pointer to highlight a body structure or region thereof and the medical terminology and information regarding bodily function could appear. In some implementations, medical terminology could appear and the person playing the game would have to identify correct body structure. In some implementations, a competitive aspect could be created wherein players participate and challenge one another to their knowledge of anatomy.

In some implementations, the objective of the game would be to impart comprehensive knowledge of pathology. The type of information provided to person(s) playing the game could include pathologies such as: various types of cancer; various brain disorders; digestive system disorders; or pathologies involving any anatomic structure of the body.

In some implementations, the person(s) participating in the game could conduct interventional operations such as, but not limited to, the following: emplacing a stent; emplacing a pacemaker; declotting a dialysis graft or fistula; throbolysis of a pulmonary embolism or artery; and, treating a brain aneurysm.

In some implementations, the person participating in the game could learn virtual surgery by forming multiple types of surgical operations on the actual body. This could include, but would not be limited to: a performing a hip replacement in the setting of severe osteoarthritis; removing appendix in the setting of appendicitis; carving out cancer within the stomach and suturing the stomach closed, etc.

In some implementations, the person participating in the game could learn to manage emergent issues of a patient being rushed into the emergency room. This could include but not be limited to controlling bleeding; starting the breathing and treating shock. Lessons can be taught in accordance with Advanced Trauma Life Support (ATLS) principles.

In some implementations, a person participating in the game could learn to identify different types of cancer and gain an understanding of the treatment there thereof. The complexity and difficulty of the game can be varied. As an example, breast cancers can be more difficult to detect than lung cancers due to the fact that the cancer is of a more similar density/tissue composition. A breast cancer is surrounded by similar density breast tissue whereas a solid lung cancer is surrounded by most air-filled lung. Next, the difficulty can be varied based on the small size of the tumor. As a rule of thumb, smaller tumors can be more difficult to detect than larger tumors. The smaller tumors are typically lower stage and have not metastasized whereas the larger tumors are typically higher stage and may have metastasized.

In some implementations, the person participating in the game could be challenged to put together the pieces of the part of the body puzzle. As an example of this, the bones of the wrist (radius, ulna, scaphoid, lunate, triquetrum, pisiform, trapezium, trapezoid, capitate, hamate, metacarpals) can be scrambled in a random manner. The role of the video game player could be to place each bone into the appropriate locations as quickly as possible to create a wrist out of the scrambled pile of bones. Alternatively, all bones in the body can be scrambled.

In some implementations, surgical scenarios could be prepared for gaming purposes. Examples include but are not limited to: time critical treatment of a stroke; treating aneurysm; emplacing a stent; chemoembolization; and conducting a lung biopsy. In further implementations, preoperative planning of the various types of surgeries can be performed. Under these conditions, a game guru could give guidance regarding the conduct of the operation. During the conduct of the operation, changes in vital signs could accompany the scenario. These changes could trigger actions on the part of the gamer such as administering additional medications.

In some implementations, there are varying difficulty levels of play within the game. Different levels could be established wherein proficiency at the first level must be first achieved before advancing to a more difficult level.

In some implementations, a scoring system could be implemented wherein points are accumulated based on correct identification of medical terminology for differing parts of anatomy and associated bodily functions. A similar scoring process could be applied to pathologies. For investigative games, points could be given based on the accuracy and completeness of the diagnosis. Points could be assigned based on the accuracy and time to complete surgical and interventional operations.

In some implementations, the imaging data can be from animals rather than humans and the game geared towards players interested in veterinarian medicine. The purpose of these such implementations is instilling in the person playing in the game knowledge of animals.

In some implementations, the techniques described in this disclosure can be used for other types of interactions between virtual tools and geo-registered tools, which include, but are not limited to: virtual art (e.g., sculpting); construction (e.g., building a deck); mechanic type work (e.g., repairing a car); astronaut type work (e.g., repairing the outside of a space ship); underwater type work (e.g., underwater welding while wearing virtual scuba) or many other possibilities. In some implementations, the digital file as a result of the work performed with the geo-registered tools and virtual tools (e.g., a sculpture) can be sent to a 3D printer to print a real object.

In accordance with some aspects a method comprises: loading a selected three-dimensional image volume into an image processing system; assigning an interactive feature to an item that is present in the selected three-dimensional image volume; and manipulating the item within the three-dimensional image volume in accordance with the interactive feature in response to input from a geo-registered tool. In some implementations assigning an interactive feature comprises assigning a capability to change position, orientation, size, shape, color, texture, medical imaging type image alterations, or metrics related to interaction with the geo-registered tool. In some implementations assigning the interactive feature to an item comprises assigning the interactive feature to a single voxel, a group of voxels, a planar or non-planar two-dimensional slice, multiple two-dimensional slices arranged together to generate a volume, a three-dimensional cursor, a three-dimensional structure, or a medical structure corresponding to a patient scan or a simulated patient image. In some implementations input from the geo-registered tool comprises manipulating a platform upon which the item is placed. In some implementations input from the geo-registered tool comprises manipulating a focal point pen. In some implementations input from the geo-registered tool comprises manipulating a cutting tool. In some implementations input from the geo-registered tool comprises manipulating a catheter. Some implementations comprise assigning a virtual task to a first user. Some implementations comprise detecting a location in the selected three-dimensional image volume upon which a first user's eyes are focused and providing an indication of that location to a second user. In some implementations assigning the virtual task to the first user comprises assigning a medical procedure. Some implementations comprise prompting performance of an additional task selected from the group consisting of: treating a stroke; treating aneurysm; emplacing a virtual stent; chemoembolization; and conducting a lung biopsy. Some implementations comprise scoring performance of the virtual task based on manipulation of the item. Some implementations comprise scoring performance based on correct identification of medical terminology for differing parts of anatomy and associated bodily functions. Some implementations comprise scoring performance based on accuracy and completeness of a diagnosis. Some implementations comprise scoring performance based on accuracy and time to complete a surgical operation. Some implementations comprise scoring performance based on accuracy and time to complete an interventional operation.

In accordance with some aspects an apparatus comprises: an image processing system into which a selected three-dimensional image volume is loaded, the image processing system comprising program code that assigns an interactive feature to an item that is present in the selected three-dimensional image volume and manipulates the item within the three-dimensional image volume in accordance with the interactive feature in response to input from a geo-registered tool. In some implementations the interactive feature comprises a capability to change position, orientation, size, shape, color, texture, medical imaging type image alterations, or metrics related to interaction with the geo-registered tool. In some implementations the item comprises a single voxel, a group of voxels, a planar or non-planar two-dimensional slice, multiple two-dimensional slices arranged together to generate a volume, a three-dimensional cursor, a three-dimensional structure, or a medical structure corresponding to a patient scan or a simulated patient image. In some implementations the input from the geo-registered tool comprises manipulation of a platform upon which the item is placed. In some implementations the input from the geo-registered tool comprises manipulation of a focal point pen. In some implementations the input from the geo-registered tool comprises manipulation of a cutting tool. In some implementations the input from the geo-registered tool comprises manipulation of a catheter. Some implementations comprise a virtual task that is assigned to a first user. Some implementations comprise a tracking mechanism that detects a location in the selected three-dimensional image volume upon which a first user's eyes are focused and an image generator that provides an indication of that location to a second user. In some implementations the virtual task comprises a medical procedure. Some implementations comprise an additional task selected from the group consisting of: treating a stroke; treating aneurysm; emplacing a virtual stent; chemoembolization; and conducting a lung biopsy. Some implementations comprise a processor that calculates a performance score for the virtual task based on manipulation of the item. Some implementations comprise a processor that calculates a performance score for the virtual task based on correct identification of medical terminology for differing parts of anatomy and associated bodily functions. Some implementations comprise a processor that calculates a performance score for the virtual task based on accuracy and completeness of a diagnosis. Some implementations comprise a processor that calculates a performance score for the virtual task based on accuracy and time to complete a surgical operation. Some implementations comprise a processor that calculates a performance score for the virtual task based on accuracy and time to complete an interventional operation.

BRIEF DESCRIPTION OF FIGURES

FIGS. 14A, 14B and 14C illustrate a virtual ride through a virtual vascular tunnel with road sign for a person playing the game using a visual transport tool.

FIGS. 15A, 15B and 15C illustrate the virtual catheter, which could be used in conjunction with a volumetric medical image of the vascular structure within the patient with the assistance of virtual icons.

FIGS. 16A, 16B and 16C illustrate the general concept of 3D medical images and example techniques behind the explosion of 3D medical images into multi separate organs, which can then be individually selected by person playing the game.

FIG. 25 illustrates the geo-registered true stereoscopic head display unit within the geo-registration coordinate system viewing a 3D cursor.

FIG. 28 illustrates the hand-held pedestal within the geo-registration coordinate system equipped with a geo-registration point, contains an inertial measurement unit for determining location and/or orientation, and a transmit/receive unit for communication with the computer.

FIGS. 42A, 42B and 42C illustrate an example dashboard, message board, and body icon.

FIGS. 43A and 43B illustrate the competitive structure of the game example scoring process.

FIG. 44 illustrates learning objectives of different aspects of the games and example scenarios.

DETAILED DESCRIPTION OF FIGURES

Figure 1:
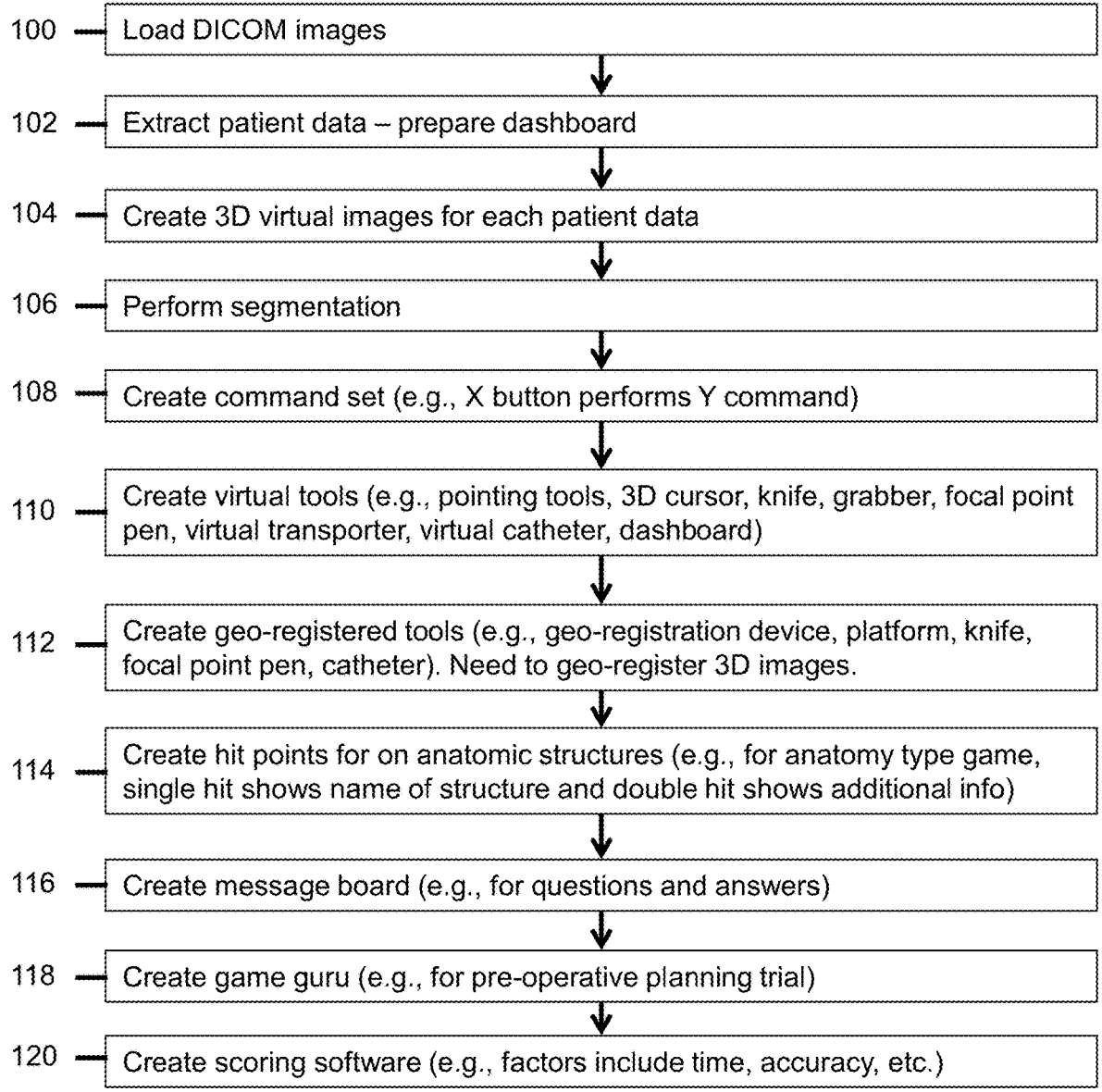
FIG. 1 illustrates a flow chart for software loaded on game player's processor before the player starts the game.

FIG. 1 illustrates a flow chart for software loaded on game player's processor before the player starts the game. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. For example, a first step 100 is to load DICOM images. A second step 102 is to extract patient data and prepare the dashboard. The third step 104 is to create 3D virtual images for each patient data. A fourth step 106 is to perform segmentation. A fifth step 108 is to create a command set (e.g. "X" button performs Y command, etc.). A sixth step 110 is to create virtual tools (e.g., pointing tools, 3D cursor, knife, grabber, focal point pen, virtual transporter, virtual catheter, dashboard). A seventh step 112 is to create geo-registered tools (e.g., geo-registration device, platform, knife, focal point pen, catheter). Also, geo-registration of 3D images should be performed. An eighth step 114 is to create hit points for on anatomic structures (e.g., for anatomy type game, single hit shows name of structure and double hit shows additional info). A ninth step 116 is to create a message board (e.g., for questions and answers). A tenth step 118 is to create a game guru (e.g., for pre-operative planning trial). An eleventh step 120 is to create scoring software (e.g., factors include time, accuracy, etc.).

Figure 2:
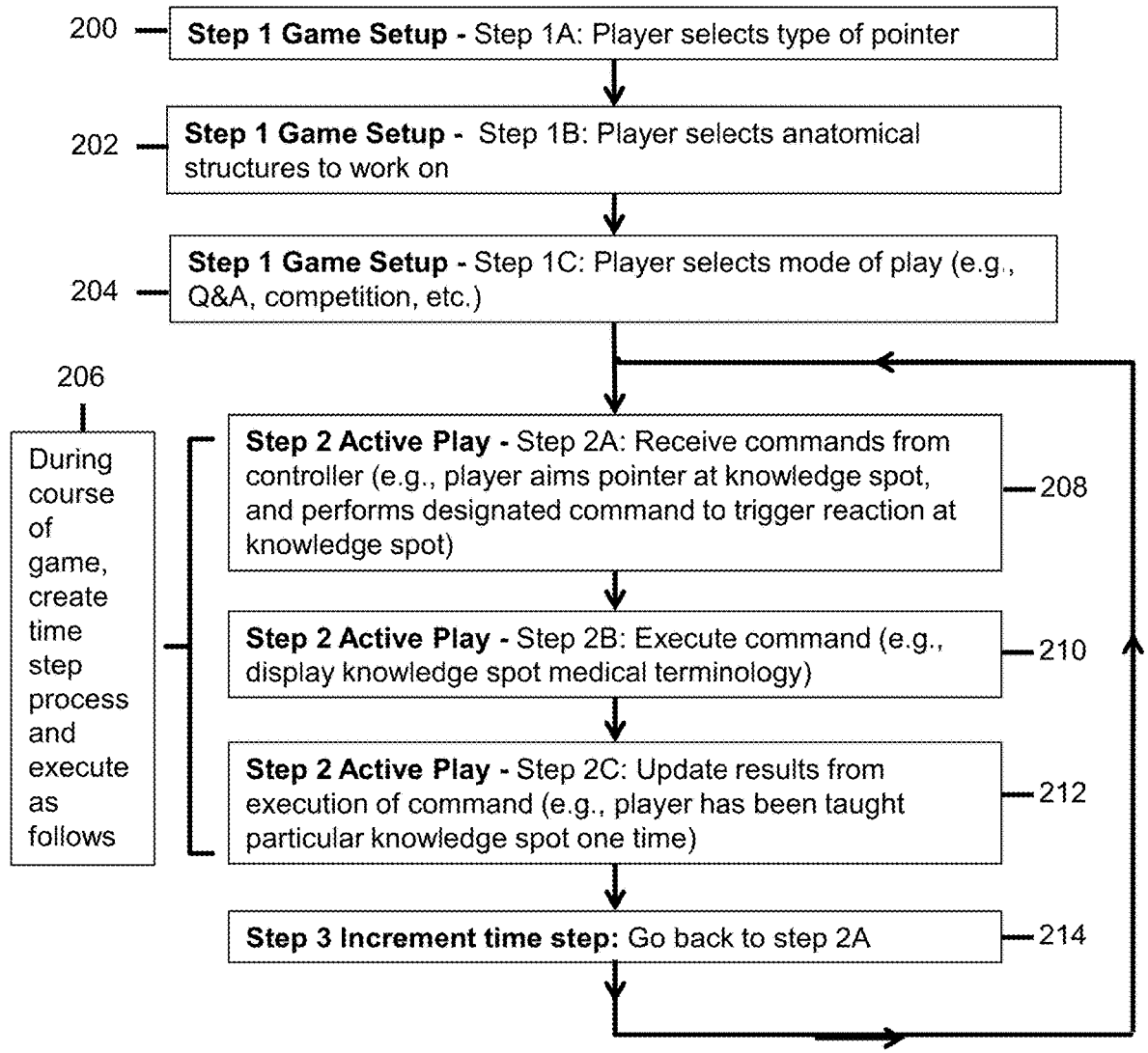
FIG. 2 illustrates a flow chart for software to be used in real time when the player plays the game with an example of an anatomy or pathology knowledge type game.

FIG. 2 illustrates a flow chart for software to be used in real time when the player plays the game with an example of an anatomy or pathology knowledge type game. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. For example, an anatomy or pathology knowledge type game is described in this flow diagram. Step 1A Game Setup 200 is for the player to select the type of pointer. Step 1B Game Setup 202 is for the player to select the anatomical structure to work on. Step 1C Game Setup 204 is for the player to select the mode of play (e.g., question and answer, competition, etc.). Note that 206 during the course of the game, a time step process is created and executed. Step 2A 208 is for the player to receive commands from the controller (e.g., the player aims the pointer at a knowledge spot and performs designated command to trigger a reaction at the knowledge spot). Note that the knowledge spot can have a variety of visual indicators. Step 2B Active Play 210 is for the is to execute the command (e.g., display knowledge spot medical terminology). Step 2C Active Play 212 is to update the results from execution of the command (e.g., player has been taught particular knowledge spot one time). Step 3 Increment time step 214 is for the user to return to Step 2A Active Play 208.

Figure 3:
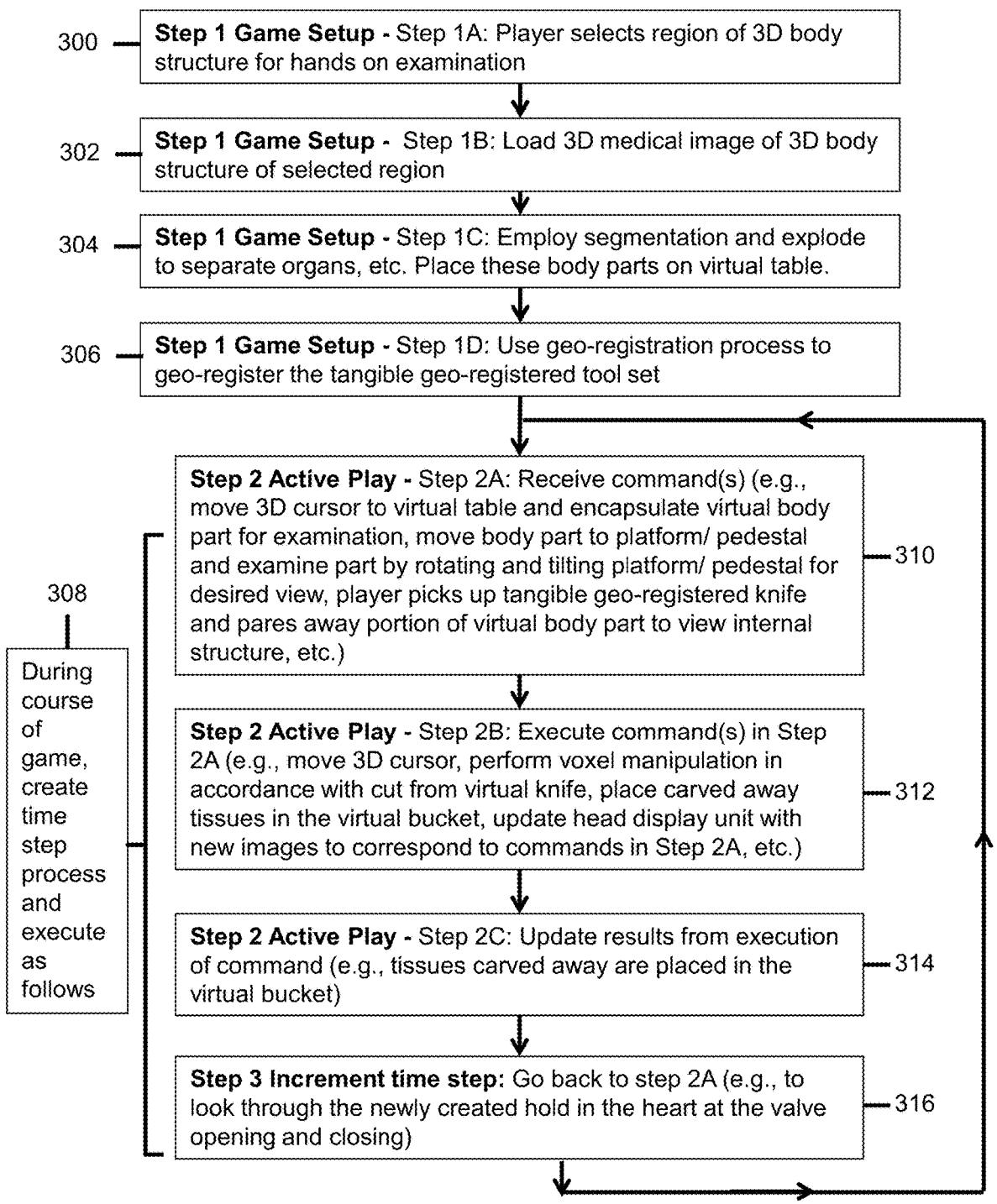
FIG. 3 illustrates a flow chart for software to be used in real time when the player plays the game with an example of a hands-on type anatomy game, such as carving into the heart.

FIG. 3 illustrates a flow chart for software to be used in real time when the player plays the game with an example of a hands-on type anatomy game, such as carving into the heart. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. In Step 1A Game Setup 300, the player selects region of 3D body structure for hands on examination. In Step 1B Game Setup 302, load 3D medical image of 3D body structure of selected region. In Step 1C Game Setup 304, employ segmentation and explode to separate organs, etc. Place these body parts on virtual table. In Step 1D Game Setup 306, use geo-registration process to geo-register the tangible geo-registered tool set. During course of game 308, create time step process and execute. In Step 2A, receive command(s) (e.g., move 3D cursor to virtual table and encapsulate virtual body part for examination, move body part to platform/pedestal and examine part by rotating and tilting platform/pedestal for desired view, player picks up tangible geo-registered knife and pares away portion of virtual body part to view internal structure, etc.). In Step 2B 312, execute command(s) in Step 2A 310 (e.g., move 3D cursor, perform voxel manipulation in accordance with cut from virtual knife, place carved away tissues in the virtual bucket, update head display unit with new images to correspond to commands in Step 2A 310, etc.). In Step 2C 314, update results from execution of command (e.g., tissues carved away are placed in the virtual bucket). In Step 3 316, increment the time step and go back to step 2A 310 (e.g., to look through the newly created hold in the heart at the valve opening and closing).

Figure 4:
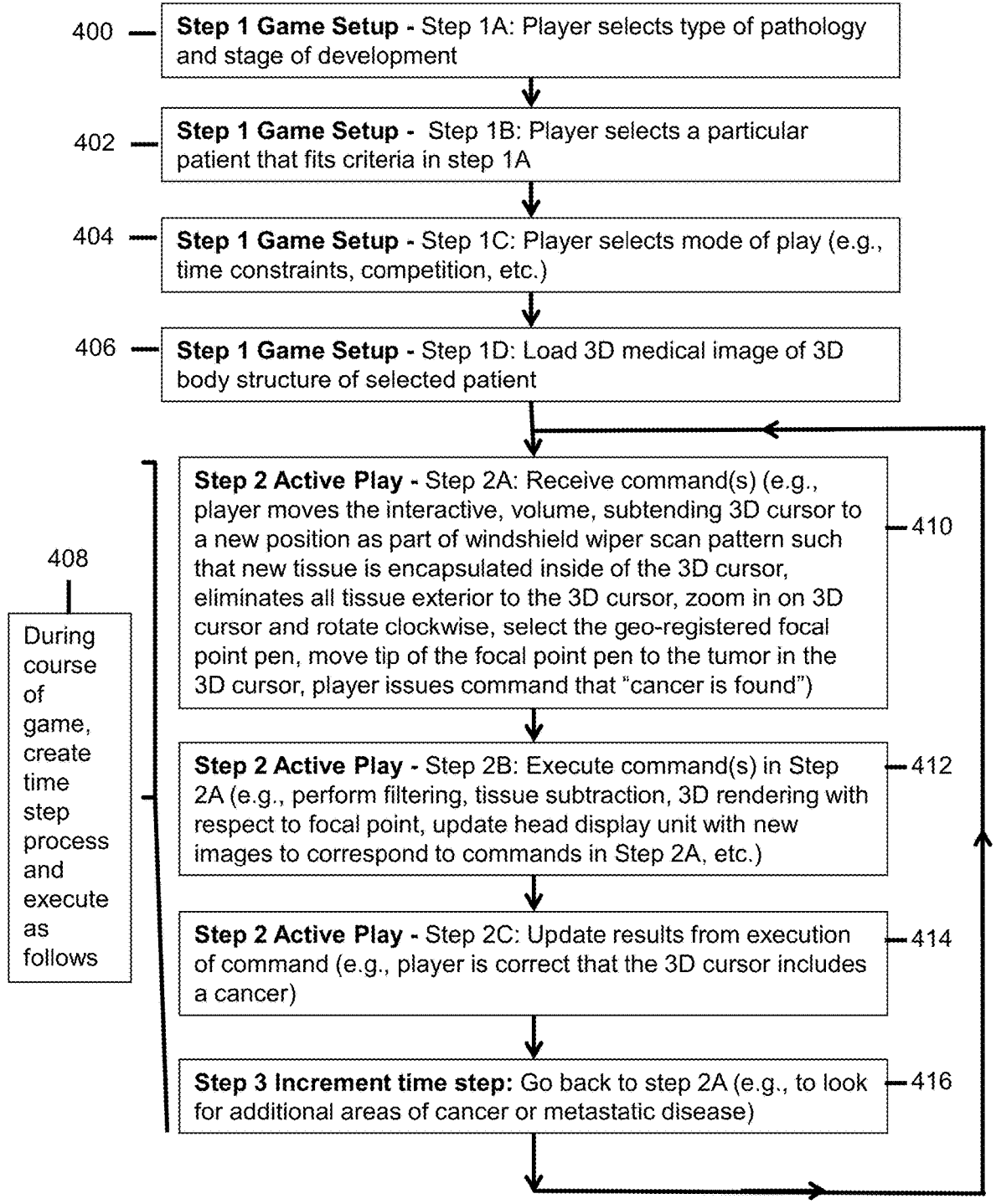
FIG. 4 illustrates a flow chart for software to be used in real time when the player plays the game with an example of an investigative type game, such as finding cancer.

FIG. 4 illustrates a flow chart for software to be used in real time when the player plays the game with an example of an investigative type game, such as finding cancer. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. In Step 1A 400 player selects type of pathology and stage of development. In Step 1B 402, player selects a particular patient that fits criteria in step 1A. In Step 1C 404, player selects mode of play (e.g., time constraints, competition, etc.). In Step 1D 406, load 3D medical image of 3D body structure of selected patient. During course of game 408, create time step process and execute. In Step 2A Active Play 410, receive command(s) (e.g., player moves the interactive, volume, subtending 3D cursor to a new position as part of windshield wiper scan pattern such that new tissue is encapsulated inside of the 3D cursor, eliminates all tissue exterior to the 3D cursor, zoom in on 3D cursor and rotate clockwise, select the geo-registered focal point pen, move tip of the focal point pen to the tumor in the 3D cursor, player issues command that "cancer is found"). In Step 2B Active Play 412, execute commands in Step 2A 410 (e.g., perform filtering, tissue subtraction, 3D rendering with respect to focal point, update head display unit with new images to correspond to commands in Step 2A 410, etc.). In Step 2C Active Play 414, update results from execution of command (e.g., player is correct that the 3D cursor includes a cancer). In Step 3 Increment time Step 416, go back to step 2A (e.g., to look for additional areas of cancer or metastatic disease).

Figure 5:
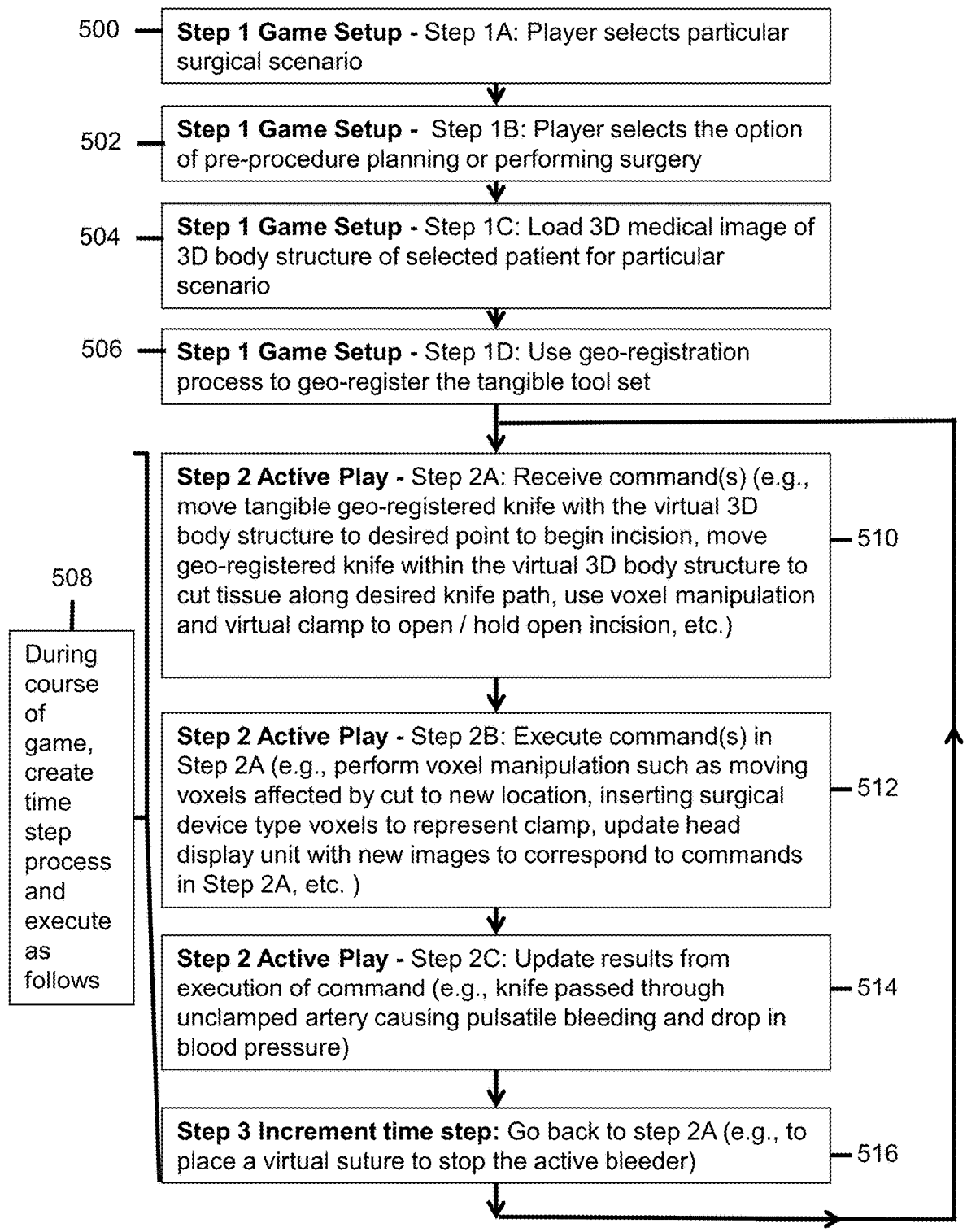
FIG. 5 illustrates a flow chart for software to be used in real time when the player plays the game with an example of a surgery type game, such as performing a lumpectomy.

FIG. 5 illustrates a flow chart for software to be used in real time when the player plays the game with an example of a surgery type game, such as performing a lumpectomy. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. In Step 1A 500, player selects particular surgical scenario. In Step 1B 502, player selects the option of pre-procedure planning or performing surgery. In Step 1C 504, load 3D medical image of 3D body structure of selected patient for particular scenario. In Step 1D 506, use geo-registration process to geo-register the tangible tool set. During course of game 508, create time step process and execute. In Step 2A Active Play 510, receive command(s) (e.g., move tangible geo-registered knife with the virtual 3D body structure to desired point to begin incision, move geo-registered knife within the virtual 3D body structure to cut tissue along desired knife path, use voxel manipulation and virtual clamp to open/hold open incision, etc.). In Step 2B Active Play 512, execute command(s) in Step 2A (e.g., perform voxel manipulation such as moving voxels affected by cut to new location, inserting surgical device type voxels to represent clamp, update head display unit with new images to correspond to commands in Step 2A, etc.). In Step 2C Active Play 514, update results from execution of command (e.g., knife passed through unclamped artery causing pulsatile bleeding and drop in blood pressure). In Step 3 Increment time step 516, go back to step 2A (e.g., to place a virtual suture to stop the active bleeder).

Figure 6:
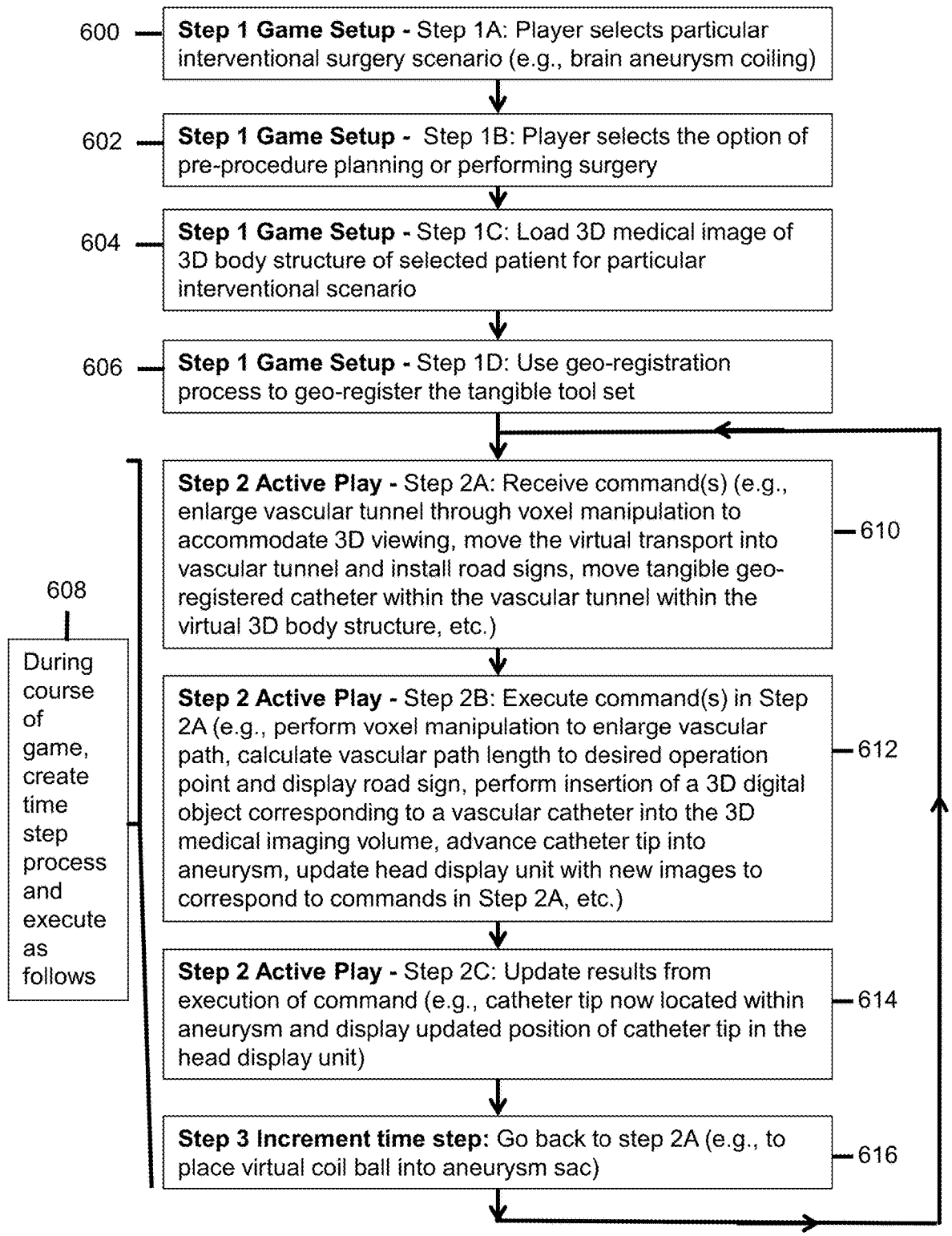
FIG. 6 illustrates a flow chart for software to be used in real time when the player plays the game with an example of an interventional surgery type game, such as coiling of a brain aneurysm.

FIG. 6 illustrates a flow chart for software to be used in real time when the player plays the game with an example of an interventional surgery type game, such as coiling of a brain aneurysm. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. In Step 1A 600, player selects particular interventional surgery scenario (e.g., brain aneurysm coiling). In Step 1B 602, player selects the option of pre-procedure planning or performing surgery. In Step 1C 604, load 3D medical image of 3D body structure of selected patient for particular interventional scenario. In Step 1D 606, use geo-registration process to geo-register the tangible tool set. During course of game 608, create time step process and execute. In Step 2A Active Play 610, receive command(s) (e.g., enlarge vascular tunnel through voxel manipulation to accommodate 3D viewing, move the virtual transport into vascular tunnel and install road signs, move tangible geo-registered catheter within the vascular tunnel within the virtual 3D body structure, etc.). In Step 2B 612, execute command(s) in Step 2A (e.g., perform voxel manipulation to enlarge vascular path, calculate vascular path length to desired operation point and display road sign, perform insertion of a 3D digital object corresponding to a vascular catheter into the 3D medical imaging volume, advance catheter tip into aneurysm, update head display unit with new images to correspond to commands in Step 2A 610, etc.). In Step 2C 614, update results from execution of command (e.g., catheter tip now located within aneurysm and display updated position of catheter tip in the head display unit). In Step 3 Increment time step, go back to step 2A 610 (e.g., to place virtual coil ball into aneurysm sac).

Figure 7:
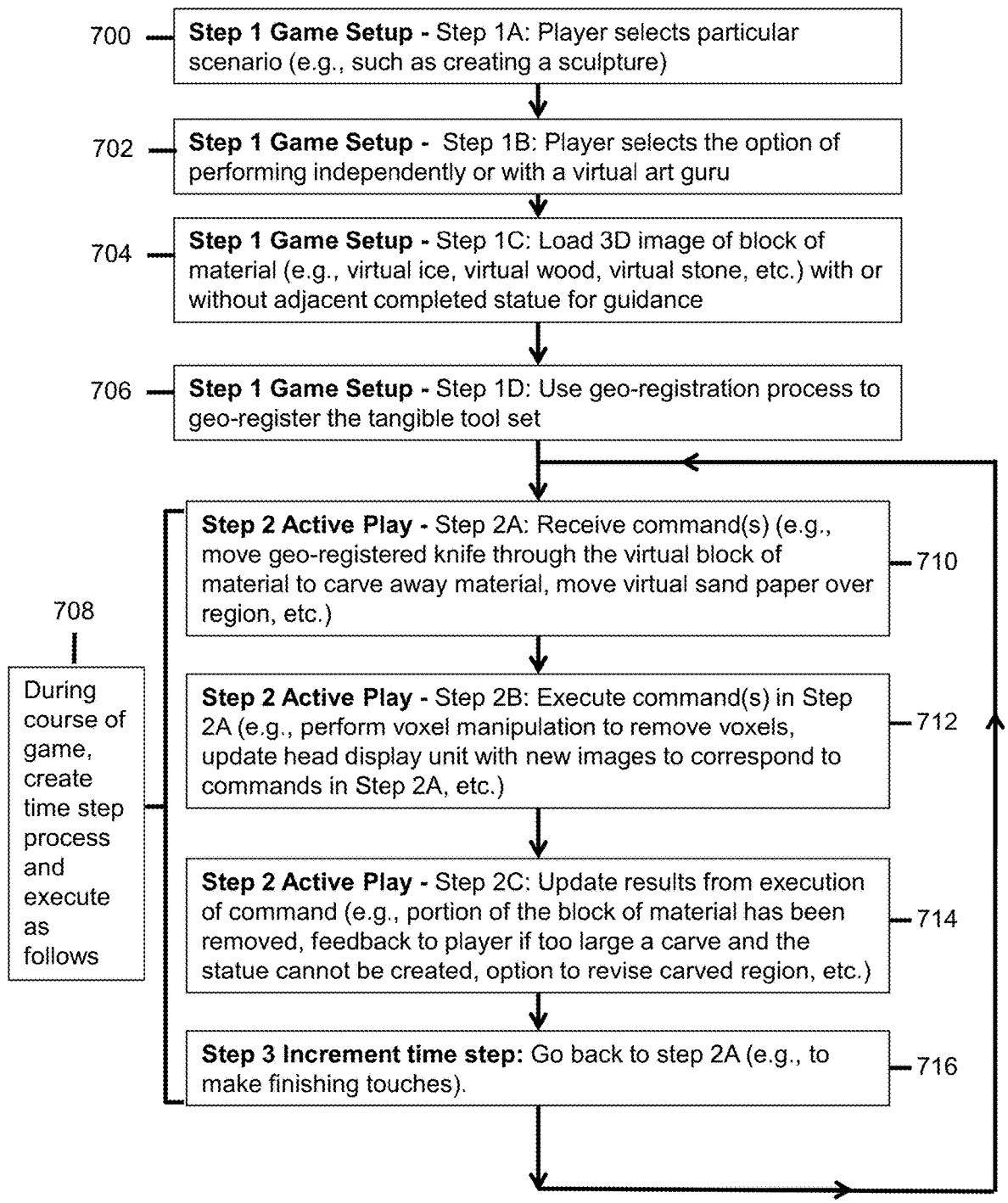
FIG. 7 illustrates a flow chart for software to be used in real time when the player plays the game with an example of an art type game, such as carving of a virtual sculpture.

FIG. 7 illustrates a flow chart for software to be used in real time when the player plays the game with an example of an art type game, such as carving of a virtual sculpture. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. In Step 1A Game Setup 700, player selects particular scenario (e.g., such as creating a sculpture). In Step 1B Game Setup 702, player selects the option of performing independently or with a virtual art guru. In Step 1C Game Setup 704, load 3D image of block of material (e.g., virtual ice, virtual wood, virtual stone, etc.) with or without adjacent completed statue for guidance. In Step 1D Game Setup 706, use geo-registration process to geo-register the tangible tool set. During course of game 708, create time step process and execute. During Step 2A Active Play 710, receive command(s) (e.g., move geo-registered knife through the virtual block of material to carve away material, move virtual sand paper over region, etc.). In Step 2B Active Play 712, execute command(s) in Step 2A (e.g., perform voxel manipulation to remove voxels, update head display unit with new images to correspond to commands in Step 2A, etc.). In Step 2C Active Play 714, update results from execution of command (e.g., portion of the block of material has been removed, feedback to player if too large a carve and the statue cannot be created, option to revise carved region, etc.). In Step 3 Increment time step 716, go back to step 2A 710 (e.g., to make finishing touches).

Figure 8:
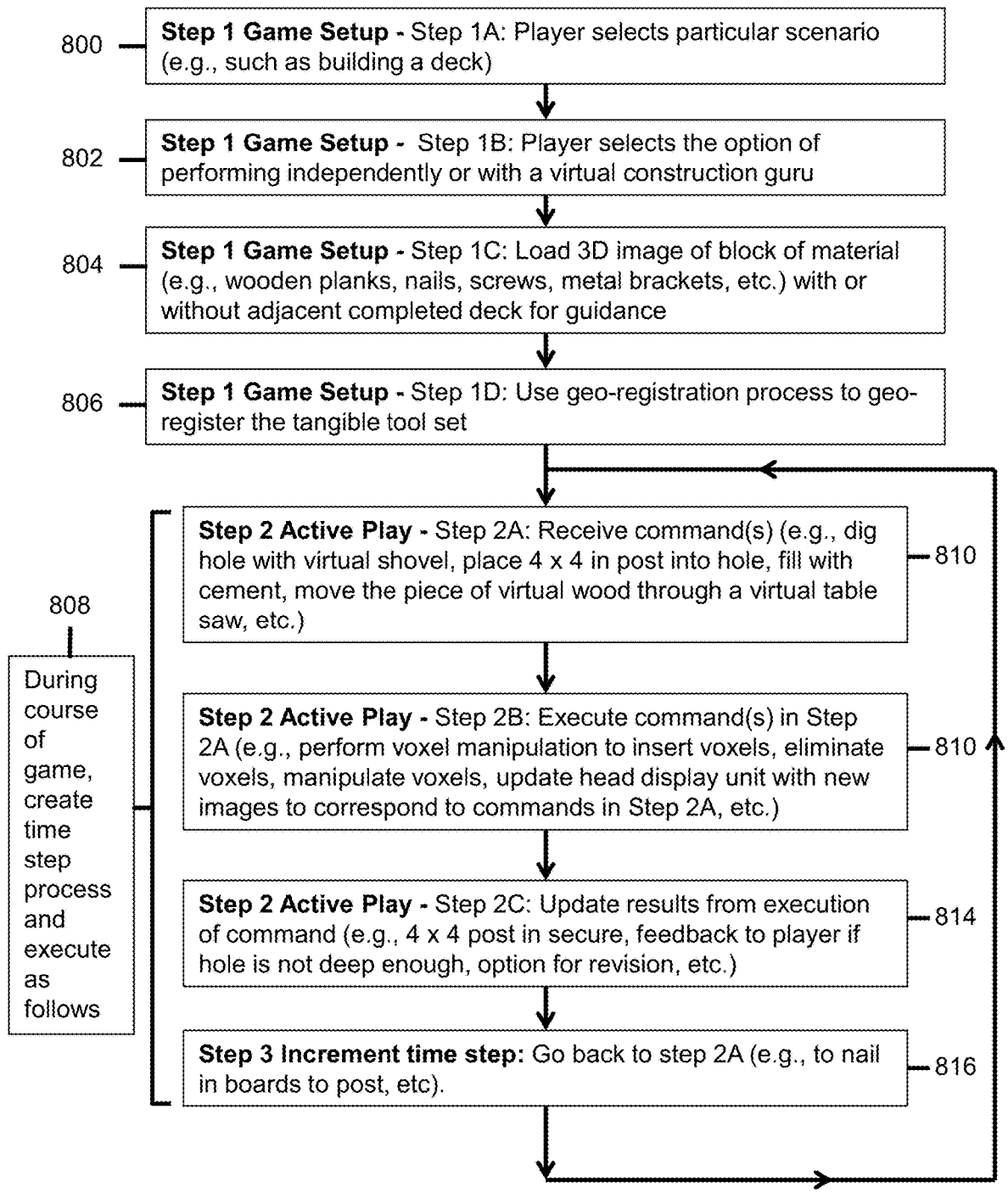
FIG. 8 illustrates a flow chart for software to be used in real time when the player plays the game with an example of a carpenter type game, such as building a deck.

FIG. 8 illustrates a flow chart for software to be used in real time when the player plays the game with an example of a carpenter type game, such as building a deck. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. In Step 1A Game Setup 800, player selects particular scenario (e.g., such as building a deck). In Step 1B 802, player selects the option of performing independently or with a virtual construction guru. In Step 1C 804, load 3D image of block of material (e.g., wooden planks, nails, screws, metal brackets, etc.) with or without adjacent completed deck for guidance. In Step 1D 806, use geo-registration process to geo-register the tangible tool set. During the course of the game 808, create time step process and execute. In Step 2A Active Play 810, receive command(s) (e.g., dig hole with virtual shovel, place 4×4 in post into hole, fill with cement, move the piece of virtual wood through a virtual table saw, etc.). In Step 2B Active Play 812, execute command(s) in Step 2A (e.g., perform voxel manipulation to insert voxels, eliminate voxels, manipulate voxels, update head display unit with new images to correspond to commands in Step 2A, etc.). In Step 2C Active Play 814, update results from execution of command (e.g., 4×4 post in secure, feedback to player if hole is not deep enough, option for revision, etc.). In Step 3 Increment time step 814, go back to step 2A 810 (e.g., to nail in boards to post, etc.).

Figure 9:
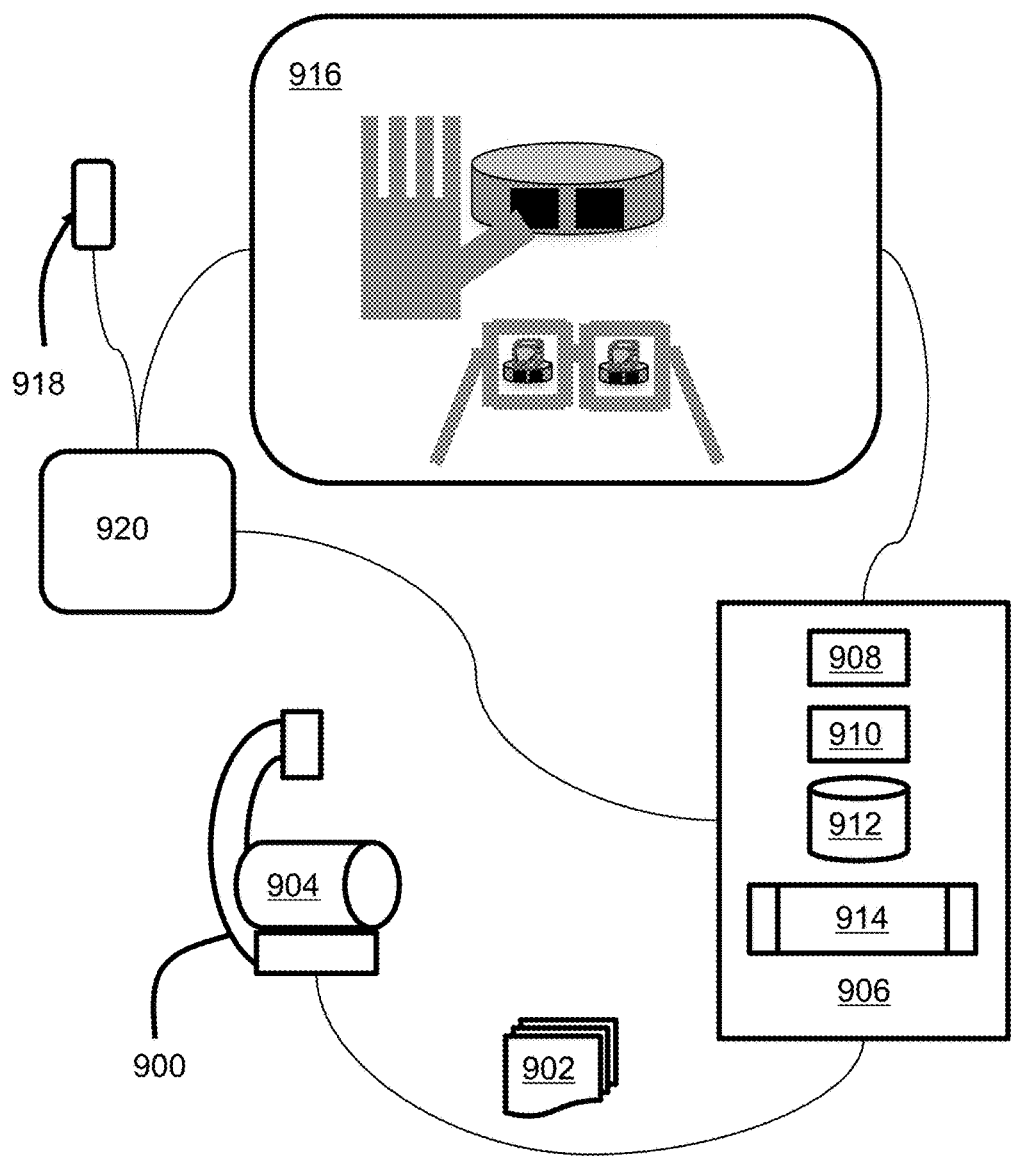
FIG. 9 illustrates an overview of the apparatus used for the interaction of virtual tools and geo-registered tools.

FIG. 9 illustrates an overview of the apparatus used for the interaction of virtual tools and geo-registered tools. A radiologic imaging system 900 (e.g., X-ray, ultrasound, CT (computed Tomography), PET (Positron Emission Tomography), or MRI (Magnetic Resonance Imaging)) is used to generate 2D medical images 902 of an anatomic structure 904 of interest. The 2D medical images 902 are provided to an image processor 906, that includes processors 908 (e.g., CPUs and GPUs), volatile memory 910 (e.g., RAM), and non-volatile storage 912 (e.g. HDDs and SSDs). A program 914 running on the image processor implements one or more of the steps described in FIG. 1. 3D medical images are generated from the 2D medical images and displayed on an IO device 916. The IO device may include a virtual or augmented reality headset, monitor, tablet computer, PDA (personal digital assistant), mobile phone, or any of a wide variety of devices, either alone or in combination. The IO device may include a touchscreen and, may accept input from external devices (represented by 918) such as a keyboard, mouse, and any of a wide variety of equipment for receiving various inputs. However, some or all the inputs could be automated, e.g. by the program 914. Finally, as discussed further in this patent, a series of virtual tools 920 are implemented, which facilitate viewing of medical images by person(s) playing the game(s).

Figure 10:
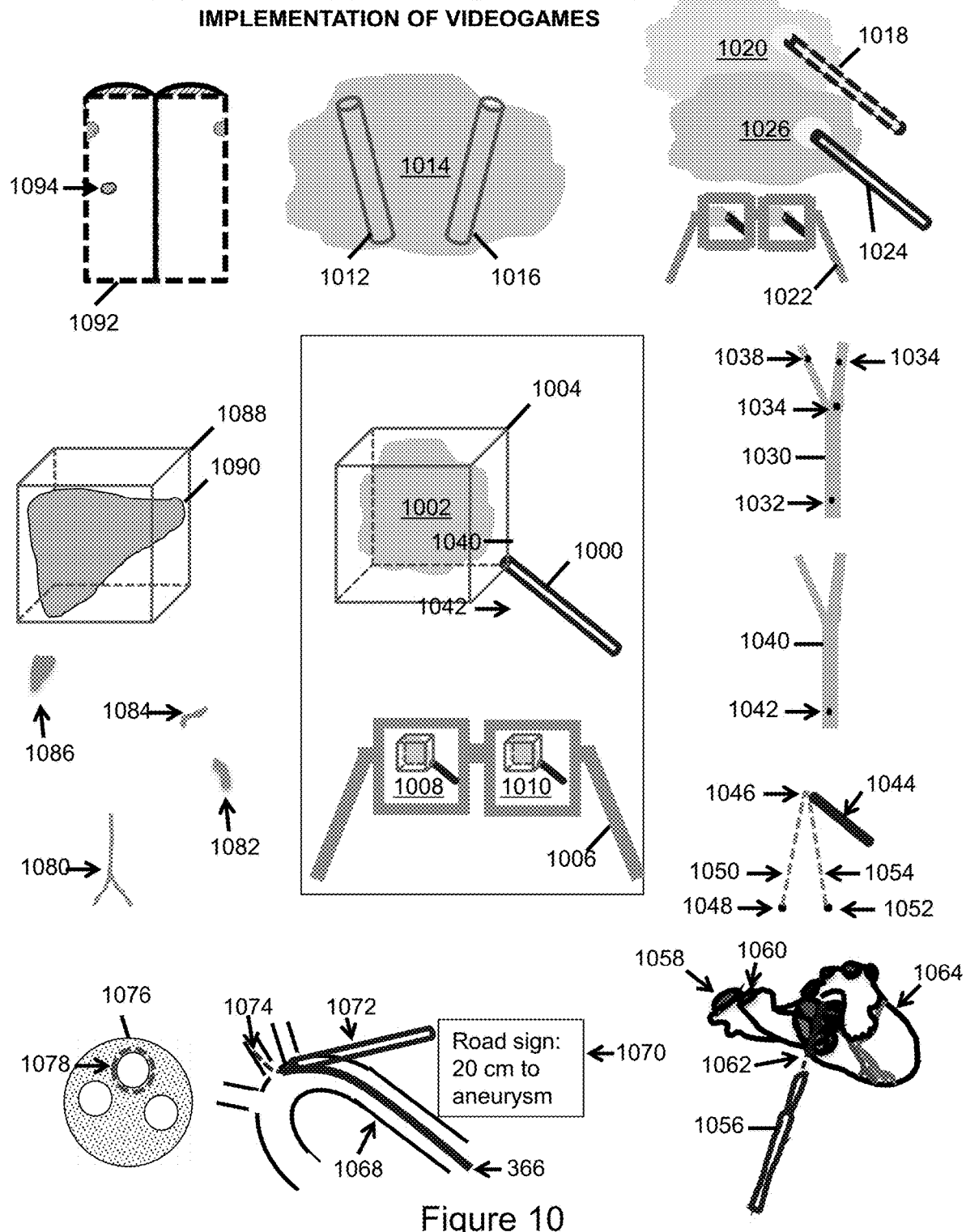
FIG. 10 illustrates virtual toolkit options in viewing volumetric medical images in the virtual implementation of videogames.

FIG. 10 illustrates virtual toolkit options in viewing volumetric medical images in the virtual implementation of videogames. In this figure, representative examples of viewing options available through the use of a virtual tools are illustrated. Options by which the virtual tools can be guided/selected could be presented on the display and the user would click on desired option. In the center of the illustration, the virtual tool 1000 (i.e., virtual focal point pen) is geo-registered within the medical imaging volume. The virtual focal point pen is superimposed within the region containing the virtual 3D medical image 1002 located inside of the 3D cursor 1004. A button (e.g., on the keyboard) plus a movement of a virtual tool can be coupled together to size the 3D cursor 1004 (e.g., select the center of the 3D cursor 1004 and then move the virtual focal point pen 1000 a distance away to correspond to the radius). The user views the virtual tool using a headset 1006 (e.g., augmented reality, mixed reality or virtual reality) glasses with a left eye display 1008 and right eye display 1010. The virtual focal point pen can be registered within the virtual image by touching specific spots (e.g., corners) of the medical imaging volume 1002. For display purposes, the medical personnel can select to only show the tip of the focal point pen in the display, enlarge the tip of the focal point pen as desired, and/or show the virtual image of the focal point pen in its entirety as it is oriented within the volume. Movement of the virtual focal point pen 1000 would be controlled by medical person viewing the medical images. The virtual focal point pen 1000 is useful when smooth pursuit eye movements are necessary. For example, smooth pursuit eye movements are necessary when examining arteries for any blockages, wherein using the virtual focal point pen to trace along arteries looking for blockages. Saccadian eye movement could result in skipping over portions of the artery and a serious blockage go undetected; therefore, the virtual focal point pen 1000 could be helpful in aiding this search pattern. Multiple colored/shaped virtual focal point pens 1000 could be used to trace the different flows of arteries and veins. In the top image, the position and orientation of the virtual tool changes with respect to the volume of interest. The virtual focal point pen is shown with an initial position and orientation 1012 with respect to the volume of interest 1014. Then, the user can move the virtual focal point pen to a subsequent position and orientation 1016 with respect to the volume of interest 1014. Proceeding clockwise, next the virtual focal point pen 1018 performs grabbing of the volume of interest 1020 at an initial distance from the head display unit 1022. Then, the virtual vocal point pen 1024 pulls the volume of interest 1026 closer to the head display unit 1022 for improved visualization. Alternatively, the volume of interest 1020 could be moved in other positions or orientations by the focal point pen 1018. Next, a virtual dot can be placed on or next to a portion of the virtual image 1030 (e.g., carotid artery) being examined in a fixed or dynamic manner. For example, the dot can appear and disappear at multiple spots along the vascular structure to facilitate Saccadian viewing where the eyes jump short distances to view the most important portions of the vascular structure. At time point #1, a first virtual dot 1032 appears and no other virtual dots are shown in the field of view at this time. At time point #2, a second virtual dot 1034 appears and no other virtual dots are shown in the field of view at this time. At time point #3, a third virtual dot 1036 appears and no other virtual dots are shown in the field of view at this time. At time point #4, a fourth virtual dot 1038 appears and no other virtual dots are shown in the field of view at this time. Alternatively, the virtual dot 1042 can be moving along a portion of the virtual image 1040 (e.g., carotid artery) to help the human eye perform smooth tracking and enhanced viewing of the vascular structure. Next, the virtual focal point pen 1044 is used to perform convergence to a focal point 1046. A left eye view point 348 is shown. A line illustrating the look angle of the left eye 1050 is also shown. A right eye view point 1052 is shown. A line illustrating the look angle of the right eye 1054 is also shown. Note that the look angle 1050 from the left eye view point 1048 and the look angle 1054 from the right eye view point 1052 intersect at the convergence point 1046. Next, a virtual dissection is performed by using a virtual knife 1056 and the aorta 1058 and pulmonary artery 1060 are cut and moved away from the rest of the heart 1064. Note the cutting plane 1062 is shown. Next, a virtual catheter 1066 is being placed through the aorta 1068 within the medical imaging volume. Note that a virtual road sign 1070 is shown to guide the medical personnel. The focal point pen 1072 is shown. The dotted line blue line 1074 is the desired catheter trajectory, which can be at different time setting. The virtual catheter 1066 can be pulled through the vascular system. A ride through the blood vessel type viewing is shown 1076 with the desired path highlighted in a dotted red circle 1078. The last three examples illustrate advanced viewing options enabled by the virtual tools. An explosion-type viewing where the organs are separated is illustrated wherein the various organs are separate. For example, the amount of spacing between the various abdominal organs including the aorta 1080, left kidney 1082, pancreas 1084 and liver 1086 is increased. Next, a virtual ablation is performed wherein the outer shell 390 of a virtual tissue are sequentially removed over multiple time points. The anatomic structure in which virtual ablation is performed can be placed in a 3D cursor 1088 to help direct the ablation. Finally, a structure such as the colon 1092 can be sliced (e.g., using a virtual knife) and opened such that the inner aspects including a polyp 1094 inside the hollow viscus can be more carefully examined. Voxel manipulation would be required to achieve this aspect.

Figure 11A:
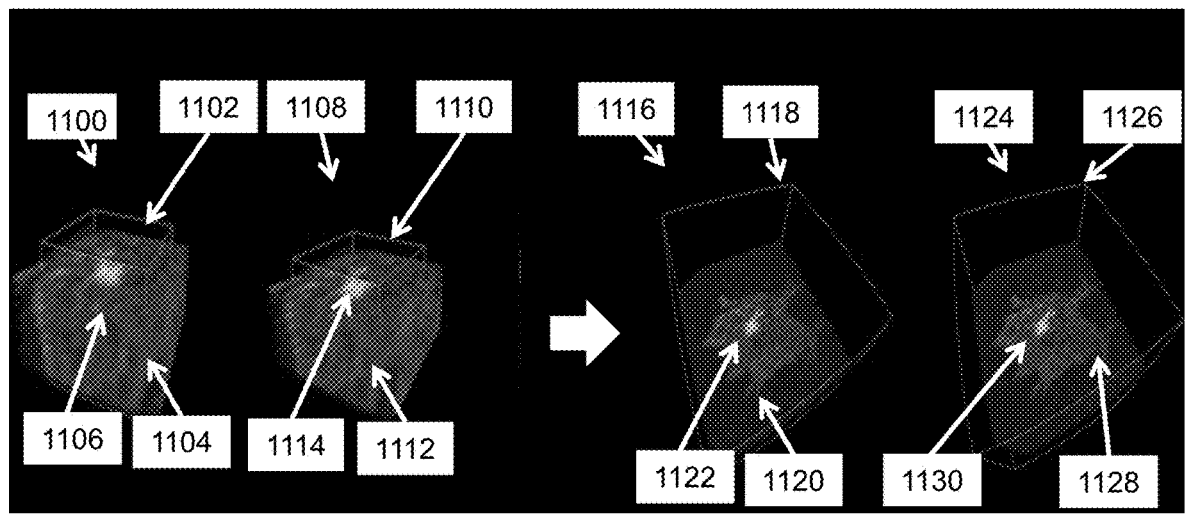
FIGS. 11A and 11B illustrate an example use of an interactive, volume-subtending 3D cursor in 3D medical images.
Figure 11B:
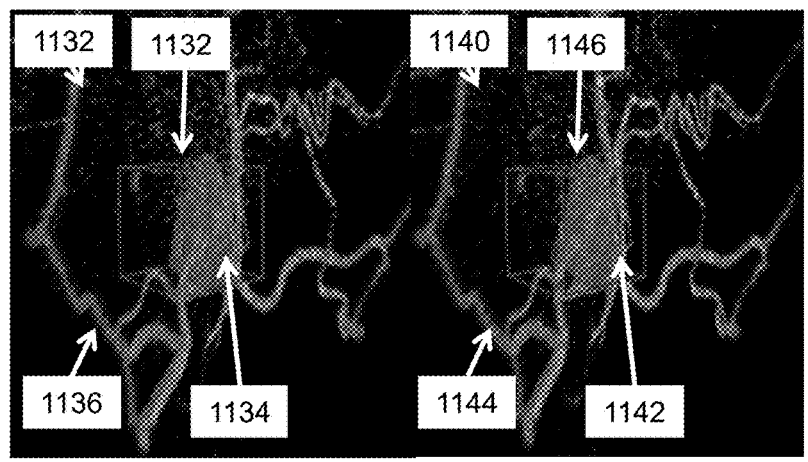

FIG. 11A illustrates the a left eye image 1100 of the volume subtending 3D cursor 1102 encompassing a volume of normal breast tissue 1104 in mid gray color and a breast cancer in white 1106. Also, note the right eye view 1108 of the volume subtending 3D cursor 1110 encompassing a volume of normal breast tissue 1112 in mid gray color and a breast cancer in white 1114. Note that the video game player sees a left eye image 1100 with his left eye and a right eye image with his right eye 1102 in the head display unit, which yields depth perception. Subsequently, the video game player changes the viewing parameters including resizing the 3D cursor, rotation of the volume of interest/ altering the viewing angles, such that and a new left eye image 1116 of the resized volume subtending 3D cursor 1118 encompassing a volume of normal breast tissue 1120 in mid gray color and a breast cancer in white 1122 is shown. Also, a new right eye image 1124 of the volume subtending 3D cursor 1126 encompassing a volume of normal breast tissue in gray shades 1128 and a breast cancer in white 1130. FIG. 11B illustrates an example of filtration wherein the medium density gray tissues in FIG. 11A have been removed. A left eye image 1132 is shown wherein the breast mass 1134 and blood vessels 1136 coursing through the breast are seen. Note that the breast tissue has been subtracted (i.e., filtered). Note that a volume subtending 3D cursor 1138 has been placed around the breast mass 1134. A right eye image 1140 is shown wherein the breast mass 1142 and blood vessels 1144 coursing through the breast are seen. Note that the normal breast glandular tissue has been subtracted (i.e., filtered/removed). Note that a volume subtending 3D cursor 1146 has been placed around the breast mass 1142.

Figure 12A:
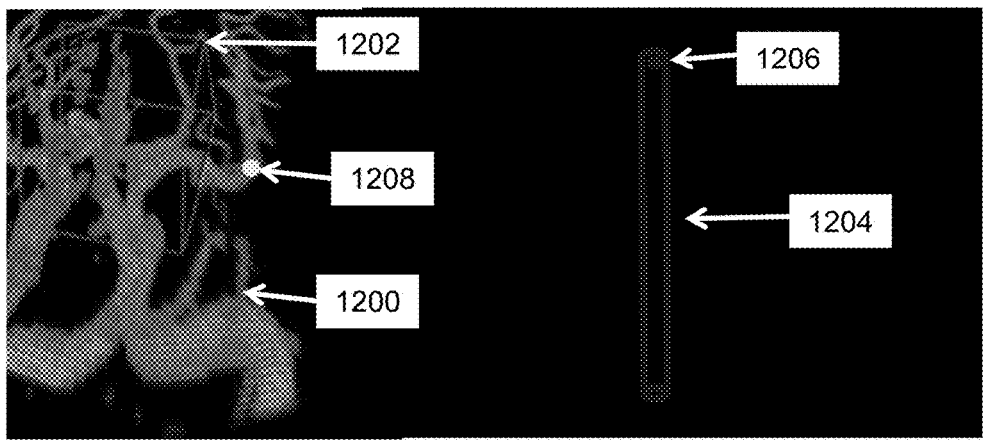
FIGS. 12A, 12B and 12C illustrate virtual pointers used to point to knowledge spots on virtual body structure to retrieve medical terminology and bodily functions need to add spots with text boxes of med terms and bodily functions.
Figure 12B:
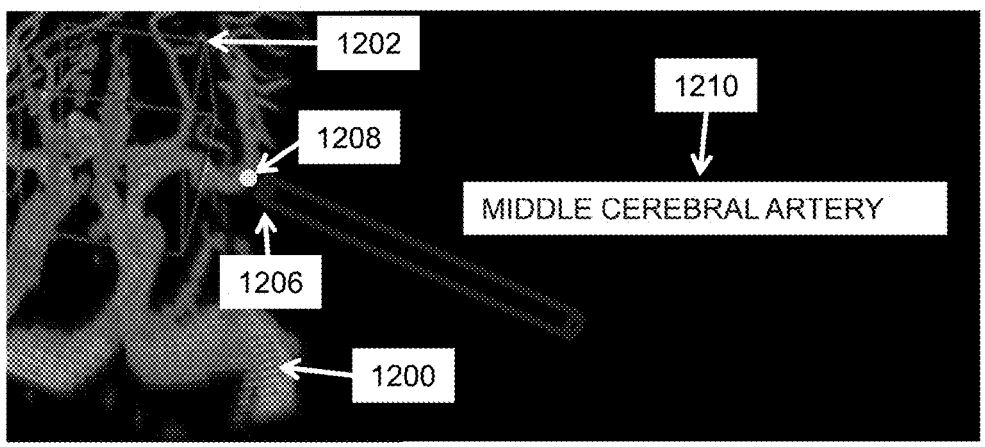
Figure 12C:
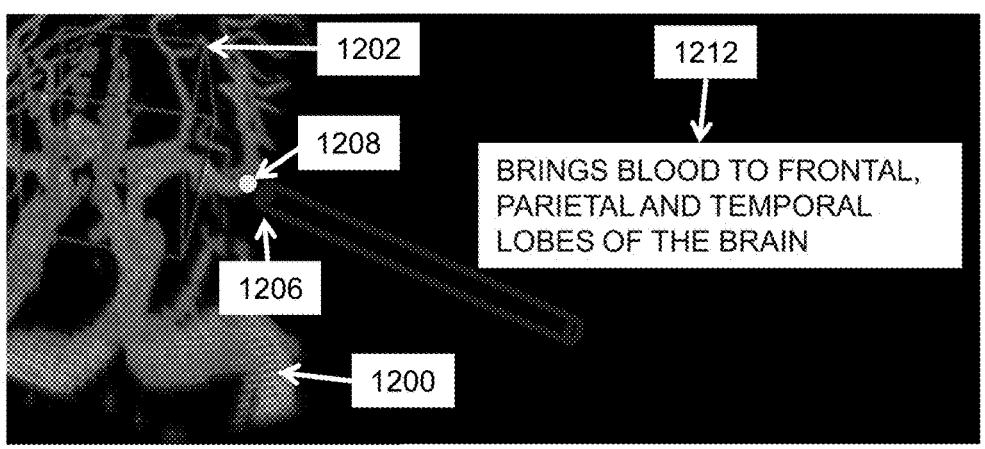

FIGS. 12A, 12B and 12C illustrate virtual pointers used to point to knowledge spots on virtual body structure to retrieve medical terminology and bodily functions need to add spots with text boxes of med terms and bodily functions. For game purposes the virtual pointers could be items selected by the person(s) playing the game such as, but not limited to pistol(s) with red dot(s); pointer with star at tip; laser pointer; movable check mark. The virtual pointer(s) could also interact with game displays such as marking which of the following multiple choices is correct. During preparation of the anatomy types of games, virtual knowledge spots would be added to the virtual 3D body structure (e.g., dots with numbers, letters, etc.). Associated with each of these knowledge spots would be a message containing the correct medical terminology for marked tissue. A separate control command could list the bodily functions of that particular part. During pathology types of games, anomalous types of tissue could be marked and when pointed to, information about the pathology would also be displayed. In FIG. 12A, the cerebral vasculature 1200, a 3D cursor 1202 and the virtual focal point pen 1204 with a geo-registered tip 1206 are shown. Note that the virtual focal point pen 1204 is initially positioned outside of the cerebral vasculature 1200. A knowledge spot 1208 is shown as a yellow dot. In a subsequent time step in FIG. 12B, the cerebral vasculature 1200, a 3D cursor 1202, the virtual focal point pen 1204 with a geo-registered tip 1206 and a knowledge spot 1208 are shown. Note that the position and orientation of the virtual focal point pen 1204 has changed and the geo-registered tip 1206 of the virtual vocal point pen 1204 is in close proximity to the knowledge spot 1208 in this time step. FIG. 12C illustrates an additional time step wherein the video game player could activate the knowledge spot to show a description of the anatomical structure. The cerebral vasculature 1200, a 3D cursor 1202 and the virtual focal point pen 1204 with a geo-registered tip 1206 are shown. Note that a visual pop up 1212 with the description of the knowledge spot as brings blood to frontal, parietal and temporal lobes of the brain is shown. Note for simplicity, this figure illustrates only a left eye image for each of FIG. 12A, FIG. 12B and FIG. 12C. In practice when wearing a head display unit (HDU), both a left and right eye image would be seen.

Figure 13A:
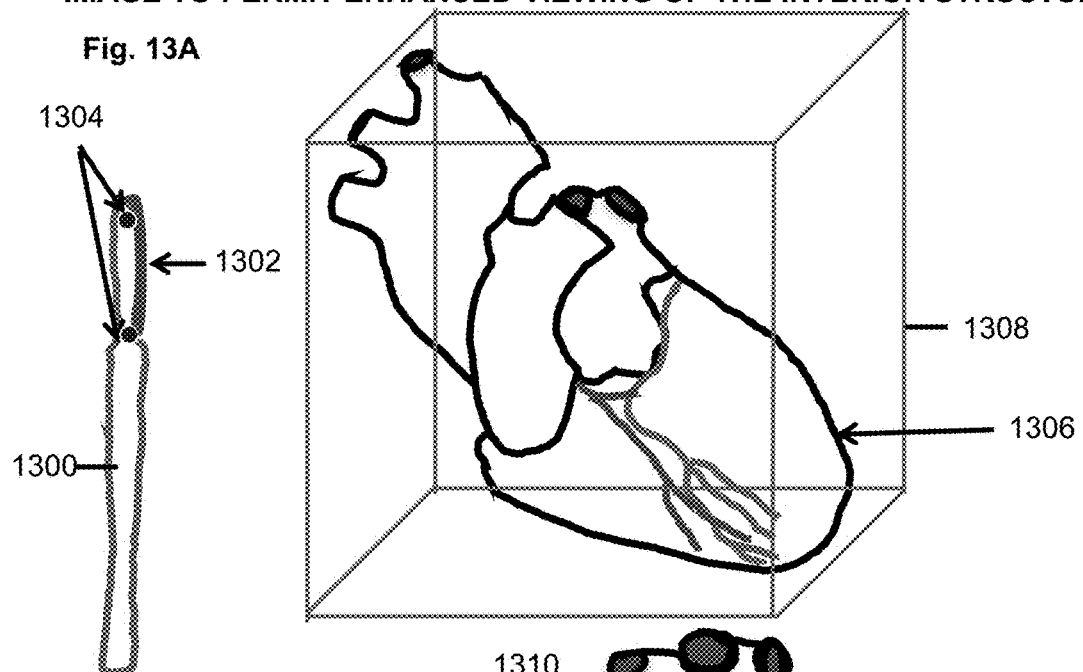
FIGS. 13A, 13B and 13C illustrate the virtual knife, which can be used by medical personnel to 'carve away tissue' from an existing 3D medical imaging volume to permit enhanced viewing of the interior structure.
Figure 13B:
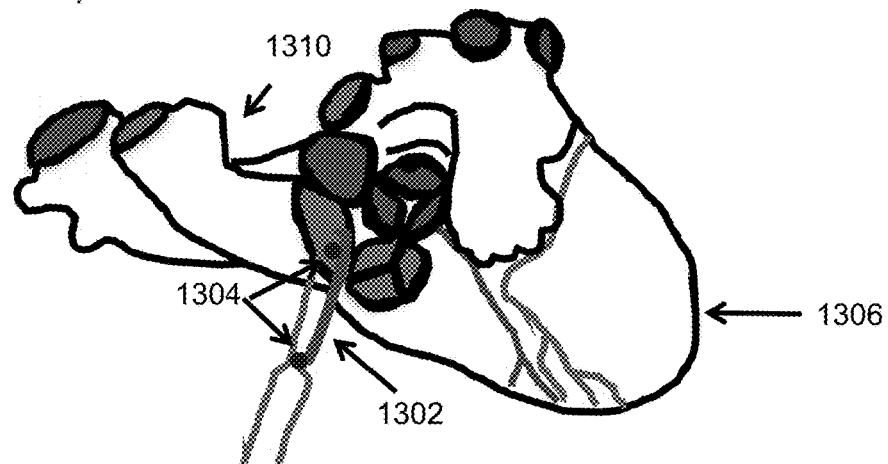
Figure 13C:

FIGS. 13A, 13B and 13C illustrate the virtual knife, which can be used by medical personnel to 'carve away tissue' from an existing 3D medical imaging volume to permit enhanced viewing of the interior structure. In this example, the virtual knife is used to investigate the patient's heart. This task is performed in conjunction with a 3D cursor encasing a 3D medical volume of the heart. FIG. 13A illustrates the virtual knife 1300 with a virtual cutting surface 1302 and associated registration point(s) 1304. The medical person viewing the medical images could: pick up the virtual knife 1300 and move it to the volume of interest shown as heart 1306 encased in a 3D cursor 1308 with tissue external to the heart subtracted. FIG. 13B illustrates passing the knife 1300 equipped with a cutting surface 1302 and registration points 804 through the 3D volume of interest 1306 such that a portion of the tissue 1310 (i.e., aorta and pulmonary artery) is cut and then displaced. FIG. 13C illustrates removal of the aorta and pulmonary artery to allow the medical personnel to peer into the aortic valve 1312 and pulmonary valve 1314. Further carving could allow inspection of the tricuspid valve (not shown). Finally, 4D datasets can be viewed in conjunction with the virtual tool kit to provide even more enhanced viewing of the heart.

FIGS. 14A, 14B and 14C illustrate a virtual ride through a virtual vascular tunnel with road sign for a person playing the game using a visual transport tool. The virtual transport tool is a means/pathway by which the person(s) playing the game(s) can move within a hollow structure and visualize the conditions therein. The virtual transport tool can be used alone or in conjunction with the virtual catheter to produce a 3D digital image of the interior of the vascular structure within the patient or to train the person(s) playing interventional surgery type of game how to treat vascular conditions. The virtual transport tool can provide a vision for the game player of what is ahead within the blood vessels. Blood within the blood vessel in the actual person's images could be digitally subtracted so that a hollow tunnel remains. The virtual transport tool allows the person(s) playing the game(s) to visualize the internal structure of the blood vessel. A virtual light could shine on the blood vessel walls for some distance forward of the current viewing point. When a narrowing of the tunnel and X, Y, Z coordinates of the constrictor be recorded for later documenting what was found in 'investigative' types of games. Typically, the virtual transport tool will be within the center of the blood vessel and looking ahead. Note that the center of the viewing point is within the center of the blood vessel, but the actual viewing perspectives would be offset in accordance with the left and right eye viewing perspectives. The person(s) playing the game(s) viewing the medical images could visualize what it looks like to travel within a blood vessel, as viewed from a 3D headset (e.g., augmented reality). Note that it is possible to expand the diameter of the virtual blood vessel to enhance viewing in accordance with voxel manipulations (See U.S. patent application Ser. No. 16/195,251). As an analogy, it may be difficult to look into a small pipe or difficult to simultaneously view all portions of a large tunnel from within; therefore, the ability to adjust the size of the tunnel offers great viewing flexibility. If the person(s) playing the game(s) identifies an anomalous condition, then the person(s) playing the game(s) could take a different positions and orientations to study the condition. The distance of the blood vessel displayed would be selected by the person(s) playing the game(s) and the lighting intensity of the structure would also be selected by the person(s) playing the game(s). A common clinical application anticipated through the use of these techniques includes mensuration of a carotid atherosclerotic plaque (e.g., measuring the lumen at the narrowed regions as well as the length of the narrowing, which may move be better metric for determining stent type and placement than current methods, such as the North American Symptomatic Carotid Endarterectomy Trial (NASCET) measurement technique). As an example, a small volume within the lumen over a specified length would be a better indicator for disease state and intervention as compared to current methods. A rolling computation of the lumen of each vessel would be performed with metrics provided to the medical professional. For example, this ride could be used during an assessment of the vascular structure and potential need for insertion of stents. At any time, the person(s) playing the game(s) viewing the medical images could view the vascular structure as a whole with current location of the ride in the blood vessel shown via the icon. FIG. 14A illustrates a normal blood vessel interior surface with blood deleted 1400 without plaque. This largest circle 1400 represents the inner aspect of the blood vessel at the current viewing location. The texture of the inner mucosal surface 1401 is shown. The middle sized square dot circle 1402 represents the inner aspect of the blood vessel at an intermediate distance from the current viewing location, such as 5 cm from the current viewing location. The smallest round dot circle 1404 represents the farthest distance that the user could see from the current viewing location. A virtual marker, for example, the double-headed arrow 1406 could indicate the length within the blood vessel actively being viewed, such as 10 cm from the current position of the blood vessel 1400 to the farthest position within the blood vessel that can be seen 1404. A virtual road sign 1408 with distance to key intersection, such as "30.0 cm to brachiocephalic artery". FIG. 14B illustrates narrowing of the blood vessel lumen due to atherosclerotic plaque and a road sign providing a description of a measurement. This largest circle 1410 represents the inner aspect of the blood vessel at the current viewing location. The texture of the inner mucosal surface 1411 is shown. The middle sized square dot circle 1412 represents the inner aspect of the blood vessel at an intermediate distance from the current viewing location, such as 5 cm from the current viewing location. Note that a portion of the middle circle 1412 at the 2 o'clock location is shown to bulge inward 1416. Both the round portion of the middle circle 1412 and the portion of the middle circle that bulges inward 916 are located at 5 cm from the current viewing location. Thus, the entirety of the dotted line including 1412 and 1416 is located at 5 cm from the current viewing location; thus, it represents an "isodistance line". The smallest round dot circle 914 represents the farthest distance that the user could see from the current viewing location, such as 10 cm from the current viewing location. A virtual marker, for example, the large double-headed arrow 1418 could indicate the length within the blood vessel actively being viewed, such as 10 cm from the current position of the blood vessel 1410 to the farthest position within the blood vessel that can be seen 1414. A smaller double-headed arrow 1420 is shown from the expected position of the dotted line (demarcating the 5 cm distance away assuming no plaque/narrowing) to the actual position that is 5 cm away and is more inwardly located 916. Please note that when the radius of a particular "isodistance line" decreases, this would indicate an area of narrowing. Please note that when the radius of a particular "isodense line" increases, this would indicate an area of expansion/ectasia/aneurysm. Also, note another virtual road sign 1420 stating "5.0 cm away from a 30% atherosclerotic narrowing centered at 2 o'clock". The clock system is one example of how the location of the narrowing can be described. FIG. 14C illustrates the visual transport tool approaching a branching juncture of three blood vessels. During pre-panning, the medical professional could select which of the blood vessels the catheter should enter and this blood vessel could be highlighted in false color for verification of the correct path for the catheter. The largest circle 1422 represents the inner aspect of the blood vessel at the current viewing location. The texture of the inner mucosal surface 1423 is shown. A medium sized half circle at the 3 o'clock position 1424 represents a branch vessel (e.g., internal carotid artery), which would be the desired option to travel into. A medium sized half circle at the 9 o'clock position 926 represents an additional branch vessel (e.g., external carotid artery) would be a second option to travel into, but not desired in this example scenario. A dotted red line 1428 is illustrated as an example of a virtual tool to be displayed over the image as a visual cue to help notify the medical personnel of the branch that they are desiring to enter. A virtual road sign 1430 is illustrated, which states "5.0 cm away from the carotid bifurcation. Head towards 3 o'clock to enter the internal carotid artery."

FIGS. 15A, 15B, and 15C illustrate the virtual catheter, which could be used in conjunction with a volumetric medical image of the vascular structure within the patient with the assistance of virtual icons. For example, the 3D virtual catheter could be used during pre-operative planning of an interventional operation, such as acquiring important distance or angle measurements. In this figure, an interventional procedure a 3D virtual catheter is used in treatment of an aneurysm. FIG. 15A shows the solid blue line 1500 as the catheter located in the right groin region entering at the common femoral artery and extending into the right external iliac artery and to the aorta. The tip of the catheter 1502 is a small black solid circle. Note that path that has been traversed is shown as a solid lines and the planned path is shown in hashed line 1504. The planned routes can be implemented via placement of location markers in a particular blood vessel that the medical professional wants to target. Such location markers can be at way points along the desired paths or at the final target lesion 1506 (e.g., brain aneurysm). After these location markers are placed, the path connecting the markers can be marked (e.g., blue dotted line). Then measurements along the blue dotted line can be performed. With measurements, a road sign 1508 can be displayed to inform medical personnel of the distance to the vascular junction to be used in an actual interventional medical procedure. Please note that a virtual icon 1510 is also shown, such as a 2D or 3D object. FIG. 15B shows virtual catheter 1512 extending into the thoracic aorta. As shown, the dashed line 1016 represents the desired pathway of the catheter, which is through the brachiocephalic artery, then the common carotid artery, then the internal carotid artery then the middle cerebral artery, and finally into the aneurysm 1518. A road sign can be displayed to inform the medical personnel of the distance to the vascular junction to be used in an actual interventional medical procedure. Augmented reality distance markers could be added to the 3D virtual catheter for each intersection the interventionalist would need to take care and be prepared to change from one blood vessel to another. Screen captures of all key vascular junctures could be annotated angular changes from current path in coordinate system X-Y, X-Z and Y-Z planes. FIG. 15C shows a blow-up of a vascular junction wherein multiple path options occur and the medical personnel must take care in moving the catheter to the correct blood vessel. The descending thoracic aorta 1522, brachiocephalic artery 1524, left common carotid artery 1526, left subclavian artery 1528 and ascending thoracic aorta 1530 are shown. The virtual catheter 1532 is shown. The tip of the virtual catheter 1534 is shown. The blue dotted line 1536 represents the desired catheter path.

FIGS. 16A, 16B and 16C illustrate the general concept of 3D medical images and example techniques behind the explosion of 3D medical images into multi separate organs, which can then be individually selected by person playing the game. The person playing the game viewing the medical images (e.g., using segmentation techniques outlined in U.S. patent application Ser. No. 15/904,092, which is incorporated by reference) could divide the 3D digital volume of interest into multiple parts based on their common characteristics (e.g., similar Hounsfield units, anatomical atlas, etc.). The general process is illustrated in this figure wherein the desire is to examine key organs individually. Such a process could be structured, for example, in accordance with items on an image review checklist. FIG. 16A illustrates a generalized illustration of organs within the abdomen. The liver 1600, right adrenal gland 1602, right kidney 1604, inferior vena cava 1606, right iliac vein 1608, spleen 1610, aorta 1612, pancreas 1614, left adrenal gland 1616, left kidney 1618, gastrointestinal tract 1620 and left iliac artery 1622 are shown. The process would be to expand these organs outward in X, Y, Z directions from an approximate center point in the torso to facilitate the individual inspection without visual interference from adjacent organs. FIG. 16B illustrates the organs after segmentation has been applied, noting dashed lines around the organs to illustrate the segmentation process. The liver 1624, right adrenal gland 1626, right kidney 1628, inferior vena cava 1630, right iliac vein 1632, spleen 1634, aorta 1636, pancreas 1638, left adrenal gland 1640, left kidney 1642, gastrointestinal tract 1644 and left iliac artery 1646 are shown. Note that a dashed line is shown to better show the segmentation. FIG. 16C shows the exploded view. The coordinates (X, Y, Z) of the organs would be modified to new positions indicated by the dashed lines. The software for implementation of the concept is, but not limited to, the following procedures. The medical person viewing the medical images could select a point within the 3D digital volume (ideally near the center of the 3D digital volume and between segmented sub-volumes), which would act at the origin point for the explosion. The liver 1648, right adrenal gland 1650, right kidney 1652, inferior vena cava and iliac veins 1654, pancreas 1656, gastrointestinal tract 1658, spleen 1660, left kidney 1662, left adrenal gland 1664 and aorta and iliac arteries 1666. FIG. 16D illustrates one of multiple ways the sub-volumes of the 3D digital can be separated as if an explosion occurred. One of the ways, but not limited to, is as follows: create eight large cubes 1668 each touching the center point and each parallel to the X, Y, Z axes (e.g., the first cube would be positive in X, positive in Y and positive in Z; the second cube could be positive in X, negative in Y and positive in Z; and so on). Then the medical person viewing the medical images establishes a distance factor for sub-volumes close to the center point, a larger distance factor for those further away. Then these factors are applied to all voxels within each specific sub-volume of the 3D digital image based on which cube the center voxel of the sub-volume was in. (Note that for the first cube mentioned above, for all sub-volumes whose center voxel fell in this cube the X, Y, Z coordinates of voxels within that sub-volume would increase by the specified factor in the positive X, positive Y and positive Z direction. For sub-volumes in the second cube the increases would be in positive X, negative Y and positive Z directions). The video game player viewing the medical images modify the factors changing the spread between the sub-volumes during the course of the examination. For example, a moderate spread is shown 1670. Alternatively, a larger spread is shown 1672. The person(s) playing the game(s) could modify the factors changing the spread between the sub-volumes during the course of the game.

Figure 17A:
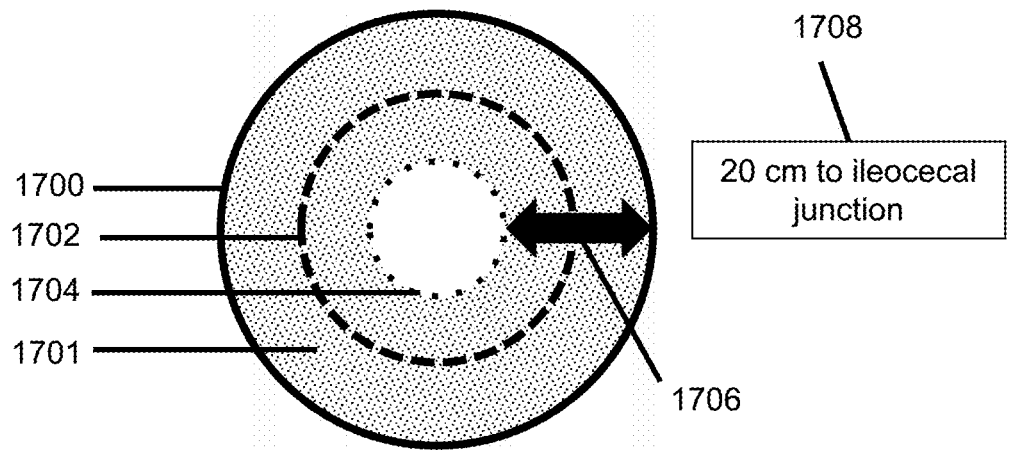
FIGS. 17A and 17B illustrate use of virtual transport viewer to perform a more accurate virtual colonography review.
Figure 17B:
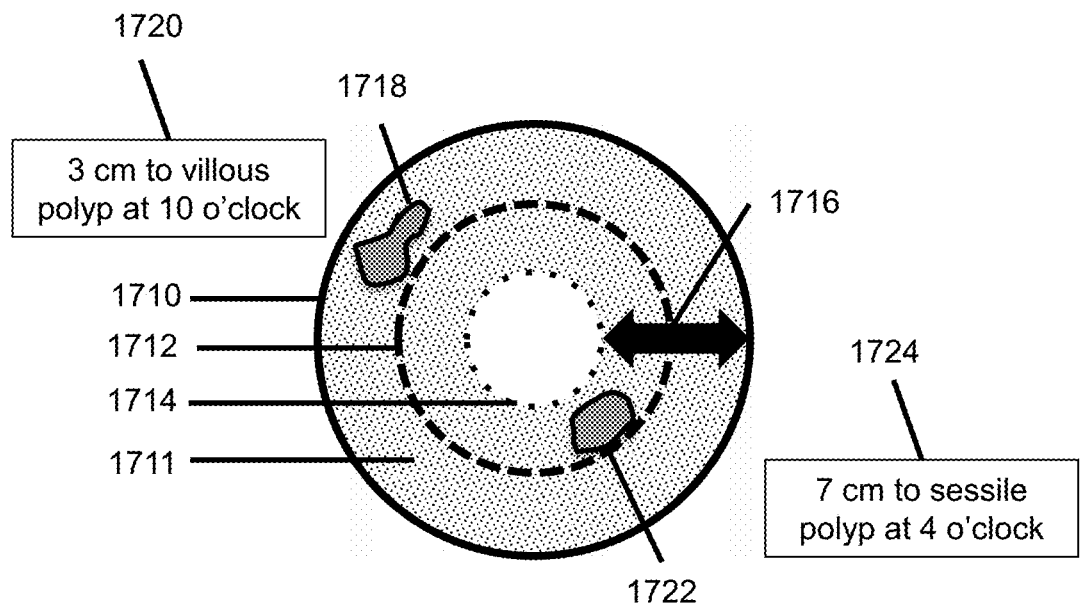

FIGS. 17A and 17B illustrate use of virtual transport viewer to perform a more accurate virtual colonography review. In this figure the virtual transport viewer is employed to view the inside of the colon and determine if polyps are present. If none are present, all is fine and the person(s) playing the game(s) can give the patient a clean bill of health. If polyps are present, they can be detected by the person(s) playing the game(s) using the virtual transport viewer and, then subsequent treatment can be pursued using interventional surgery type game procedures. The actual patient data would involve a CT scan of the colon; a 3D volume of the colon would be created from the CT 2D slices (See U.S. Pat. No. 8,384,771) during game preparation. The person(s) playing the game(s) segmentation (See U.S. patent application Ser. No. 15/904,092) to isolate the colon and digital subtraction to extract the contents of the colon (e.g., air, excrement). In so doing the colon would maintain its original shape; then the person(s) playing the game(s) could use the virtual transport to examine back and forth and side to side within the colon to find polyps. There is a tendency among the general populace to avoid having a colonoscopy due to unpleasant preparation (e.g., large volume of liquid to drink) and uncomfortable period during the procedure. One of the alternatives is to go through a virtual colonography, wherein a CT scan is performed, and the inner mucosal surfaces of the colon is reviewed. If no polyps are found, a treatment phase is not necessary. If, however, polyps are found, then at some later date, the preparation phase is repeated and a treatment phase (i.e., colonoscopy) is performed to remove the polyps. In this figure the virtual transport viewer is employed to view the inside of the colon and determine if polyps are present. If none are present, all is fine and a preparation for colonoscopy is not needed. If polyps are present, they can be detected by the virtual transport viewer and, then the required preparation and subsequent treatment can be pursued. Under the virtual transport viewer process, the patient would follow a process in which he/she would: first receive a CT scan of the colon; a 3D volume of the colon would be created from the CT 2D slices (U.S. Pat. No. 8,384,771, which is incorporated by reference); segmentation (U.S. patent application Ser. No. 15/904,092, which is incorporated by reference) would identify the colon and subtraction would extract the contents of the colon (e.g., air, excrement). In so doing the colon would maintain its original shape; then the virtual transport could be inserted and enable examination back and forth and side to side within the colon. This manner of examination avoids the problem of polyps being occluded by folds which can happen during insertion of the forward looking only camera. If no polyps were found, the patient could go home confident of continued good health and he/she would have avoided the unpleasantness and discomfort of the preparation phase and colonoscopy or preparation plus air insertion phase. FIG. 17A illustrates the view of the interior surface of the colon with the air and stool deleted without a polyp. This largest circle 1700 represents the inner aspect of the colon at the current viewing location. The texture of the inner mucosal surface 1701 is shown. The middle sized square dot circle 1702 represents the inner aspect of the colon at an intermediate distance from the current viewing location, such as 5 cm from the current viewing location. The smallest round dot circle 1704 represents the farthest distance that the user could see from the current viewing location. A virtual marker, for example, the double-headed arrow 1706 could indicate the length within the blood vessel actively being viewed, such as 10 cm from the current position of the blood vessel 1700 to the farthest position within the blood vessel that can be seen 1204. A virtual road sign 1708 with distance to key intersection, such as "20 cm to ileocecal junction". FIG. 17B illustrates the view of the interior surface of the colon with the air and stool deleted with three polyps. This largest circle 1710 represents the inner aspect of the colon at the current viewing location. The texture of the inner mucosal surface 1711 is shown. The middle sized square dot circle 1712 represents the inner aspect of the colon at an intermediate distance from the current viewing location, such as 5 cm from the current viewing location. The smallest round dot circle 1714 represents the farthest distance that the user could see from the current viewing location. A virtual marker, for example, the double-headed arrow 1716 could indicate the length within the blood vessel actively being viewed, such as 10 cm from the current position of the blood vessel 1710 to the farthest position within the blood vessel that can be seen 1714. A villous polyp 1718 is illustrated. A virtual road sign 1720 with distance to key landmark is shown, such as "3 cm to villous polyp at 10 o'clock". A sessile polyp 1722 is shown. A virtual road sign 1724 with distance to key landmark is shown, such as "7 cm to sessile polyp at 4 o'clock".

Figure 18:
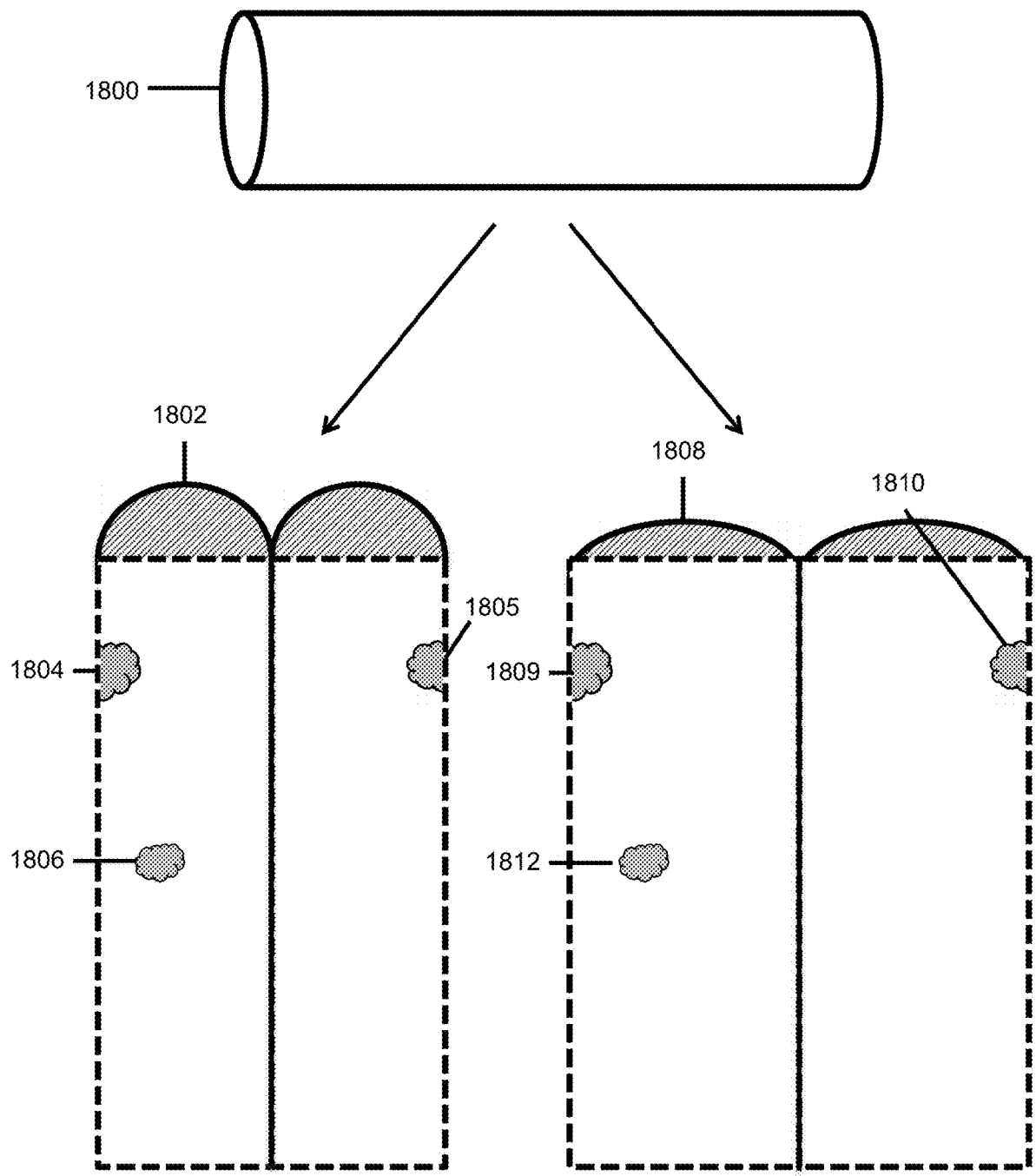
FIG. 18 illustrates a portion of a virtual 3D volumetric medical image which contains the large intestine which has through voxel manipulation, been split and stretched in such a manner so that it is one long straight tube sliced lengthwise.

FIG. 18 illustrates a portion of a virtual 3D volumetric medical image which contains the large intestine which has through voxel manipulation, been split and stretched in such a manner so that it is one long straight tube sliced lengthwise. The person(s) playing the game(s) can, through voxel manipulation, stretch the colon in such a manner so that it can become one long straight tube. And then, the contents within the tube can be segmented and subsequently/eliminated from the tube. And, finally, the person(s) playing the game(s) can split the tube along the length axis and opened to permit viewing of the internal structure. In preparation for this game, a CT image with/without contrast is performed. Then a 3D virtual image is constructed from the CT 2D slices (See U.S. Pat. No. 8,384,771). The person(s) playing the game(s) could invoke segmentation (See U.S. patent application Ser. No. 15/904,092) and subtract tissue external to the colon. Also, the non-tissue contents within the colon could be subtracted by the person(s) playing the game(s). Then the colon is 'stretched' so that folds which can obscure polyps are elongated and, thereby, obscuration of polyps by folded colon tissue is eliminated. This stretching process involves voxel manipulation as described in U.S. patent application Ser. No. 16/195,251. This elongated, straight virtual colon is split in 2 along the length axis so that the internal structure can be viewed by the person(s) playing the game(s) via the head display unit, as illustrated in this figure. And then, the contents within the tube have segmented and subsequently/eliminated from the tube. And, finally, the tube is split along the length axis and opened to permit viewing of the internal structure. There are methods to physically examine the internal structure of the colon which involve: preparation, insertion of air to fill and expand the colon, insertion of a camera with light and movement of this system along the length of the colon to observe and record the internal structure. Subsequently, a rendered TV recording can be presented to medical personnel and patient. A limitation of the rendered TV recording is that polyps can be occluded from the TV view by folds along the colon. Further, if polyps are found, the patient must return at a later date for a colonoscopy which entails another preparation and subsequent removal of polyp tissue. The process invoked in this virtual process does not require the unpleasant preparation phase in the preliminary examination. In this process a CT image with/without contrast is performed. Then a 3D virtual image is constructed from the CT 2D slices (U.S. Pat. No. 8,384,771, which is incorporated by reference). Segmentation (U.S. patent application Ser. No. 15/904,092) is performed and tissue subtracted external to the colon. Also, the non-tissue contents within the colon are subtracted. Then the colon is 'stretched' so that folds which can obscure polyps are elongated and, thereby, obscuration of polyps by folded colon tissue is eliminated. This stretching process involves voxel manipulation as described in U.S. patent application Ser. No. 16/195,251. This elongated, straight virtual colon is split in 2 along the length axis so that the internal structure can be viewed via the head display unit as illustrated in this figure. The hollow viscus colon 1800 is straightened. After straightening, the colon can be opened up like a book 1802 and viewed from the top looking inside at the mucosal surface. Once opened, a first polyp is shown cut in half with a first half 1804 and a second half 1805. A second polyp is shown intact 1806. Alternatively, the colon can be opened up like a book and pulled apart to flatten it out 1808 and viewed from the top looking inside at the mucosal surface. Once opened, a first polyp is shown cut in half with a first half 1809 and a second half 1810. A second polyp is shown intact 1812. When the colon is flattened, a polyp will pop out more with 3D viewing on a headset.

Figure 19:
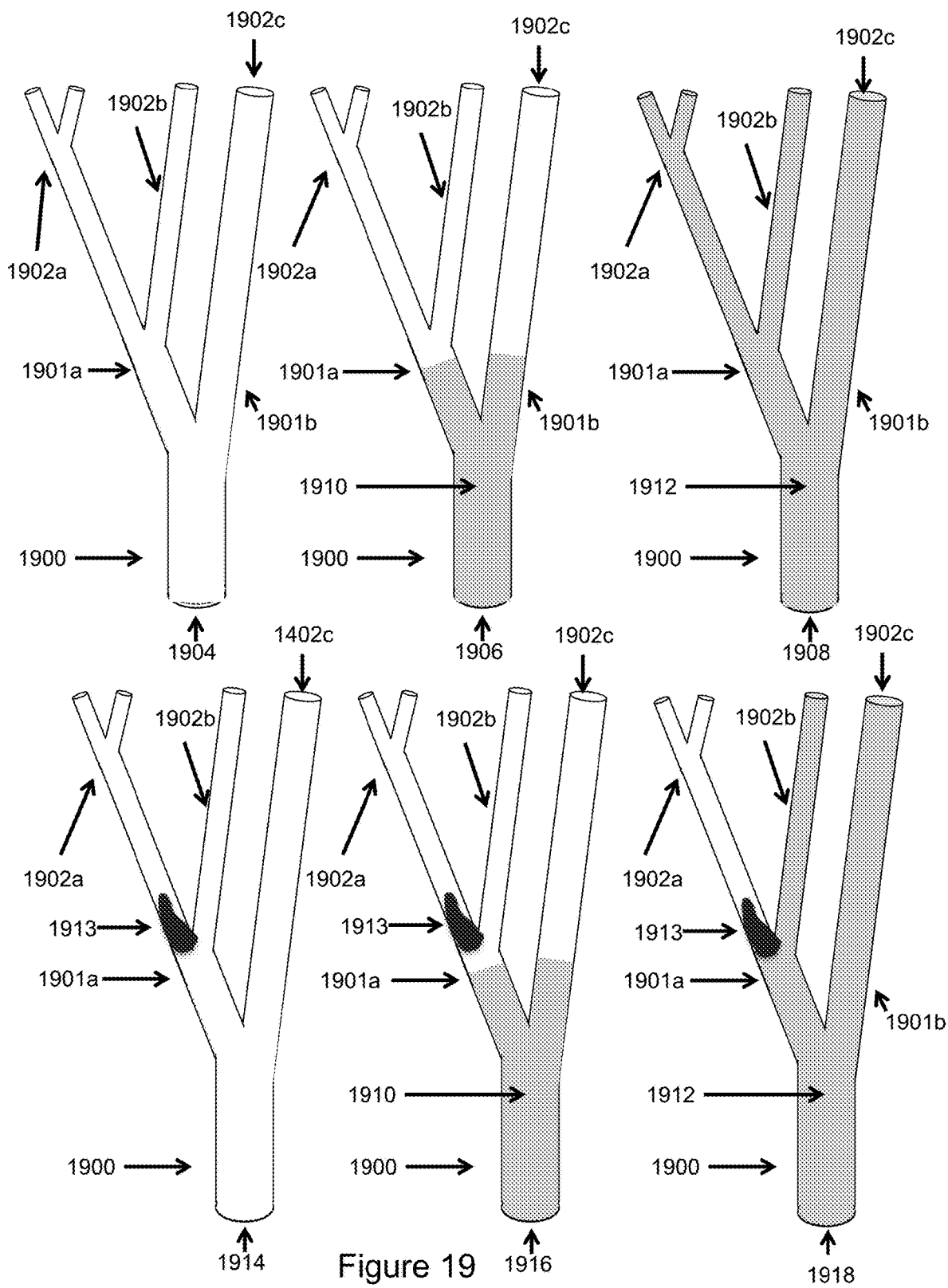
FIG. 19 illustrates the removal of blood within the selected vascular structure and then insertion of virtual contrast into the vascular structure through voxel creation followed by an example of interactive-type voxels.

FIG. 19 illustrates the removal of blood within the selected vascular structure and then insertion of virtual contrast into the vascular structure through voxel creation followed by an example of interactive-type voxels. First is the removal of blood within the selected vascular structure and then insertion of virtual contrast into the vascular structure through voxel creation followed by an example of interactive-type voxels. Initially, the person(s) playing the game(s) could remove blood within the vascular system. In the top row, the blood vessels are illustrated in their native state. In the bottom row, blood clot is present, would be assigned a blockage-type interactive voxel parameter during game preparation. In this illustration, the person(s) playing the game(s) inserts virtual contrast and tracks it's progress through the blood vessels over time. Virtual contrast progress over time is shown in the normal setting of a blood vessel and in the altered setting of a blood vessel (i.e., with a blood clot). Note that the virtual contrast can progress from proximal to distal up to the point of the clot, but not beyond the clot. The remaining branches experience the insertion of virtual contrast. Thus, assigning a blockage-type interactive voxel parameter stops flow of virtual contrast. Thus, the person(s) playing the game(s) could identify the clot location. This could phase 1 of a multi-phase game wherein the next phase would be removal of the clot through interventional surgery type game. Initially, the blood within the affected vessels has been removed. In the top row, the blood vessels are in their normal, non-pathologic state and normal blood flow is illustrated through the placement of virtual contrast. The proximal portion of the blood vessel 1900, mid portions of the blood vessel 1901*a* and 1901*b* and distal portions of the blood vessel 1902*a*, 1902*b* and 1902*c* are shown. Thus, when virtual contrast is inserted, it would mimic normal blood flow where it to be imaged. Three time points are shown including: an initial time point 1904; a subsequent time point 1906; and, a final time point 1908. At the initial time point 1904, all of the native blood voxels have been removed and no virtual contrast has been inserted.

At the subsequent time point 1906, some virtual contrast 1910 shown in gray has been inserted into the proximal portion of the blood vessel 1900 and mid portions of the blood vessel 1901*a* and 1901*b*, but no virtual contrast (the lack of virtual contrast is displayed in white) has been inserted into the distal portions of the blood vessel 1902*a*, 1902*b* and 1902*c*. At the final time point 1908, virtual contrast 1912 shown in gray has been inserted into the proximal portion of the blood vessel 1900, mid portions of the blood vessel 1901*a* and 1901*b*, and distal portions of the blood vessel 1902*a*, 1902*b* and 1902*c*. In the bottom row, the blood vessels are in a pathologic state (i.e., a blood clot 1913 is lodged into one of the distal artery branches). The proximal portion of the blood vessel 1900, mid portion of the blood vessel 1901*a* and 1901*b* and distal portions of the blood vessel 1902*a*,1902*b* and 1902*c* are again shown. Thus, since a blood clot 1913 is present, when virtual contrast is inserted, the virtual contrast would mimic an altered blood flow pattern. Three time points are shown including: an initial time point 1914; a subsequent time point 1916; and, a final time point 1918. At the initial time point 1914, all of the native blood voxels have been removed and no virtual contrast has been inserted. At the subsequent time point 1916, some virtual contrast 1910 shown in gray has been inserted into the proximal portion of the blood vessel 1400 and mid portions of the blood vessel 1901*a* and 1901*b*, but no virtual contrast (the lack of virtual contrast is displayed in white) has been inserted into the distal portions of the blood vessel 1902*a*, 1902*b* and 1902*c*. At the final time point 1918, virtual contrast 1912 shown in gray has been inserted into the proximal portion of the blood vessel 1900, mid portions of the blood vessel 1901*a* and 1901*b*, and two of the distal branches of the blood vessels 1902*b* and 1902*c*; however, one of the distal portion of the blood vessel 1902*a* does not fill with virtual contrast 1912 because it is blocked by a blood clot 1913. Thus, when blood clot is present, which is assigned a blockage-type interactive voxel parameter. In this illustration, insertion of virtual contrast is shown in the normal setting of a blood vessel and in the altered setting of a blood vessel (i.e., with a blood clot). Note that the virtual contrast can progress from proximal to distal up to the point of the clot, but not beyond the clot. The remaining branches experience the insertion of virtual contrast. Thus, assigning a blockage-type interactive voxel parameter stops flow of virtual contrast. Alternatively, a surgical clip blockage-type interactive voxel parameter can be used.

Figure 20:
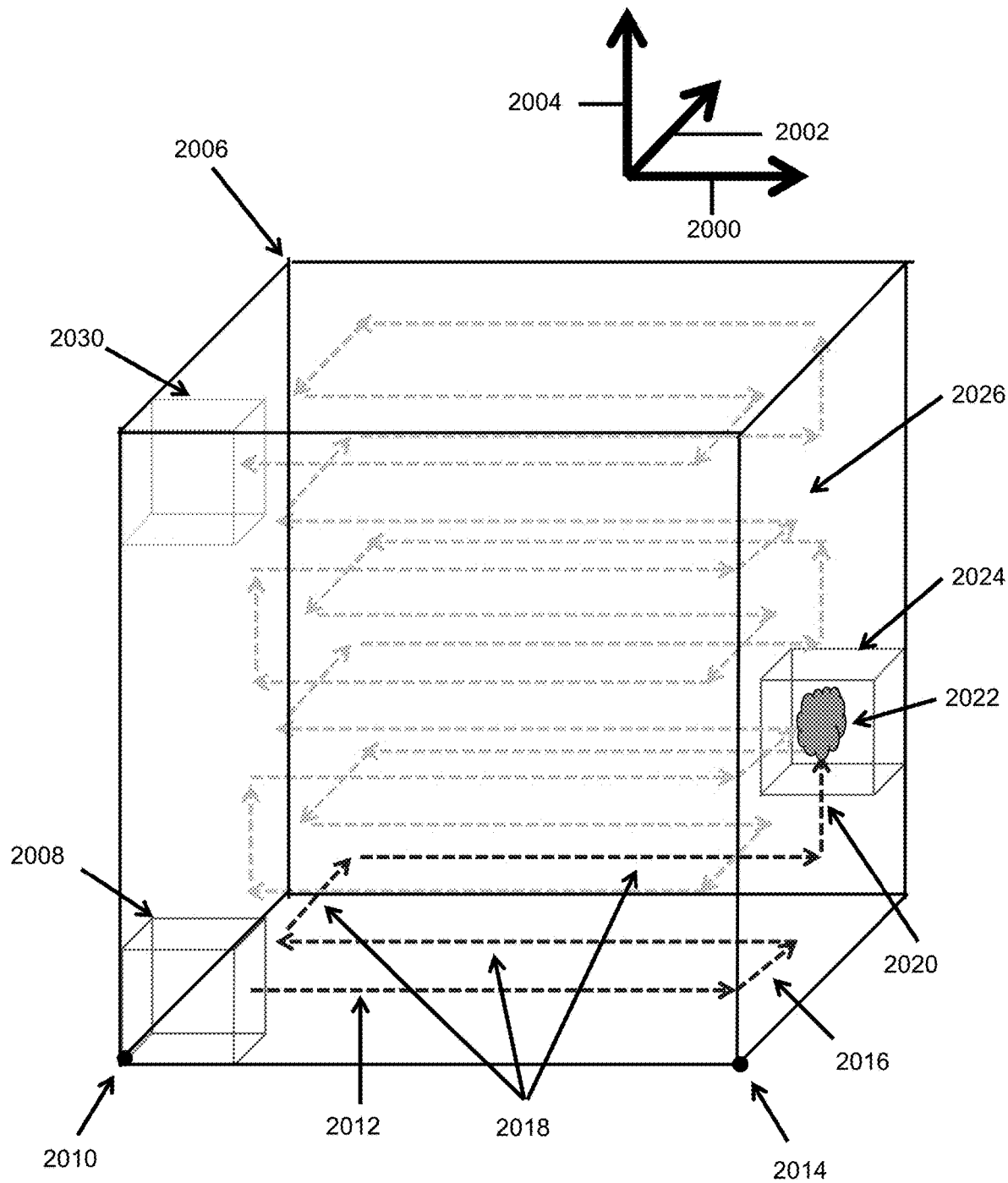
FIG. 20 illustrates an example of a systematic pattern of viewing of medical images (e.g., sequential virtual windshield wiper type pattern).

FIG. 20 illustrates an example of a systematic pattern of viewing of medical images (e.g., sequential virtual windshield wiper type pattern). This type of search would be ideal in investigative types of games wherein detection co cancer in early stages would be the game objective. See X, Y, Z coordinate system. A virtual windshield wiper can have several implementations. In the one shown, the pattern is to sequentially increase the X coordinate while holding the Y and Z coordinates at 0. When the max value for the X coordinate is reached, the y coordinate is increase to 1 and the X coordinate is sequentially decreased until the min X coordinate is reached, then Y coordinate is again incremented. When this plain has been completed, the Z coordinate is incremented. And so on until the entire volume of interest has been searched. In this figure a partially completed search is depicted. A variation of the windshield pattern is a 'fly back' wherein after the first row is completed, the pattern resumes with incrementing Y coordinate and then resuming incrementing the X coordinate. This type of search pattern helps ensure a thorough examination has been performed. This search patterns employ a 3D cursor (U.S. Pat. No. 9,980,691 and U.S. patent application Ser. No. 15/878,463). Note: when reviewing medical images in the original 2D format, the eyes jump from one spot to another following the reviewing individual's saccadian path and substantial portions of a slice may not be observed and, consequently, small masses may be missed. In the use of the 3D cursor, these small masses subtend a larger fraction of presented image and the probability of detection increases proportionally. The x-direction 2000, y-direction 2002 and z-direction 2004 are shown. The total imaging volume 2006 is shown. A virtual windshield wiper can have several implementations with the cursor moving in multiple systematic fashions. As illustrated, a first sub-volume 2008 being examined in the 3D cursor at the initial time point where one of the coordinates of the 3D cursor has one corner at position (0, 0, 0) 2010 is shown. The 3D cursor first moves in a fashion wherein the x-direction is increased 2012 and the y-coordinates and z-coordinates of the 3D cursor are unchanged as illustrated by the dashed arrow and the sub-volumes along this movement direction can be optimized. Thus, the pattern is to sequentially increase the X coordinate while holding the Y and Z coordinates constant. Once the corner of the 3D cursor reaches a maximum x-value of the total imaging volume 2006, then the 3D cursor is moved in a fashion wherein the y-direction is increased 2016 and the x-coordinates and z-coordinates of the 3D cursor are unchanged, as illustrated by the dashed arrow and the sub-volumes along this movement direction can be optimized. Thus, when the max value for the X coordinate is reached, the y coordinate is increased an increment and the X coordinate is sequentially decreased until the min X coordinate is reached, then Y coordinate is again incremented. This process of moving the 3D cursor in the x-direction 2000 and y-direction 2002 is then repeated 2018 until at which point a bottom layer of the total imaging volume 2006 has been fully examined by the 3D cursor. When this plain has been completed, the Z coordinate is incremented. The 3D cursor can be shifted 2020 upwards in the z-direction 2004. Note that during this systematic search pattern, an abnormality 2022 may be discovered at a particular 3D cursor position 2024. Such an abnormality can be placed in to a virtual bucket or virtual 3D virtual movable table for further analysis. Multiple additional systematic movements of the 3D cursor through the total imaging volume 2006 can be performed as illustrated 2026 until at which point the all sub-volumes within the total imaging volume have been examined and the 3D cursor reaches its final spot 2028. A variation of the windshield pattern is a 'fly back' wherein after the first row is completed, the pattern resumes with incrementing Y coordinate and then resuming incrementing the X coordinate. This type of search pattern helps ensure a thorough examination has been performed. This search patterns employ a 3D cursor (U.S. Pat. No. 9,980,691 and U.S. patent application Ser. No. 15/878,463). Note: when reviewing medical images in the original 2D format, the eyes jump from one spot to another following the reviewing individual's saccadian path and substantial portions of a slice may not be observed and, consequently, small masses may be missed. In the use of the 3D cursor, these small masses subtend a larger fraction of presented image and the probability of detection increases proportionally. In some implementations, sub-volumes are displayed to the medical personnel in an automated pattern, which includes, but is not limited to, the following: windshield wiper pattern or layer-by-layer pattern. An automated search pattern through the volume of interest may prove to increase the probability of detection. In this illustration, an automated search pattern is shown as the 3D cursor moves through the volume of interest. Note that a mass is identified in a later sub-volume. Future automated search pattern through the volume of interest is performed back and forth in each layer (similar to a windshield wiper) and then back and forth in the next layer.

Figure 21A:
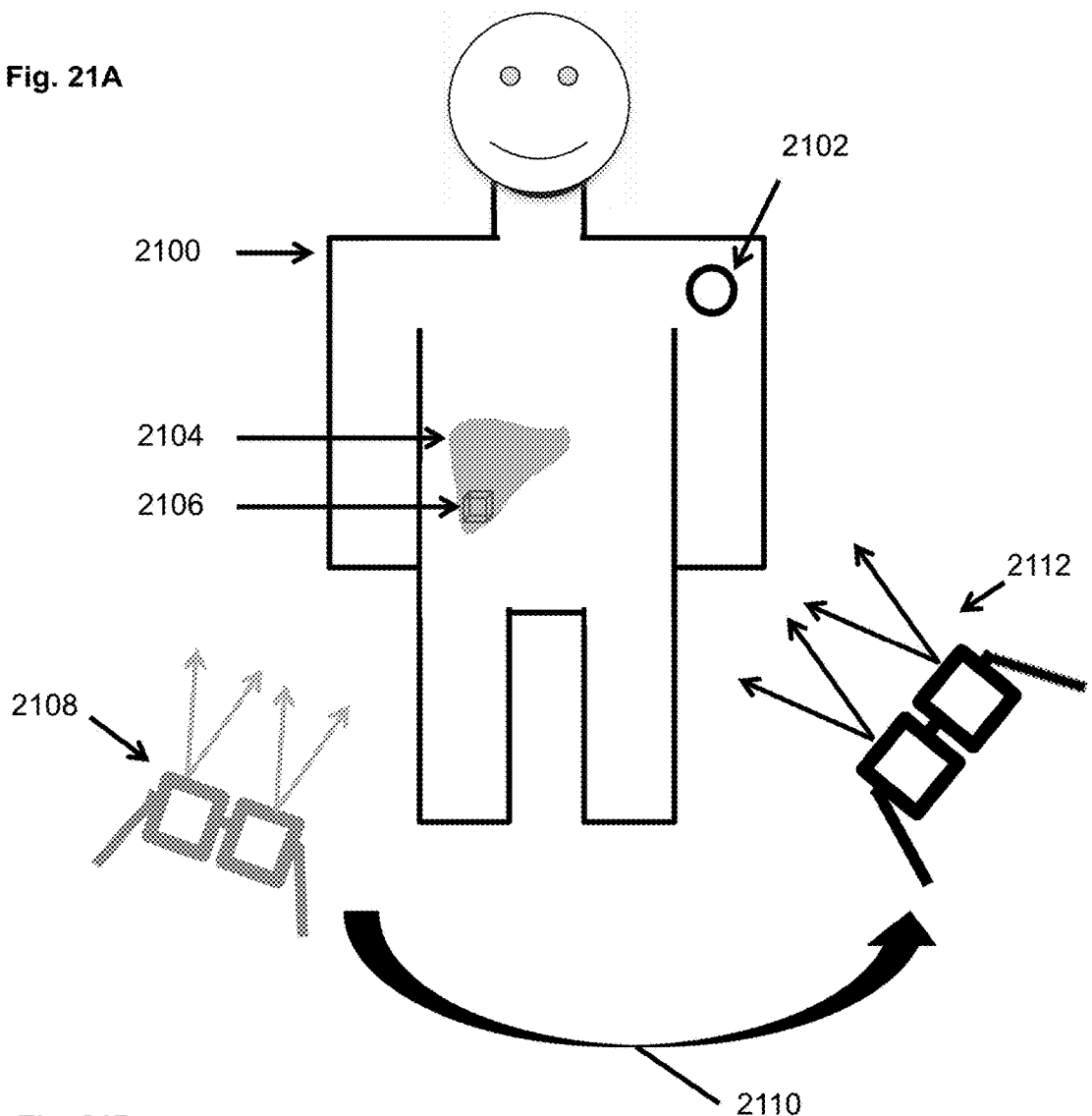
FIGS. 21A and 21B illustrate an icon of a human with the location of the 3D virtual cursor included at the approximate location within the body.
Figure 21B:
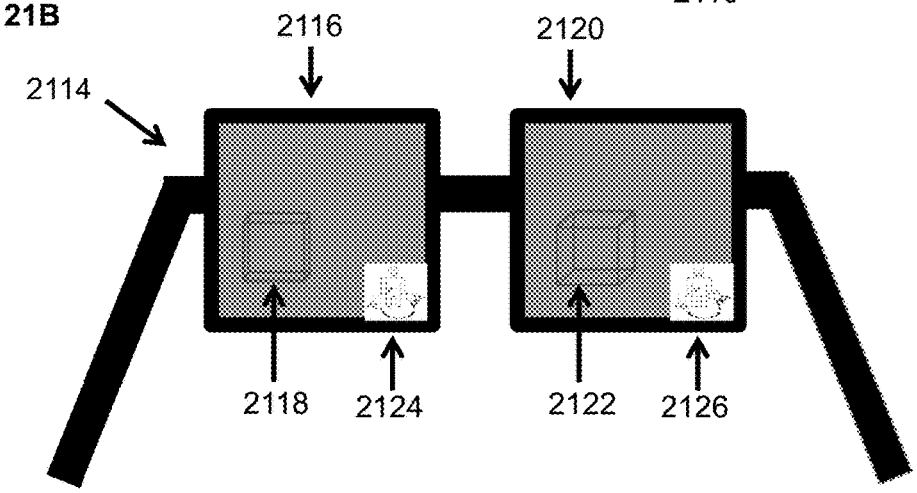

FIGS. 21A and 21B illustrate an icon of a human with the location of the 3D virtual cursor included at the approximate location within the body. This icon could be used the person(s) playing the game(s) in conjunction with viewing display of 3D medical images. During the course of the examination of the volume by the person(s) playing the game(s) viewing the medical images, it may be useful to quickly refer to an icon in order to re-orient where exactly in the body is some tissue of interest/concern. The icon would also be of utility in discussions between the person(s) playing the game(s). In FIG. 21A, an icon of the body in a vertical position facing forward 2100 is shown. The icon is marked up with an outline of the sub-volume being examined. Such a markup includes, but is not limited to, the following: markup of region of area of concern as indicated by the ordering physician; markup of the segmented volume that the radiologist is actively working on (e.g., radiologist is actively working on the liver item on the checklist, so the segmented liver is marked up on the icon); markup of sub-volume being examined by the radiologist (e.g., radiologist is actively working on a sub-volume within the liver within the confines of the volume-subtending 3D cursor); markup of viewing perspectives in relation to the icon. For example, the ordering physician may indicate an area of concern (e.g., sending patient specific image to the radiologist as described in U.S. Provisional Patent Application 62/843,612 for METHOD OF CREATING A COMPUTER-GENERATED PATIENT SPECIFIC IMAGE) and this area can be marked up on the virtual icon 2102. Next, the segmented volume 2104 that the radiologist is actively working on (e.g., liver) can be marked up. Next, a sub-volume within a 3D cursor 2106 can be marked up. An additional symbol may be shown external to the icon. For example, an initial viewing perspective symbol 2108 is shown to denote the initial viewing perspective. A movement symbol 2110 to denote the change in position from the initial viewing perspective denoted by the initial viewing perspective symbol 2108 to the subsequent viewing perspective denoted by the subsequent viewing perspective symbol 2112. In FIG. 21B, the user's extended reality headset 2114 is illustrated with a left eye display 2116 and a left eye view of the 3D cursor 2118 and a right eye display 2120 with a right eye view of the 3D cursor 2122. Note that a left eye view of the marked up 3D icon 2124 is shown in the left eye display 2116 and a right eye view of the marked up 3D icon 2126 is shown in the right eye display. Thus, the outline of the sub-volume being examined can be one of the markups of the icon. The approximate location of the 3D cursor(s) within the human body icon is another example markup of the icon. Orientation of the body would be under the control of the person(s) playing the game(s) viewing the medical images, as would whether to display the icon or not. For example, the icon could be rotated, translated, warped (with corresponding voxel manipulation if desired) or other alterations as directed by the radiologist. Furthermore, adding a marked up icon of a 3D cursor to the diagnostic 2D radiology monitor could be performed. As the person(s) playing the game(s) viewing the medical images rotate, tilt, and zoom, the tissue contained in the 3D cursor, it may be useful to see where the current viewpoint is relative to the initial viewpoint (e.g., voxels' locations have changed from initial orientation through rolling, pitching and/or yaw commands to a new orientation). This illustration shows a cured arrow originating at the initial viewing point and terminating at the current viewing point. Whether to display the icon or not would be under the control of the medical person viewing the medical images. The icon of a 3D cursor displays the contents of the 3D cursor which have been rotated and viewed from different viewpoints, it is useful to simultaneously see where the current position and view point are with respect to the original position.

Figure 22:
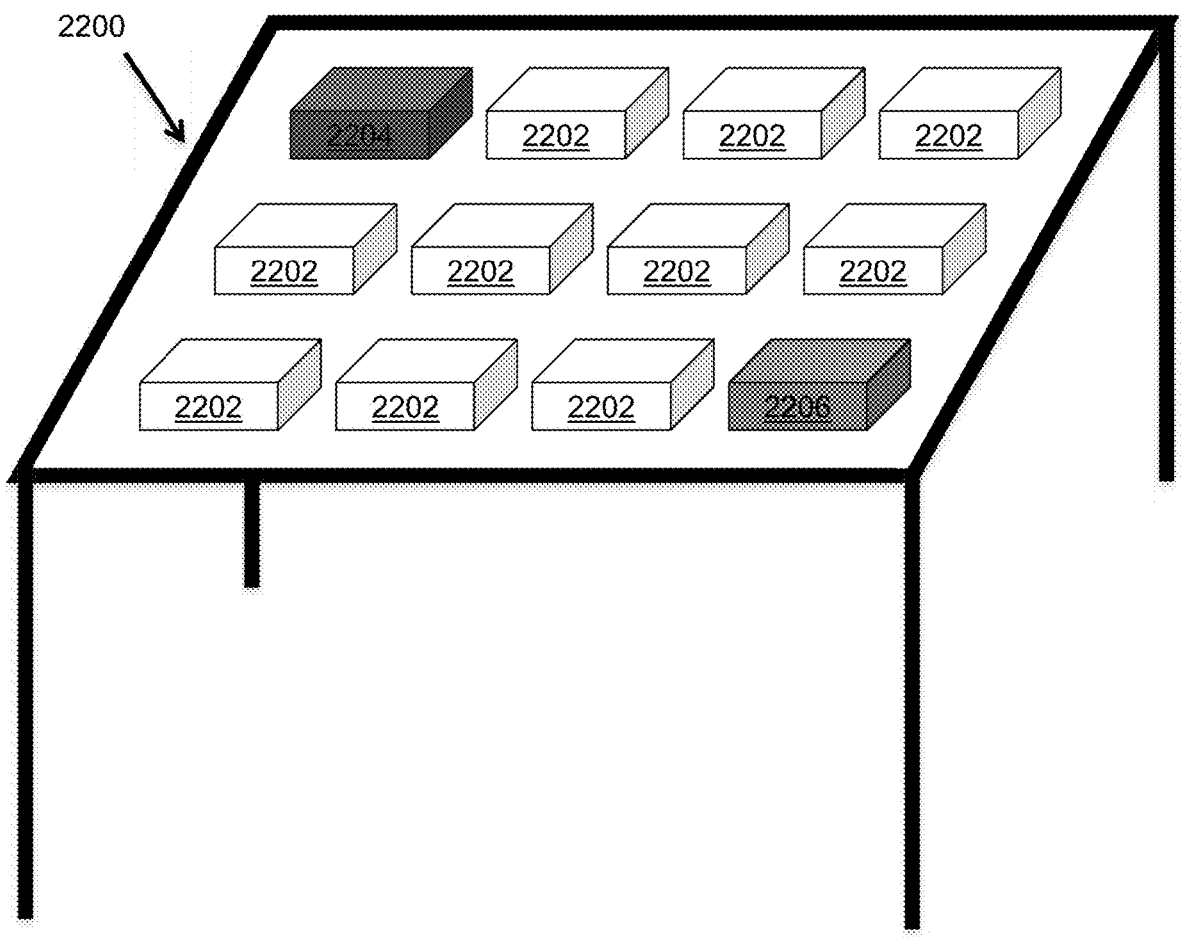
FIG. 22 illustrates a virtual moveable table for storing virtual images of suspect tissue stored by checklist category.

FIG. 22 illustrates a virtual moveable table for storing virtual images of suspect tissue stored by checklist category. These items could be re-arranged in both order and orientation for jigsaw puzzle type games. Items the person(s) playing the game(s) consider significant would be 'dragged and placed' in the marked virtual bins in accordance with investigative types of games. For bins without significant items, there would be a statement 'unremarkable' which goes away when an item is added. This table with storage bins would facilitate the preparation of the report in advanced levels of the game and enhance quality and completeness of the report. An aspect of the game may include preparation of a medical report. Under this process, an annotated figure containing the tissue in question could be added to the report. This figure depicts a virtual movable table 2200 on which there are virtual storage bins that correspond to items on the medical institution checklist 2202, plus a bin for emergency items 2204, and a general/miscellaneous bin 2206 (e.g., image artifact, teaching case, quality improvement, etc.). The emergency bin 2204 could be used for placing findings for items of critical time sensitive information. The virtual mobile table is mobile in the sense that the user could view the virtual mobile table on an extended reality headset off to the side away from the imaging volume that the radiologist is currently working on. Then, the radiologist could move it or size it, such that it convenient for the work space. Items the medical personnel consider significant would be 'dragged and placed' in the respective virtual bins according to the checklist item being reviewed. For bins without significant items, there would be a statement 'unremarkable' on the checklist item on the report which goes away when an item is added, and the radiologist would replace that item on the checklist with the appropriate description. In addition to the reviewer, medical treatment personnel would be alerted and given access to the 'emergency bin' containing critical items. These items could be jointly reviewed by both treatment and review personnel on an expedited basis. This table with storage bins would facilitate the preparation of the report and enhance quality and completeness of the report. Current reporting is nominally limited to a word description only. Under this process, an annotated figure containing the tissue in question could be added.

Figure 23:
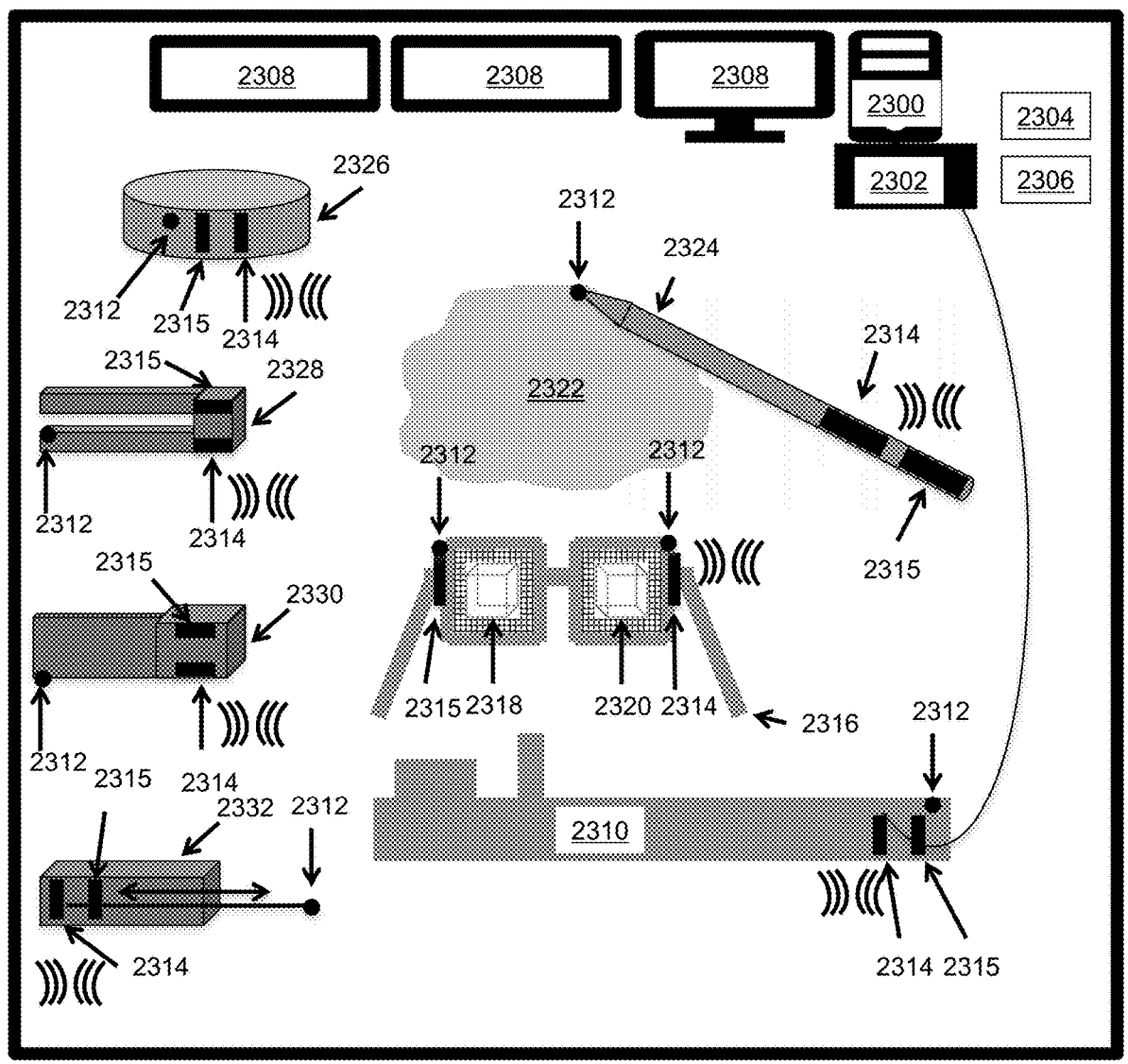
FIG. 23 illustrates a top-down view of the video game player's work station illustrating several of the geo-registered tools with position and orientation tracking wherein the video game player mimics the tasks of a medical doctor.

FIG. 23 illustrates a top down view of the video game player's work station illustrating several of the geo-registered tools with position and orientation tracking wherein the video game player mimics the tasks of a medical doctor. In addition to standard items present at radiology work stations including a computer 2300, keyboard 2302, mouse 2304, voice recorder 2306 and monitors 2308, multiple additional components are present in this patent. First, is the master control platform 2310, which has registration point(s) 2312 and capabilities for spatially registering each tool and other control features (e.g., raise or lower the whole imaging volume with respect to the position of the radiologist's head display unit). It has multiple buttons with multiple functions (e.g., easily toggle between control item (e.g., total volume; sub-volume; 3D cursor; and, focal point convergence) and image settings (e.g., window/leveling; and, filtering, etc.). The master control platform 2310 would be equipped with a send/receive element 2314 and an inertial measurement unit (IMU) 2315. All other tools are spatially-registered to the master control platform 2310, such that they are equipped with registration point(s) 2312, a send/receive element 2314 and an IMU 2315 for position (i.e., translation in the x-direction, y-direction or z-direction) and orientation (i.e., roll, pitch and yaw) tracking. Next, is the HDU 2316 (e.g., augmented reality, virtual reality, mixed reality) also equipped with registration point(s) 2312, send/receive element 2314, an IMU 2315 and a left eye image 2318 and a right eye image 2320. Next, is the virtual image 2322, which appears as a floating 3D volume in front of the radiologist as a virtual image on the HDU 2316. Next, is the focal point pen 2324, which is directed into the virtual image. This can be used for efficient interaction with the image, such as selecting objects, guiding focal point convergence, write notes, place symbols, etc. As with the other tools, the focal point pen is also equipped with registration point(s) 2312 and a send/receive element 2314 and an IMU 2315. Fifth, is the geo-registered platform 2326, which can be used to move a sub-volume in any position or orientation (e.g., place an unknown mass inside of a 3D cursor and onto the hand-held geo-registered platform, then move the object to a position that is best suited for close inspection such as 15 inches away from the radiologist's eyes, rotate to look at the virtual object from the top, side, bottom, back, etc.). The geo-registered platform is also equipped with registration point(s) 2312 and send/receive element(s) 2314 and an IMU 2315. Next is the hand-held multi-function tool 2328, which can be used as any programmed surgical-type device (e.g., drill, retractor, etc.), which is equipped with registration point(s) 2312 and send/receive element(s) 2314 and an IMU. Next, is the hand-held scalpel/knife 2330, which is equipped with registration point(s) 2312, send/receive elements 2314 and an IMU 2315. Next, is the catheter device 2332, which would not necessarily have to have registration point(s) 2312 and send/receive element(s) 2314 and an IMU 2315 for position and orientation tracking, but it could if the users demand it so. Note that each item has options for wireless capabilities and battery powered. The virtual image 2322 is displayed on the HDU 2316, but appears as a 3D object sitting right in front of the video game player.

Figure 24:
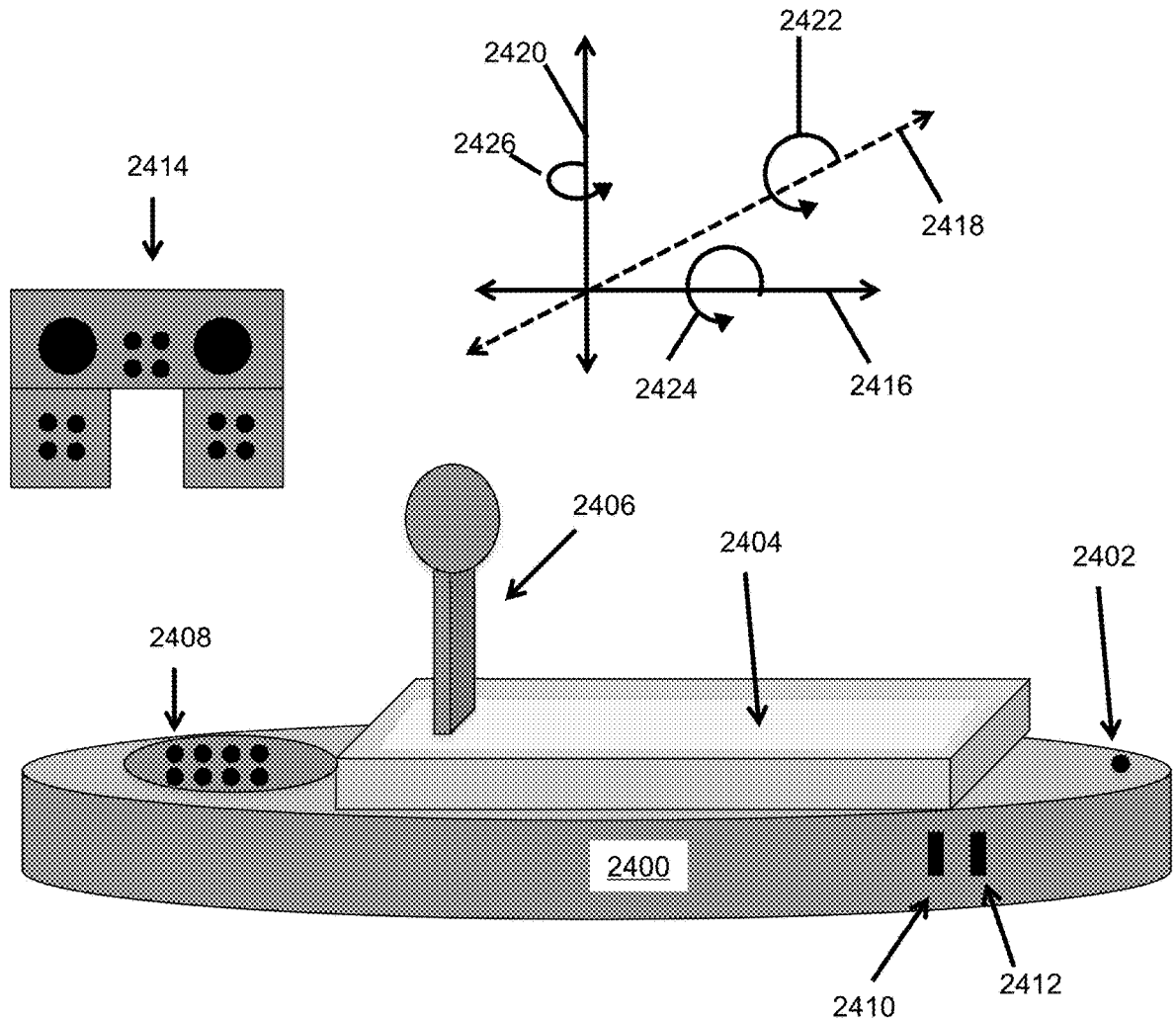
FIG. 24 illustrates the master control panel for the video game player with registration points.

FIG. 24 illustrates the master control panel for the video game player with registration points. The master control platform is also referred to as the geo-registration unit. The master control platform 2400 consists of the following: mount (not shown) equipped with position relative to the head display unit using a geo-registration point(s) 2402; platform(s) 2404 with roll 2422, pitch 2424 and yaw 2426 and translation capability in the x-direction (i.e., side to side) 2416, y-direction (i.e., forward-to-back) 2418 and z-direction (i.e., up-down) 2420; joystick(s) 2406 with roll 2422, pitch 2424 and yaw 2426 (RPY) and translation capability in the x-direction 2416, y-direction 2418 and z-direction 2420; multiple buttons 2408 to easily toggle between control item (e.g., total volume; sub-volume; 3D cursor; and, focal point convergence toggling) and image settings (e.g., window/leveling; and, filtering, etc.). Joystick 2406 functionality includes the following: a) change the orientation of the 3D cursor roll, pitch and yaw; b) zoom the medical person viewpoint in toward the 3D cursor and out away from the cursor; c) invoke convergence; d) raise and lower the 3D cursor as to where it is displayed on the headset; e) change the size, shape, and color of the 3D cursor; e) invoke filtering, segmentation, sequencing, statistical, and reporting operations; f) invoke pointer and movement control thereof; g) annotate one or more 3D cursors within the volume of interest; h) invoke icon options. Although not mandatory, the desk geo-registration device 2400 would typically be at a fixed location at the medical person's work station. Another optional component of the geo-registration unit 2400 would be an additional controller 2414, which would be an ergonomic controller with buttons and joysticks. The coordinate system for the medical images volume would be offset a specified distance from the desk geo-registration device 2400. The registration points on the focal point pen and the pedestal/platform would physically touch the registration point(s) 2402 on the desk geo-registration device during the initialization process. Key elements of the desk geo-registration device include: the geo-registration point 2402; the transmit/receive unit (aka, the send/receive element) 2410; battery element (not shown); and b) the IMU 2412.

FIG. 25 illustrates the geo-registered true stereoscopic head display unit within the geo-registration coordinate system viewing a 3D cursor. The HDU 2500 is equipped with an IMU 2502, a transmit/receive element 2504 and a geo-registration point(s) 2506. Thus, for a fixed location of a 3D cursor with respect to the master control unit, a movement of the video game player's head will alter the appearance of the 3D cursor on the HDU 2500. The HDU 2500 is illustrated in this figure. Key components include: an IMU 2502; lenses 2510 that display both the real-world scene and the virtual image 2508; geo-registration point 2506; battery element (not shown); and digital transmit/receive system 2504. The IMU 2502 senses head motion and transmits changes of head position and orientation through the transmission system to the master control platform. The computer calculates the effect of changes of head position and orientation and changes what is being displayed on the lenses and transmits the adjusted display to the HDU 2500 to project on the lenses 2508. What is being projected on the lenses displays is also affected by commands issued through the joystick/master control platform to the computer, and thence an updated display transmitted to the HDU 2500. The geo-registration point interacts with the desk geo-registration device and is initialized with X 2516, Y 2518, Z 2520 coordinates and orientation (i.e., roll 2522, pitch 2524, and yaw 2526) at time of initialization. Note: these coordinates and orientation are re-computed when the person(s) playing the game(s) viewing the medical images puts on the HDU.

Figure 26:
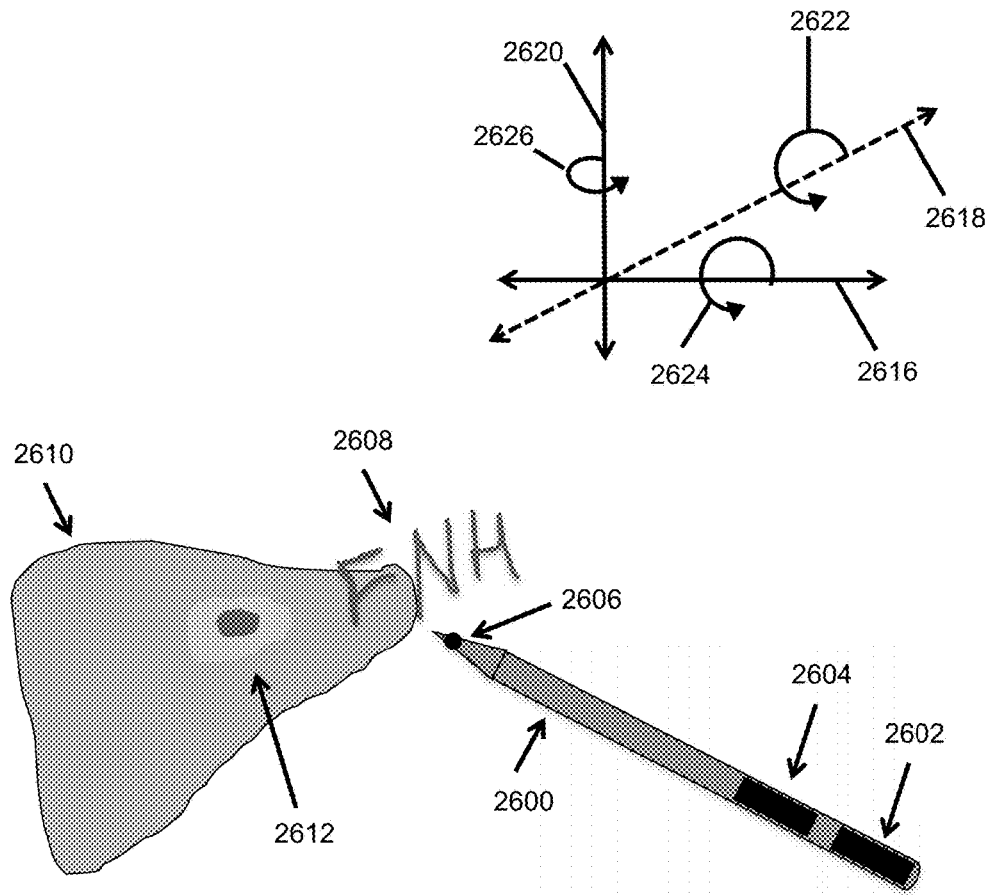
FIG. 26 illustrates the geo-registered focal point pen in greater detail.

FIG. 26 illustrates the geo-registered focal point pen in greater detail. The geo-registered focal point pen 2600 is equipped with a geo-registration point 2606 at the tip, contains an IMU 2602 for determining location and/or orientation, and a transmit/receive unit 2604 for communication with the computer. The focal point pen 2600 can be moved within the 3D volume and point to anomalous tissue 2612 and inscribe notes 2608 within 3D space, but typically adjacent to the volume of interest 2610 for future reference and to place it into the report. The geo-registration point 2606 interacts with the master control platform and is initialized with X 2616, Y 2618, Z 2620 coordinates and orientation (i.e., roll 2622, pitch 2624, and yaw 2626) at time of initialization. Note: these coordinates and orientation are re-computed when the medical person viewing the medical images puts on the HDU. The focal point pen 2600 which is an actual, tangible object in the shape of a pen (or other actual object that could be used for pointing) would be held by person(s) playing the game(s) viewing the medical images, which would interact with the virtual medical images. (Note that the focal point pen 2600 is geo-registered with the medical images 2610.) This interaction includes actually physically moving the focal point pen 2600 in the air in front of the person(s) playing the game(s) viewing the medical images 2610 and, simultaneously, be moving the focal point pen 2600 through virtual space showing the 3D volumetric medical image 2610. The display would show a virtual pen (not shown) properly geo-registered within the 3D medical image. If there is mis-registration between the tangible focal point pen 2600 and the virtual focal point pen (not shown), the focal point pen 2600 could be moved back to the master control platform for re-registration for a process including touching the registration points(s) 2606 of the focal point pen to the registration point of the master control platform (not shown). There is a wide array of uses for the focal point pen which would include, but not be limited to, the following: moving the focal point pen 2600 within the 3D image set so as to follow arteries/veins within a complex vascular structure; touching a point within the 3D image set with the tip of the focal point pen 2600 for annotation and/or cross reference the a particular 2D image slice; writing notes, drawing symbols (e.g., encircle tissue of concern with a sphere; draw arrows); and, illustrating a potential cut path for surgical planning.

Figure 27A:
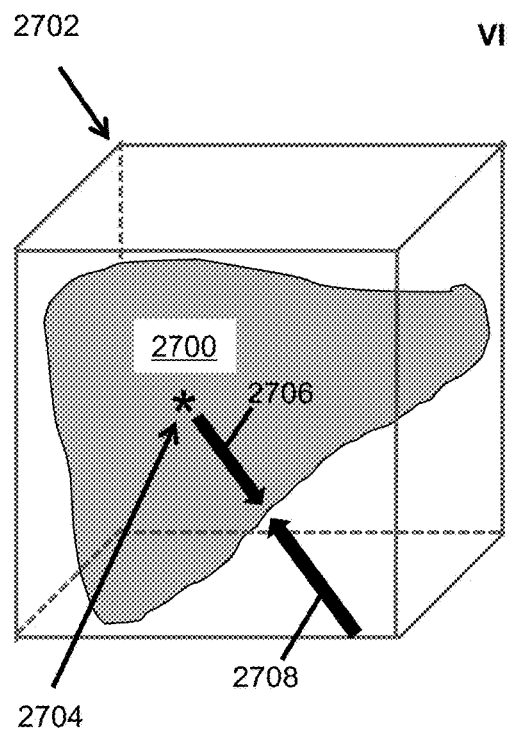
FIGS. 27A, 27B, 27C, and 27D illustrate an ablative process that the player can use to aid in searching the internal structure and any abnormalities of an organ.
Figure 27B:
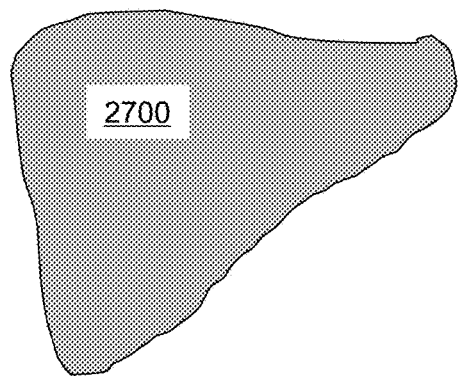
Figure 27C:
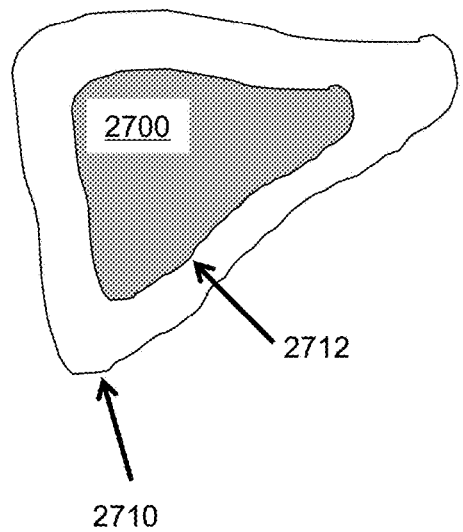
Figure 27D:
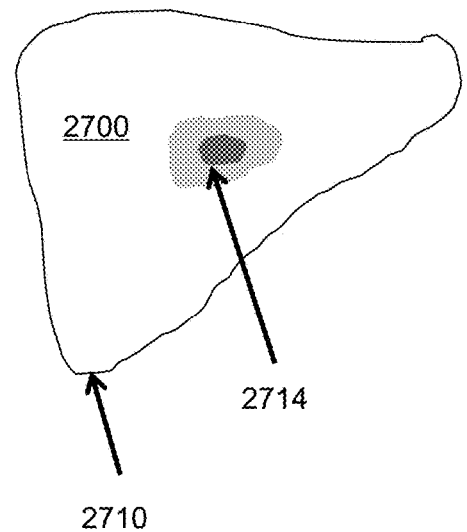

FIGS. 27A, 27B, 27C, and 27D illustrate an ablative process that the player can use to aid in searching the internal structure and any abnormalities of an organ. FIG. 27A, FIG. 27B, FIG. 27C and FIG. 27D illustrate an ablative process to aid in searching the internal structure and any abnormalities of an organ. FIG. 27A illustrates an organ 2700 contained within the 3D cursor 2702. To achieve the outer shell of the organ inside the 3D cursor, one can perform a segmentation process to isolate the organ 2700. Then, the surface layer of voxels can be eliminated, beginning the ablation process. The surface layer of voxels can be identified by going from either the center voxel of the organ 2704 in the outward direction 2706 toward the boundary of the 3D cursor 2702 and analyzing voxel properties to determine to voxel at the surface. Alternatively, the surface layer of voxels can be identified by going from the boundary of the 3D cursor 2702 in the inward direction 2708 towards the center voxel of the organ 2704 and analyzing voxel properties to determine the voxel at the surface. FIG. 27B shows the organ of interest 2700 without the 3D cursor 2702. FIG. 27C sequentially removes voxels from outer shells 2702 of the organ 2700 in a step-wise fashion. The original outer surface 2710 is shown. Also, the new outer surface 2712 after ablation of N steps is shown. FIG. 27D shows an abnormality 2714 within the confines of the organ 2700. During each ablative step, normal organ tissue would be ablated away, but abnormal liver tissue would remain. In this example, an illustration of a liver lesion called a focal nodular hyperplasia (FNH) 2714 is shown, but all remaining normal liver tissue is disappeared. For orientation, the original outer surface 2710 is shown.

FIG. 28 illustrates the hand-held pedestal within the geo-registration coordinate system. The hand-held pedestal 2800 has a geo-registration point 2802, an IMU 2804 and transmit/receive unit 2806, which updates the system with regard to its location and orientation. The location of the pedestal can be changed (up/down/left/right/forward/back) and its orientation (roll, pitch and yaw). This overcomes the difficulty and non-intuitive interfaces with medical imaging including keyboard, mouse, button on joystick, etc. The radiologist can use a 3D cursor 2808 with copied contents 2810, affix it to the pedestal/platform and, transport it to a new location in front of him/her. The geo-registration point 2802 interacts with the desk geo-registration device and is initialized with X 2812, Y 2814, Z 2816 coordinates and orientation (i.e., roll 2818, pitch 2820, and yaw 2822) at time of initialization. Note: these coordinates and orientation are re-computed when the medical person viewing the medical images puts on the HDU. The pedestal/platform 2800 which is an actual tangible object, such as in the shape of a cell phone (or other actual object that could be used for holding a virtual object) would be held by medical person viewing the medical images which would interact with the virtual medical images. While a geo-registered tool with geo-registration point(s) 2802, an inertial measurement unit 2804 and transmit/receive unit is preferred 2806, an alternative embodiment would be to use a set of cameras (e.g., located on the HDU or elsewhere in the room) for object tracking. (Note that the pedestal/platform 2800 is geo-registered with the medical images.) This interaction includes actually moving pedestal/platform 2800 the air in front of the medical person viewing the medical images and, simultaneously, be moving the pedestal/platform 2800 through virtual space showing the 3D volumetric medical image. The display would show a virtual pedestal/platform 2800 properly geo-registered within the 3D medical image. There is a wide array of uses for the pedestal/platform 2800 which would include, but not be limited to, the following: moving the pedestal/platform 2800 to a volume of interest within the 3D medical image (e.g., volume 2810 contained within the 3D cursor 2808) by hand movements of the pedestal/platform 2800 and then the medical person viewing the medical images issues command to affix the volume of interest 2810 inside the 3D cursor 2810 to the pedestal/platform 2800. Note: once the volume 2810 was affixed to the pedestal/platform 2800, the volume of interest 2810 would move, corresponding to and as the pedestal/platform 2800 was moved. Thence, the medical person viewing the medical images by hand control of the pedestal/platform 2800 could rotate, tilt the pedestal/platform 2800 for examination. Further, this examination process could be accompanied by head movements by medical person viewing the medical images to obtain a better perspective of any tissue of potential concern. This process allows one to examine a medical imaging dataset the same way that he/she has spent a lifetime examining hand-held objects, such as a studying the stitches on baseball/softball. The volume on the pedestal/platform 2800 would return to the original position on the command of the medical person. Note: battery in this element is not shown.

Figure 29A:
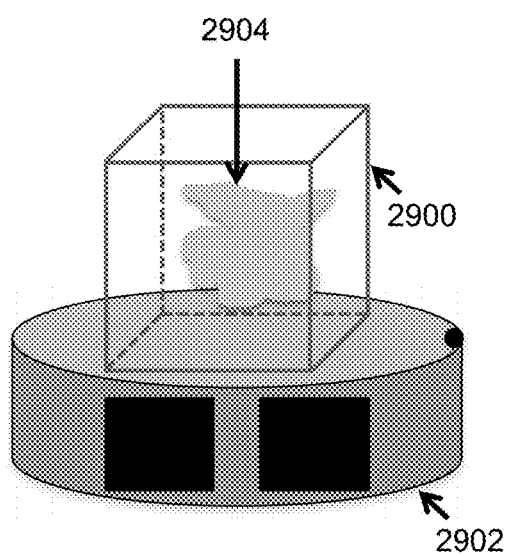
FIGS. 29A and 29B illustrate the capability of using the geo-registered platform to display a known pathology from a database next to another geo-registered platform with an unknown pathology from the patient's scan.
Figure 29B:
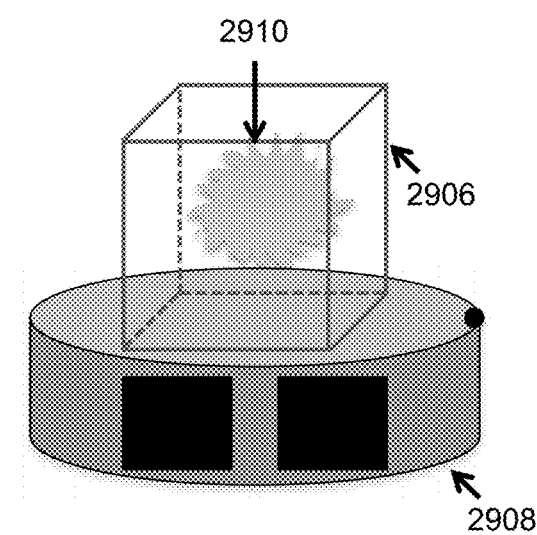

FIGS. 29A and 29B illustrate the capability of using the geo-registered platform to display a known pathology from a database next to another geo-registered platform with an unknown pathology from the patient's scan. In FIG. 29A, a first 3D cursor 2900 is shown affixed to a first geo-registered platform 2902. The first 3D cursor 2900 contains an unknown lesion 2904. For example, the unknown lesion 2904 could be a breast mass, but the precise diagnosis of the breast mass is not known. In FIG. 29B, a second 3D cursor 2906 is shown affixed to a second geo-registered platform 2908. The second 3D cursor 2906 contains a known lesion 2910. For example, the known lesion 2910 could be a breast mass and the precise diagnosis of the breast mass is known to be an infiltrating ductal carcinoma. Note that the margins of the known mass 2910 in this example are spiculated whereas the margins of the unknown mass 2904 are lobulated. The radiologist would conclude from this comparison that the patient's pathology in the unknown lesion 2904 is different from the pathology in the known lesion 2910. Thus, the radiologist would have the ability to place the known pathology lesion 2910 on one pedestal. This can be imported from a known pathology database. The radiologist would have the ability to place unknown pathology lesion 2904 on another pedestal. This is from the patient's scan. These two could be compared in a side-by-side fashion.

Figure 30A:
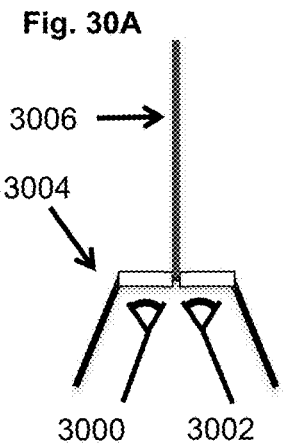
FIGS. 30A, 30B, 30C, 30D, 30E, 30F, 30G, 30H, and 30I illustrate visual markers to indicate HDU orientation and eye orientation.
Figure 30B:
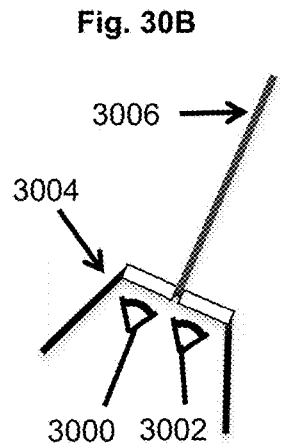
Figure 30C:
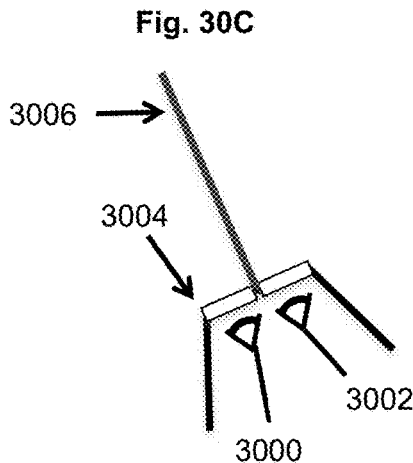
Figure 30D:
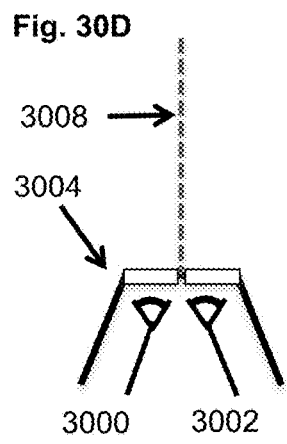
Figure 30E:
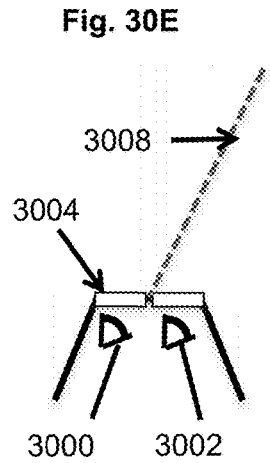
Figure 30F:
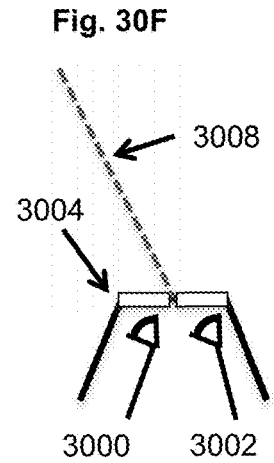
Figure 30G:
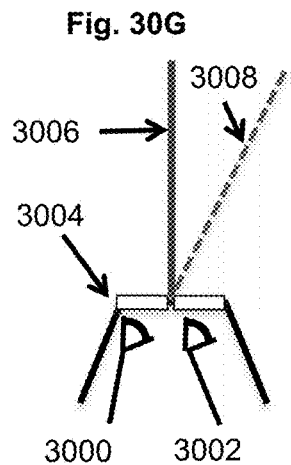
Figure 30H:
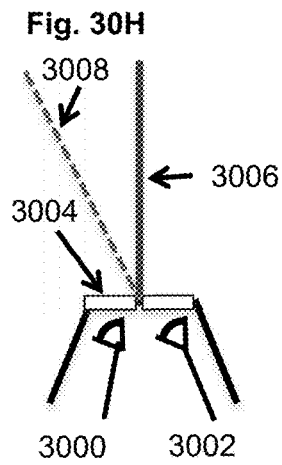
Figure 30I:
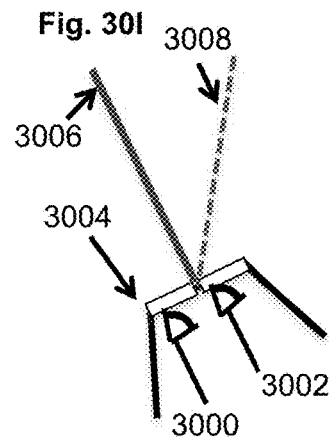

FIGS. 30A, 30B, 30C, 30D, 30E, 30F, 30G, 30H, and 30I illustrate visual markers to indicate head display unit (HDU) orientation and eye orientation. Two visual indicators are illustrated including a "HDU orientation visual indicator" and an "gaze direction visual indicator". A top down view of the left eye 3000, right eye 3002, head display unit (HDU) 3004 are shown. In FIG. 30A, the HDU 3004 is shown with a forward orientation. The HDU orientation visual indicator 3006 is shown extending from the HDU 3004 in the direction perpendicular to the front of the HDU 3004. Note that in this case, the direction of the left eye 3000 and right eye 3002 matches that of the direction of the HDU orientation visual indicator 3006. In FIG. 30B, the HDU 3004 is shown with an orientation angled approximately 30 degrees to the right. The HDU visual indicator 3006 is shown extending from the HDU 3004 in the direction perpendicular to the front of the HDU 3004. Note that in this case, the direction of the left eye 3000 and right eye 3002 matches that of the direction of the HDU orientation visual indicator 3006. In FIG. 30C, the HDU 3004 is shown with an orientation angled approximately 30 degrees to the left. The HDU visual indicator 3006 is shown extending from the HDU 3004 in the direction perpendicular to the front of the HDU 3004. Note that in this case, the direction of the left eye 3000 and right eye 3002 matches that of the direction of the HDU orientation visual indicator 3006. Thus, the HDU visual indicator 3006 is always oriented in the direction perpendicular to the front of the HDU 3004. No matter whether the user turns their head to the left of turns their head to the right, or up or down, the HDU visual indicator 3006 will always be oriented in the direction perpendicular to the HDU 3004. In FIG. 30D, the HDU 3004 is shown with an initial forward orientation. The left eye 3000 and right eye 3002 are also in the forward direction, which happens to matches that of the HDU 3004. The gaze direction visual indicator 3008 is shown extending from the HDU 3004 in the direction that matches that of the gaze direction of the left eye 3000 and right eye 3002. In FIG. 30E, the HDU 3004 is shown with an initial forward orientation. The left eye 3000 and right eye 3002 are shown gazing approximately 30 degrees to the right. The gaze direction visual indicator 3008 is shown extending from the HDU 3004 in the direction that matches that of the gaze direction of the left eye 3000 and right eye 3002. In FIG. 30F, the HDU 3004 is shown with an initial forward orientation. The left eye 3000 and right eye 3002 are shown gazing approximately 30 degrees to the left. The gaze direction visual indicator 3008 is shown extending from the HDU 3004 in the direction that matches that of the gaze direction of the left eye 3000 and right eye 3002. Thus, no matter which way the user gazes, up, down, left or right, the gaze direction visual indicator 3008 will be shown in the direction that the user is looking. To develop the gaze direction visual indicator, an eye tracking system will be used to determine the gaze direction, then an augmented reality gaze direction visual indicator line will be drawn from the HDU in the direction of the gaze. This gaze direction visual indicator can be updated in real time in accordance with varying gaze direction and a real time eye tracking system in place. If desired, a separate left eye gaze direction visual indicator and a separate right eye gaze direction visual indicator could be used. These separate gaze direction visual indicator lines would not converge in situations such as disconjugate gaze. In FIG. 30G, the HDU 3004 is shown with a forward orientation and the HDU orientation visual indicator 3006 is in the forward orientation. The left eye 3000 and right eye 3002 are gazing approximately 30 degrees to the right and the gaze direction visual indicator 3008 is in the direction approximately 30 degrees to the right. In FIG. 30H, the HDU is shown with a forward orientation and the HDU orientation visual indicator 3006 is in the forward direction. The left eye 3000 and right eye 3002 are gazing approximately 30 degrees to the left and the gaze direction visual indicator 3008 is in the direction approximately 30 degrees to the left. In FIG. 30I, the HDU 3004 is shown angled approximately 20 degrees to the left and the HDU orientation visual indicator 3006 is in the direction angled approximately 20 degrees to the left. The left eye 3000 and right eye 3002 are oriented approximately 30 degrees to the right and the gaze direction visual indicator 3008 is oriented approximately 10 degrees to the right.

Figure 31A:
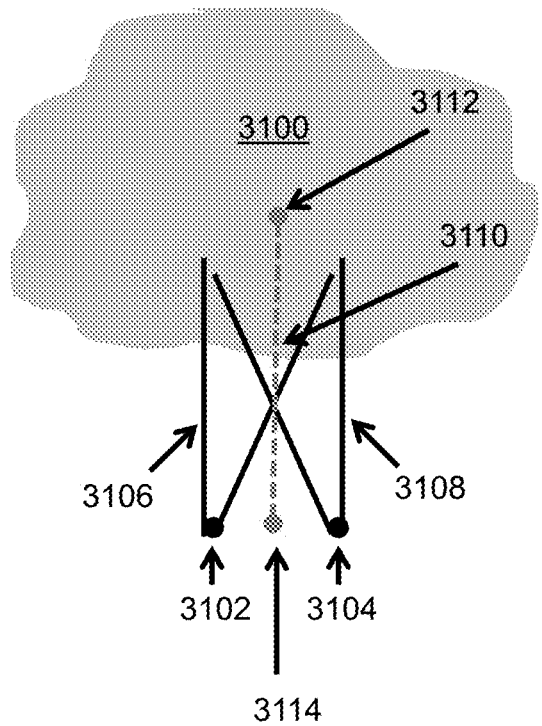
FIGS. 31A and 31B illustrate left eye gaze direction visual indicator, right eye gaze direction visual indicator, convergence and center line of focus.
Figure 31B:
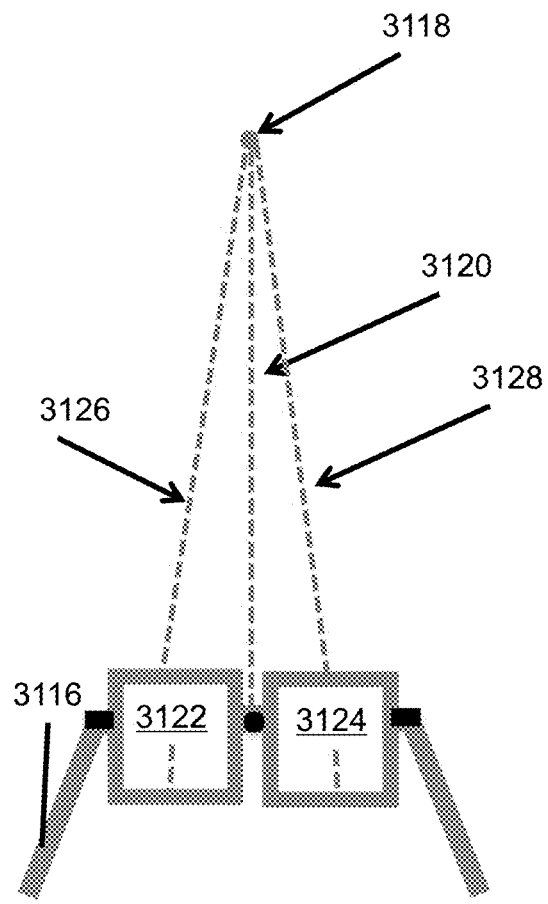

FIGS. 31A and 31B illustrate left eye gaze direction visual indicator and right eye gaze direction visual indicator. In FIG. 31A, the volume of interest 3100 is shown. Note that left eye view point 3102 and right eye view point 3104 are shown. Note the left eye viewing angle 3106 and right eye viewing angle 3108 are shown. Note the convergence point 3112. Note that a center line 3110 is shown extending from a point on (or near) the plane between the eyes 3114 to (or near) the convergence point 3112. This line may help focus the user's attention or show one user where a different user is looking. In FIG. 31B, the center line of one user could be displayed on all user's HDUs in a multi-HDU user situation. This would enable one user to see another user's center line. This could facilitate communication between multiple users. The center line 3110 would be placed in a fashion that would aid the user in their attention and their focus. For example, a center line 3120 appearing from overhead towards the object of interest (e.g., near the focal point 3118) may be the optimal placement. Note that the center line 3120 would only be visible to those wearing HDUs 3116 and would appear as a 3D structure in the left eye display 3122 and right eye display 3124. In a situation wherein there are multiple users (e.g., multi-player game), one user can visually see where the other user is looking by seeing their center line of focus. This can assist with education, task coordination, etc. Alternatively, a left eye gaze direction visual indicator 3126 and a right eye gaze direction visual indicator 3128 could be shown.

Figure 32:
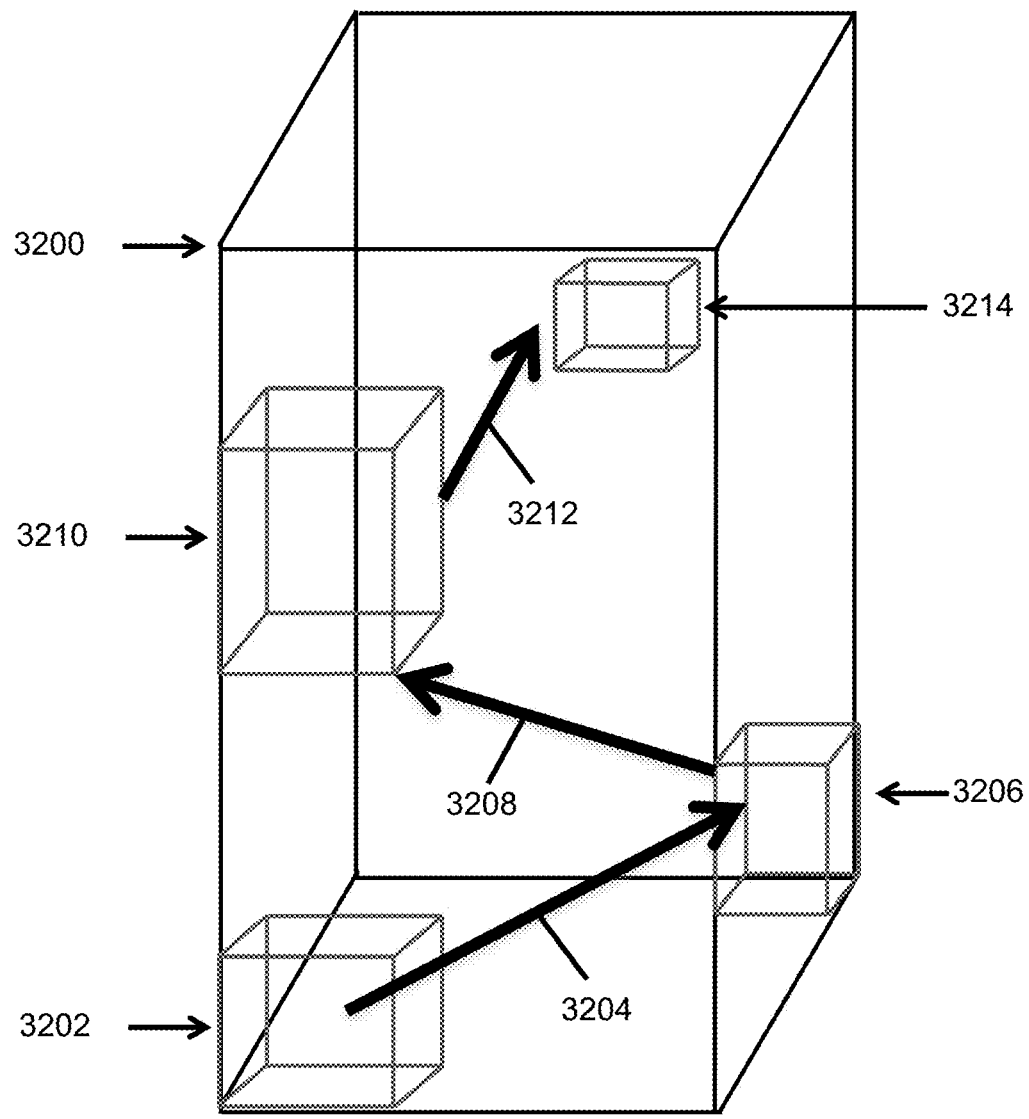
FIG. 32 illustrates sequencing of movement of the 3D cursor through the volume of interest in a random pattern.

FIG. 32 illustrates sequencing of movement of the 3D cursor through the volume of interest in a random pattern. A random pattern is used based on items of possible interest, the reviewing person can view the totality of the virtual medical image volume at once and apply techniques such as changing transparency and applying false color to structures of differing density than the nominal density of the organ being examined. The reviewer can then move and re-size the 3D cursor to the various objects of potential interest for detailed examination. In this illustration, a total scanned volume 3200 is shown. A first sub-volume displayed in a 3D cursor is shown at the first time point 3202. The 3D cursor is subsequently moved in direction 3204. A subsequent sub-volume displayed in a second re-sized 3D cursor is shown at a subsequent time point 3206. The 3D cursor is subsequently moved in direction 3208. A subsequent sub-volume displayed in a second re-sized 3D cursor is shown at a subsequent time point 3210. The 3D cursor is subsequently moved in direction 3212. A subsequent sub-volume displayed in a second re-sized 3D cursor is shown at a subsequent time point 3214. This figure shows multiple moves and resizes the 3D cursor to view example tissues of interest. This can type of search pattern can expedite the review process. This search patterns employ a 3D cursor (U.S. Pat. No. 9,980,691 and U.S. patent application Ser. No. 15/878, 463). Note: when reviewing medical images in the original 2D format, the eyes jump from one spot to another following the reviewing individual's saccadian path and substantial portions of a slice may not be observed and, consequently, small masses may be missed. In the use of the 3D cursor, small findings subtend a larger fraction of presented image and the probability of detection increases proportionally. If such a random search pattern is displayed, the computer program would keep track of the portions of the total volume that have been displayed and the portions of the total volume that have not been displayed. In the event that some portions of the total volume have not been displayed by a 3D cursor, the program would remind the user to view these regions. In some implementations, sub-volumes are displayed to the medical personnel in an automated pattern, which includes, but is not limited to, the following: windshield wiper pattern or layer-by-layer pattern. At any time point, the 3D cursor and/or sub-volume within the 3D cursor can be copied and pasted to a virtual movable table for later review. For example, the radiologist may want to round up all of the potentially abnormal or definitely abnormal findings first. Then, the radiologist may want to study each of the abnormal findings in great detail at a later time period. Each time an abnormal imaging finding is identified, the radiologist could place the abnormal finding in a 3D cursor and make sure that the entirety of the abnormal finding is included in the sub-volume (e.g., the entirety of the liver mass is included in the 3D cursor, which defines the boundaries of the sub-volume). Then, set the sub-volume aside into a virtual bucket or virtual 3D clipboard. Then, review the rest of the total imaging volume. Once the entire total imaging volume has been removed and all abnormal sub-volumes have been placed in the virtual bucket or virtual 3D clipboard, then the radiologist would begin close inspection of the volumes in the virtual bucket or virtual 3D clipboard.

Figure 33:
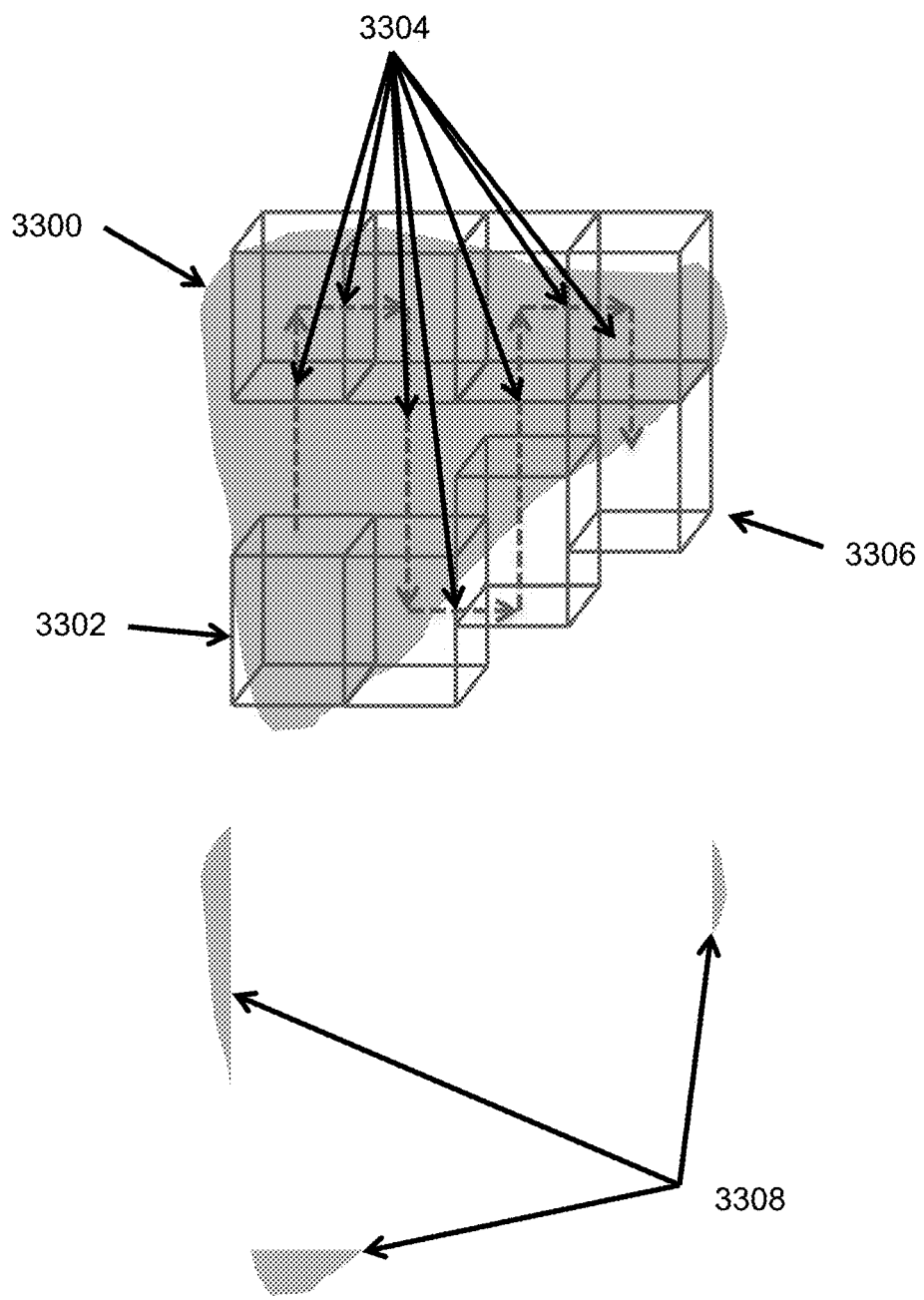
FIG. 33 illustrates volume of interest to be reviewed and a process whereby any areas, which intended for review which were missed, could be highlighted to the medical person performing the review.

FIG. 33 illustrates volume of interest to be reviewed and a process whereby any areas, which intended for review which were missed, could be highlighted to the medical person performing the review. These identified sub-volumes could be reviewed subsequently, thereby ensuring completeness of the review. This process invokes the sequential selection of sub-volumes of the volume of interest through use of the 3D cursor (U.S. Pat. No. 9,980,691 and U.S. patent application Ser. No. 15/878,463) to sequentially step through the volume being examined (e.g., per following medical institution checklist). Further, after the step-by-step process has been completed, the question could arise as to whether the entire volume has been examined. In this implementation, the volume contained in each of the 3D cursors which had been examined could be totaled and subtracted from the total original volume. This could result missing some portions of the original volume that were intended for review. In this implementation, these missed portions would be highlighted to the medical person performing the review and he/she could be alerted to continue the review and examine these missed portions. Note: when reviewing medical images in the original 2D format, the eyes jump from one spot to another following the reviewing individual's saccadian path and substantial portions of a slice may not be observed and, consequently, small masses may be missed. In the use of the 3D cursor, these small masses subtend a larger fraction of presented image and the probability of detection increases proportionally. This figure illustrates sequencing of movement of the 3D cursor through an organ of interest. A volume of interest (i.e., liver) 3300 is shown. A sub-volume 3302 displayed at time point #1 is illustrated. The 3D cursor moves 3304 in a systematic fashion through the volume of interest 3300. The final sub-volume 3306 would be displayed at time point #N. Control of viewing of the medical images (e.g., changing from one increment to another) would be controlled by the medical personnel. Alternatively, the user could move the control the movement of the 3D cursor by the joystick or other geo-registered tools, as discussed in U.S. patent application Ser. No. 16/524,275. Finally, volumes displayed in the 3D cursor can be tracked and then reviewed at a later time (i.e., prior to the completion of the exam). Sub-volume size changes based on indication routine screening versus cancer. Further, recording the position of the 3D cursor over time and comparing the sub-volumes displayed with the total volume would enable accounting for sub-volumes that have not yet been displayed to the medical professional 3308. Alternatively, subtracting the sub-volumes have been displayed from the whole volume, it is possible to determine which sub-volumes have not yet been displayed. Note that a few areas of the structure were missed (i.e., not included in the 3D cursor volumes) 3308; these can be tracked and the radiologist has the option to review these areas prior to the completion of the exam. These missed sub-volumes 3308 can be moved to a new position and examined. In another embodiment, the user can select the size of the 3D cursor, rate of the movement of the cursor and the computer performs automated movement through the volume of interest on the checklist item. If the organ is unremarkable, the sub-volumes within the cubes could be changed in a way that the imaged structures are unremarkable (e.g., deleted, changed in Hounsfield unit, etc).

Figure 34A:
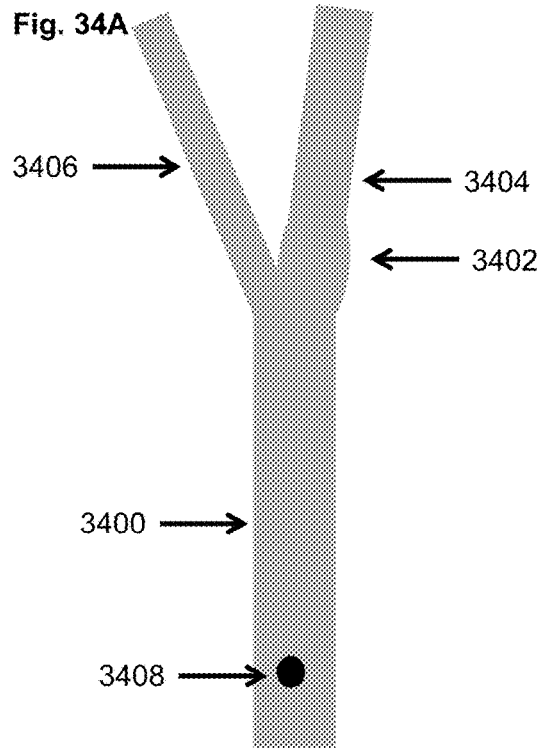
FIGS. 34A, 34B, 34C, and 34D illustrate methods of helping the radiologist in search pattern via utilization of saccades search technique.
Figure 34B:
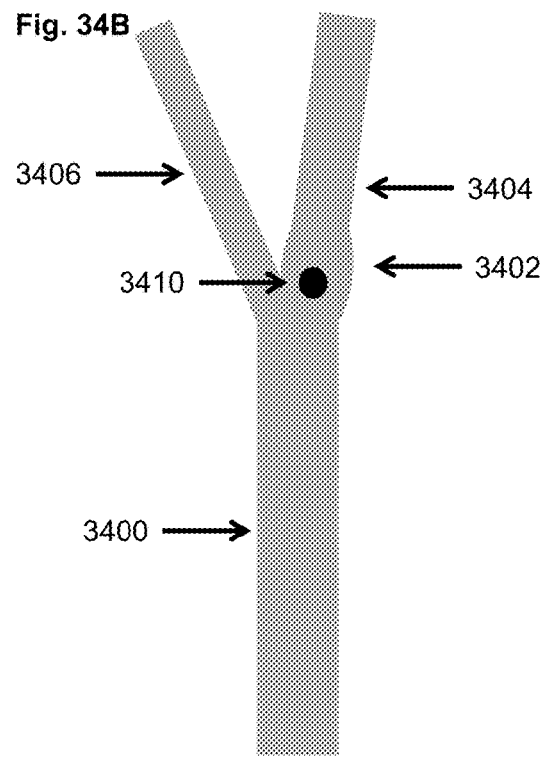
Figure 34C:
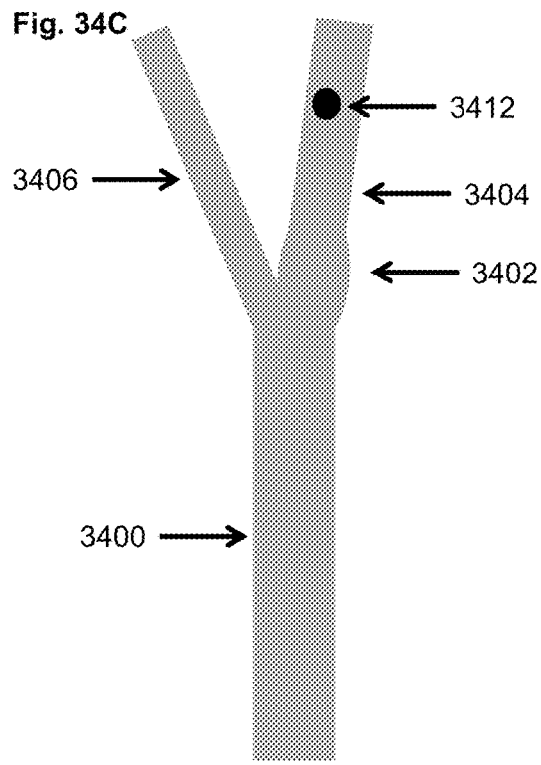
Figure 34D:
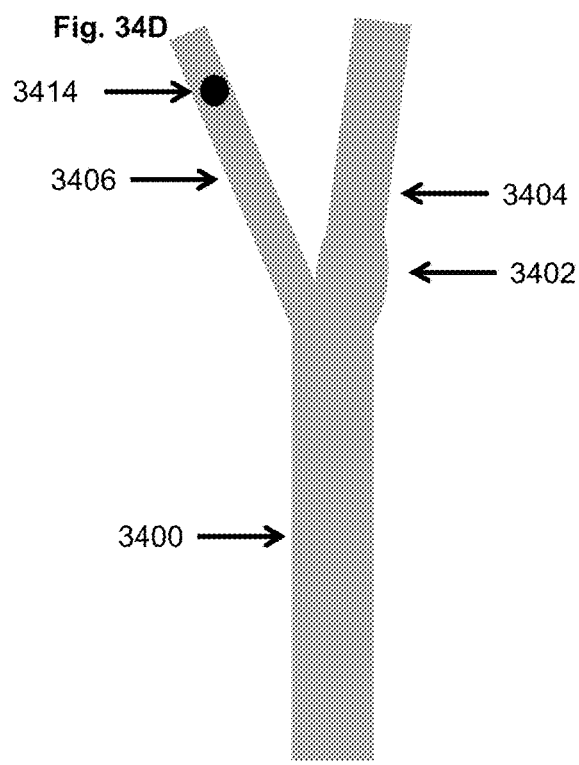

FIGS. 34A, 34B, 34C, and 34D illustrate methods of helping the radiologist in search pattern via utilization of saccades search technique. The example shown is a branching carotid artery arterial structure wherein the common carotid artery 3400, carotid bulb 3402, internal carotid artery 3404 and external carotid artery 3406 are shown. In FIG. 34A, a first black dot 3408 would appear at a first time point. The appearance of a first black dot 3408 (or other similar type object) would draw the eye in towards the new structure. This would force the human eye (and fovea region) to look in the region of the first black dot 3408 and examine those local structures, namely the common carotid artery 3400. In FIG. 34B at a later time point, the first black dot 3408 disappears and a second black dot 3410 would appear at a second time point. The appearance of a second black dot 3410 (or other similar type object) would draw the eye in towards the new structure. This would force the human eye (and fovea region) to look in the carotid bulb 3402. In FIG. 34C at a later time point, the second black dot 3410 disappears and a third black dot 3412 would appear at a third time point. The appearance of a third black dot 3412 (or other similar type object) would draw the eye in towards the new structure. This would force the human eye (and fovea region) to look in the internal carotid artery 3404. In FIG. 34D at a later time point, the third black dot 3412 disappears and a fourth black dot 3414 would appear at a fourth time point. The appearance of a fourth black dot 3414 (or other similar type object) would draw the eye in towards the new structure. This would force the human eye (and fovea region) to look in the region of the external carotid artery 3406. Thus, utilization of planned structures that pop up on an image at strategic points would therefore use the human eye's natural ability to perform saccades and utilize the fovea. Segmentation algorithms could be utilized, and dots strategically positioned at sites where pathology is detected (e.g., by an AI algorithm) or where pathology is statistically most likely to occur (e.g., atherosclerosis in the carotid bulbs). Furthermore, the method that the radiologist could implement to help with the saccades includes on a set time (e.g., a new dot appears every 2 seconds) or could be by user control (e.g., user clicks a mouse and a new dot appears). Furthermore, the dots could be tied to a radiologist's checklist, such that when all dots are examined for a particular structure, evaluation of that structure would be complete. Furthermore, an eye tracking system could be utilized to help determine the optimum tools for lesion detection (e.g., whether it be saccades or smooth tracking or combination thereof).

Figure 35A:
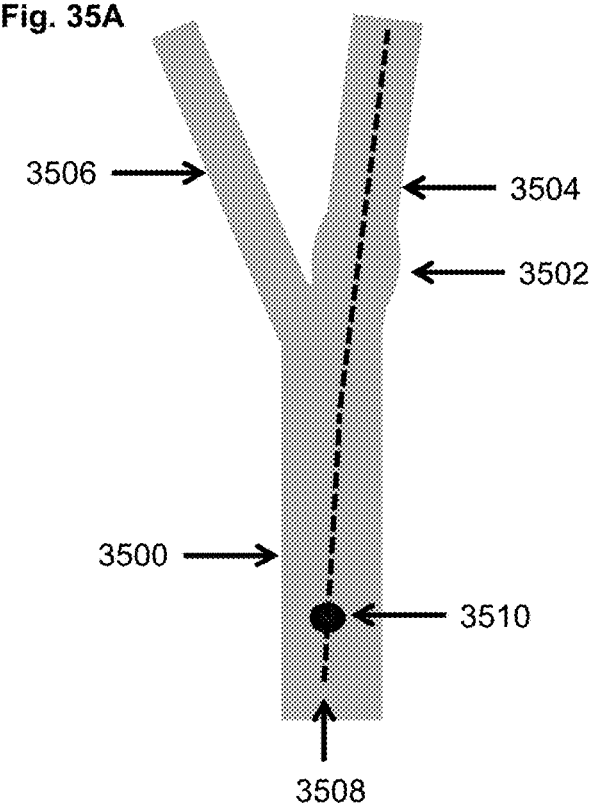
FIGS. 35A, 35B, 35C, and 35D illustrate a method of helping the radiologist in search pattern via utilization of smooth tracking search technique.
Figure 35B:
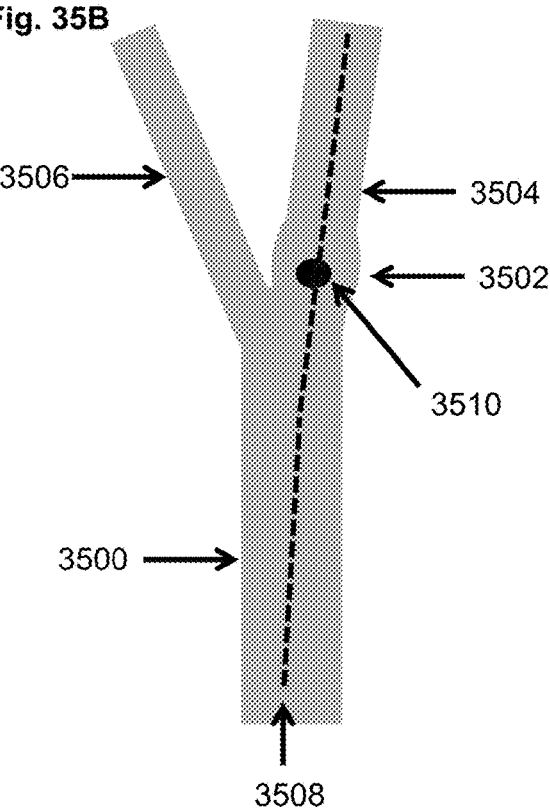
Figure 35C:
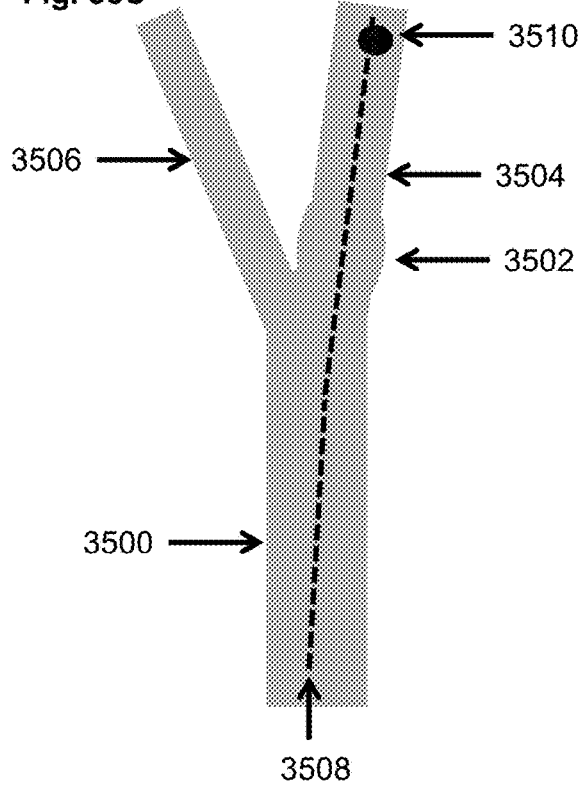
Figure 35D:
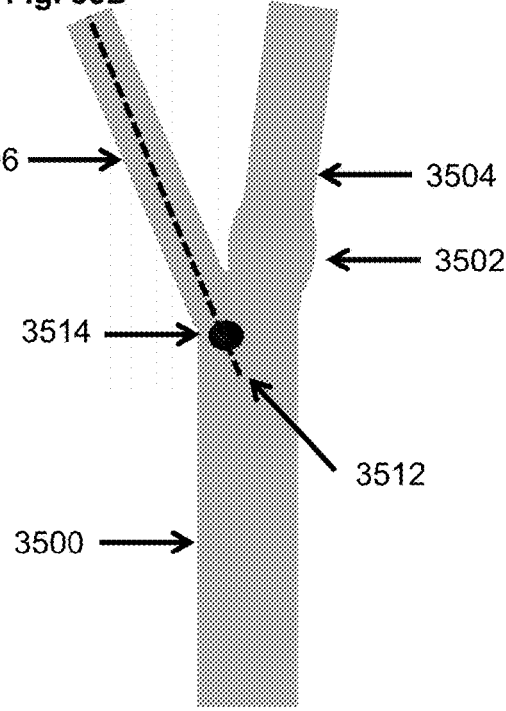

FIGS. 35A, 35B, 35C, and 35D illustrate a method of helping the radiologist in search pattern via utilization of smooth tracking search technique. The example shown is an arterial structure wherein the common carotid artery 3500, carotid bulb 3502, internal carotid artery 3504 and external carotid artery 3506 are shown. In FIG. 35A, a line 3508 is shown coursing from the common carotid artery 3500 through the carotid bulb 3502 and into the internal carotid artery 3504. The line 3508 would be an optional feature and would not be required for smooth tracking, and could be displayed or hidden by user preference. A black dot 3510 (or similar visual structure) is shown at the proximal portion of the common carotid artery 3500 at an initial time point. In FIG. 35B, the black dot 3510 is shown to be moving along that line and is now at the level of the carotid bulb 3502. Note that the black dot 3510 would be shown continuously and moved in a continuous fashion with a frame rate fast enough that the human eye sees smooth movement. In FIG. 35C, the black dot 3510 is shown to be moving along that line and is now at the level of the internal carotid artery 3504. Note that the black dot 3510 would be shown continuously and moved in a continuous fashion with a frame rate fast enough that the human eye sees smooth movement. After scanning the course of the common carotid artery 3500, carotid bulb 3502 and internal carotid artery 3504 for abnormalities, the radiologist may then elect to scan the external carotid artery 3506. In FIG. 35D, a new line 3512 and a new black dot 3514 would then be used for scanning of the next structure. This new line 3512 and new black dot 3514 would suddenly appear at the new location and the human eye would perform a saccades movement to the new items. Then, the new black dot 3514 would smoothly move along the course of the external carotid artery 3506 in a continuous, smooth fashion with a frame rate fast enough that the human eye sees smooth movement. This would be analogous to a patient performing smooth tracking of a doctor's finger. Thus, a combination of saccades and smooth tracking eye movements can be utilized to help the radiologist improve visual tracking of abnormalities within structures. The rate of the smooth tracking and movement of the black dot would be controlled by the radiologist via adjusting input settings. Alternatively, this type of tracking could be linked to the movement of a focal point pen within the image. The human can move the black dot (via the focal point pen or GUI) or the computer or can control the black dot to aid the human in performing smooth tracking and assessment of the structure. Also, the radiologist can tab through various points of interest within the sub-volume as desired. This act will serve to mimic the human eyes' natural movement of performing saccades from one item of interest to another item of interest.

Figure 36:
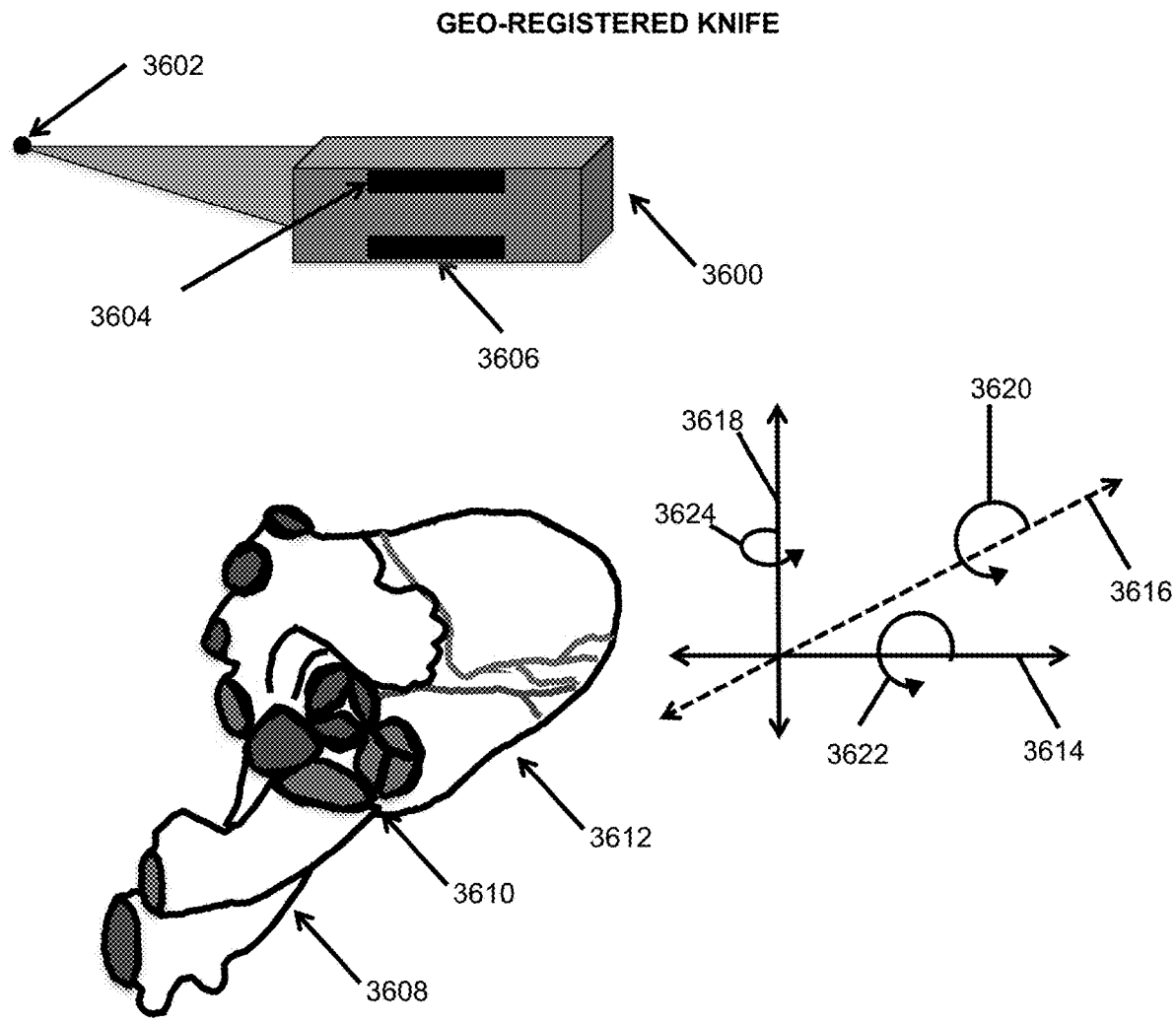
FIG. 36 illustrates a geo-registered knife and how it could be used to carve away a portion of a heart.

FIG. 36 illustrates a geo-registered knife and how it could be used to carve away a portion of a heart. The geo-registered knife 3600 contains a registration point 3602, a transmit/receive element 3604 and an IMU 3606. The knife 3600 is a physical object and its position and orientation can be changed by the video game player(s). The knife 3600 has the properties of being able to dissect the virtual images and remove them in order to better view the internal structure of the tissue at hand. For example, the great vessels 3608 could be cut along a cutting plane 3610 and rotated away from the remainder of the heart 3612. The coordinates of the cutting surface can be determined by the user. The geo-registration point interacts with the desk geo-registration device and is initialized with X 3614, Y 3616, Z 3618 coordinates and orientation (i.e., roll 3620, pitch 3622, and yaw 3624) at time of initialization. Note: these coordinates and orientation are re-computed when the video game player(s) viewing the medical images puts on the HDU. Note: battery in this element is not shown.

Figure 37:
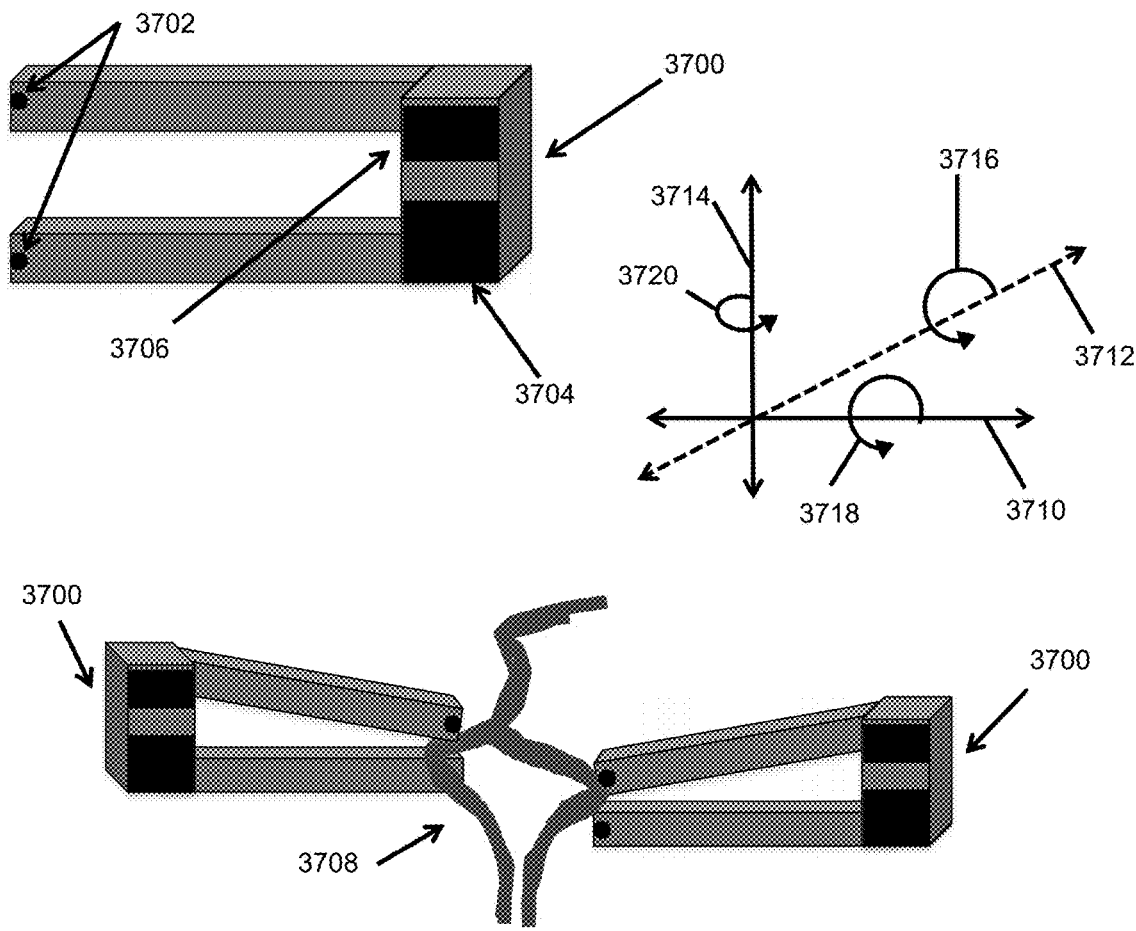
FIG. 37 illustrates a geo-registered multi-function tool used to manipulate voxels within the geo-registration coordinate system.

FIG. 37 illustrates a geo-registered multi-function tool used to manipulate voxels within the geo-registration coordinate system. The geo-registered multi-function tool 3700 is equipped with registration points 3702, an IMU 3704 and a transmit/receive unit 3706. The primary use of the geo-registered multi-function tool 3700 is expected to be grabbing tool that can manipulate and hold tissue (i.e., a set of voxels) in place. Other surgical instruments, such as drill, hammer, screw, scalpel, etc. can also interface with the tool. As illustrated, two multifunction tools are being used to pull apart two closely spaced blood vessels 3708 with voxel manipulations performed in accordance with U.S. patent application Ser. No. 16/195,251, which is incorporated by reference. The geo-registration point interacts with the desk geo-registration device and is initialized with X 3710, Y 3712, Z 3714 coordinates and orientation (i.e., roll 3716, pitch 3718, and yaw 3720) at time of initialization. Note: these coordinates and orientation are re-computed when the video game player(s) viewing the medical images puts on the HDU. Note: battery in this element is not shown.

Figure 38:
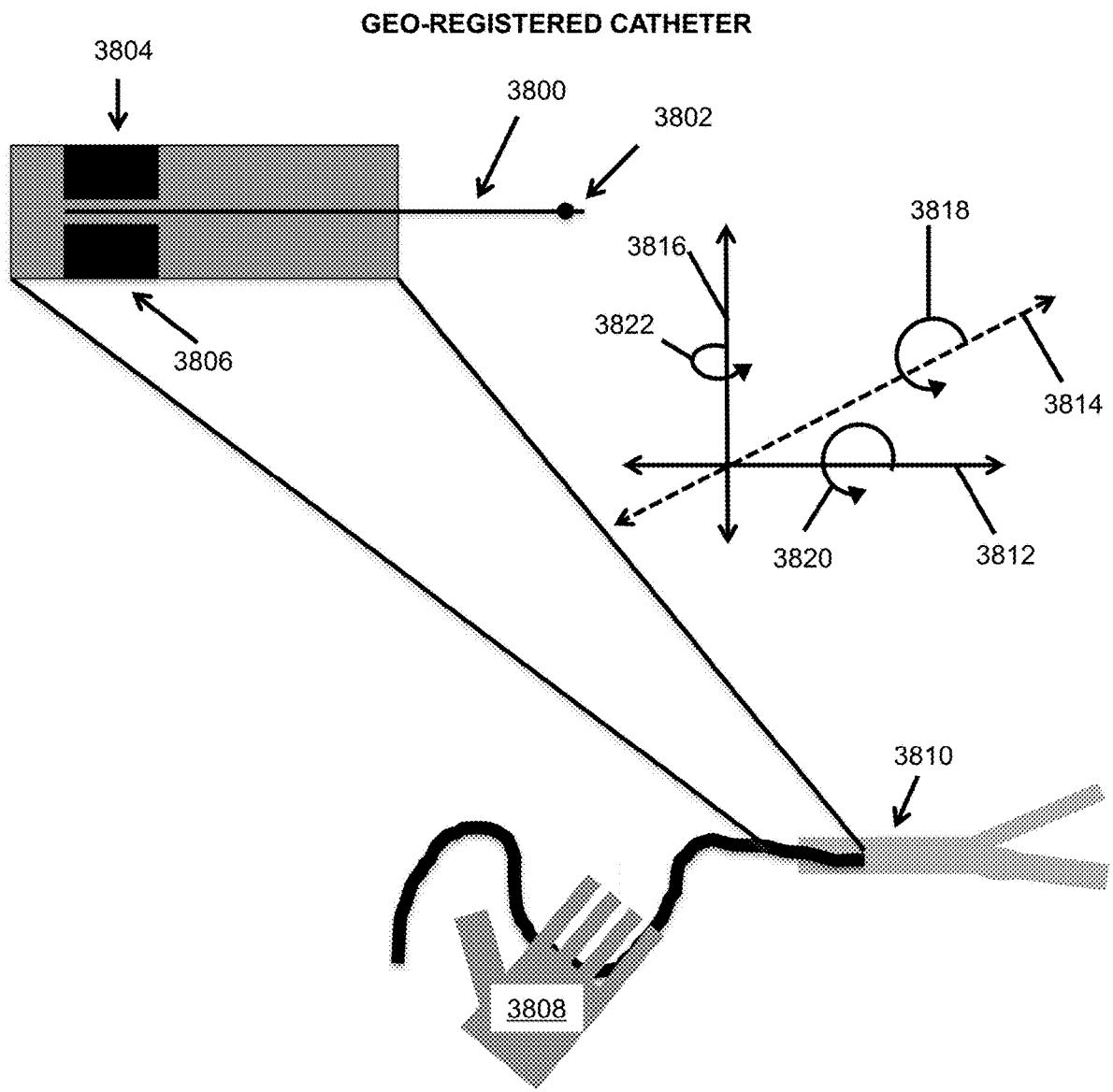
FIG. 38 illustrates the geo-registered catheter with navigation through a blood vessel.

FIG. 38 illustrates the geo-registered catheter with navigation through a blood vessel. The geo-registered catheter 3800 consists of a tubular structure with a wire entering into it. The geo-registered catheter has a registration point 3802, an IMU 3804 and a transmit/receive unit 3806. The user's hand 3808 would insert the catheter 3800 into the virtual image and continuously push it up through the vascular system 3810. Each succeeding element of the catheter goes to the location and orientation of the immediately proceeding (or trailing) element as the video game player(s) pushes, pulls or twists the catheter. Similarly, the virtual catheter would be able to move through the virtual image via translation in the X 3812, Y 3814 or Z 3816 coordinates or via roll 3818, pitch 3820 and yaw 3822. This could aid in pre-operative planning or facilitate training interventional operations. Note: battery in this element is not shown.

Figure 39:
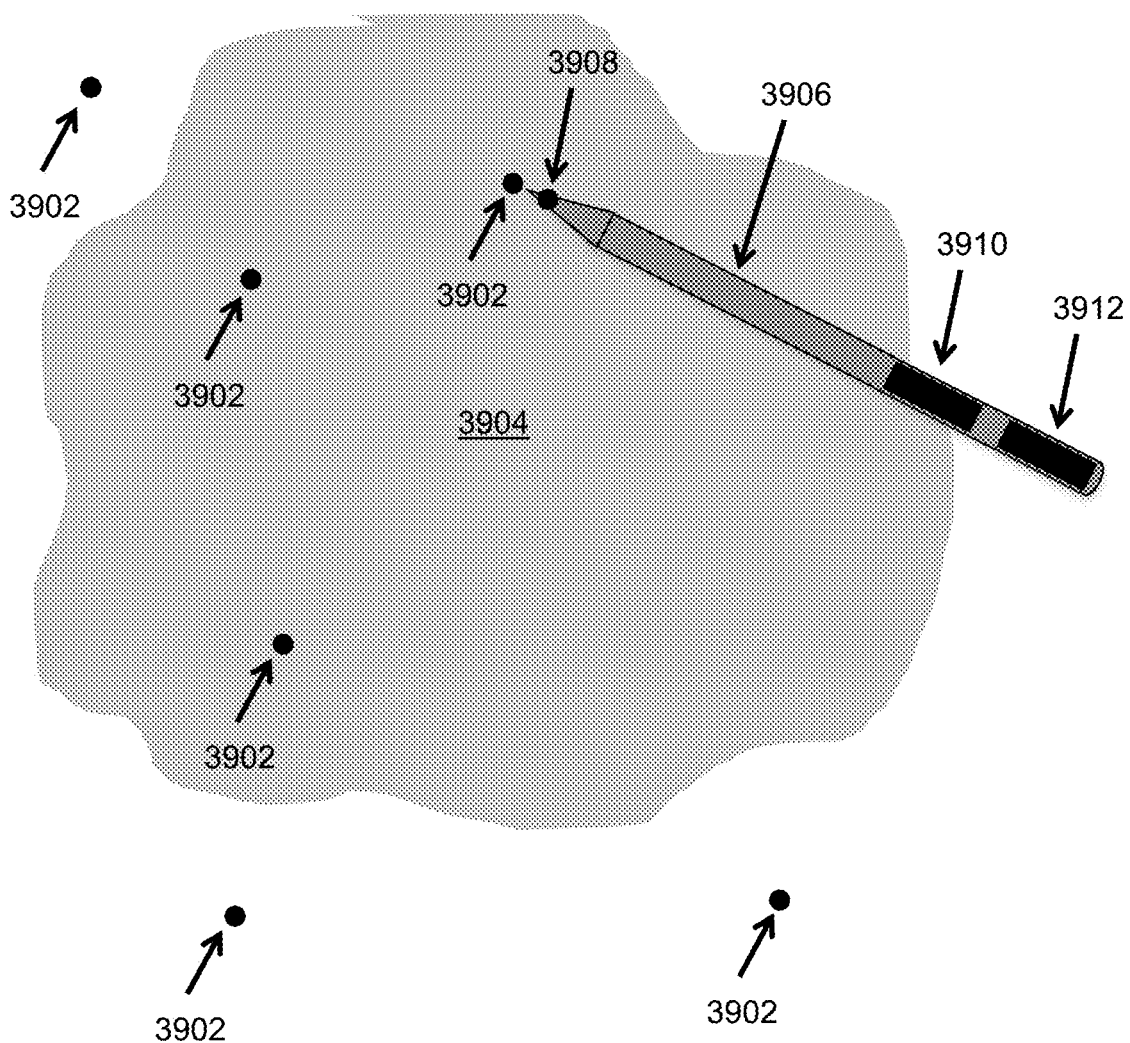
FIG. 39 illustrates multiple calibration points within the geo-registration coordinate system.

FIG. 39 illustrates multiple calibration points within the geo-registration coordinate system. In this figure, the focal point pen 3906 is illustrated touching the location of each of one of the calibration points 3902, which can be inside or outside of the imaging volume 3904. Note that the focal point pen 3906 has a registration point 3908, an IMU 3910 and a transmit/receive unit 3912.

Figure 40:
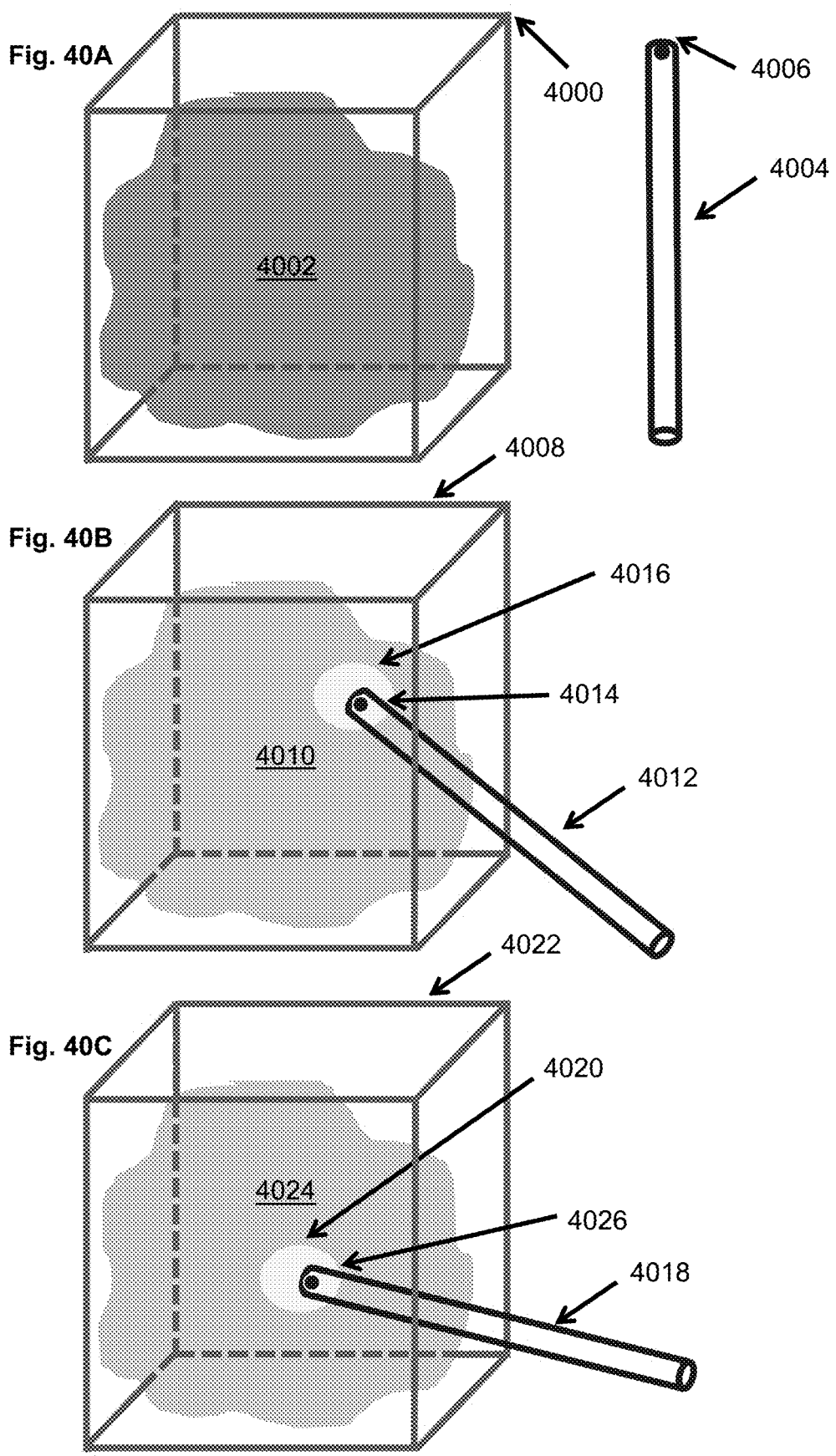
FIGS. 40A, 40B and 40C illustrate voxel manipulation based on interaction with a virtual tool.

FIGS. 40A, 40B and 40C illustrate voxel manipulation based on interaction with a virtual tool. FIG. 40A illustrates a 3D cursor 4000 containing a volume of interest 4002. Note that the volume of interest is of homogeneous mid-gray color. Also, note that the tip 4004 of the virtual tool (i.e., in this case, the virtual focal point pen) 4006 is located outside of the volume of interest 4004. FIG. 40B a 3D cursor 4008 containing a volume of interest 4010 with a change in position and orientation of the virtual tool (i.e., in this case, the focal point pen) 4012 with a portion of the virtual tool including the tip of the virtual tool 4014 now entering both the virtual 3D cursor 4008 and the volume of interest (e.g., contains selected tissue from the volumetric medical image) 4010. Note that multiple voxels 4016 in close proximity to the tip 4014 of the virtual tool 4012 have changed/highlighted to a light gray color. Also, note that the transparency of the tissue 4010 within the 3D cursor 4008 has changed to better visualize the tissue 4016 highlighted by the virtual focal point pen 4012 and the virtual focal point pen 4012 itself. FIG. 40C illustrates another change in position and orientation of the virtual focal point pen 4018 and corresponding alterations of the visual appearance of the nearby voxels 4020. A 3D cursor 4022 containing a volume of interest 4024 with an additional (compared to FIG. 40B) change in position and orientation of the virtual tool (i.e., in this case, the focal point pen) 4018 with a portion of the virtual tool 4018 including the tip of the virtual tool 4026 now entering both the virtual 3D cursor 4022 and the volume of interest (e.g., contains selected tissue from the volumetric medical image) 4024. Note that multiple voxels 4020 in close proximity to the tip 4026 of the virtual tool 4018 have changed/highlighted to a light gray color. Also, note that the transparency of the tissue 4024 within the 3D cursor 4022 has changed (compare with FIG. 40A) to better visualize the tissue 4024 highlighted by the virtual focal point pen 4018 and the virtual focal point pen 4018 itself. This serves to assist the user as to the precise location of the virtual tool within the volume of interest.

Figure 41:
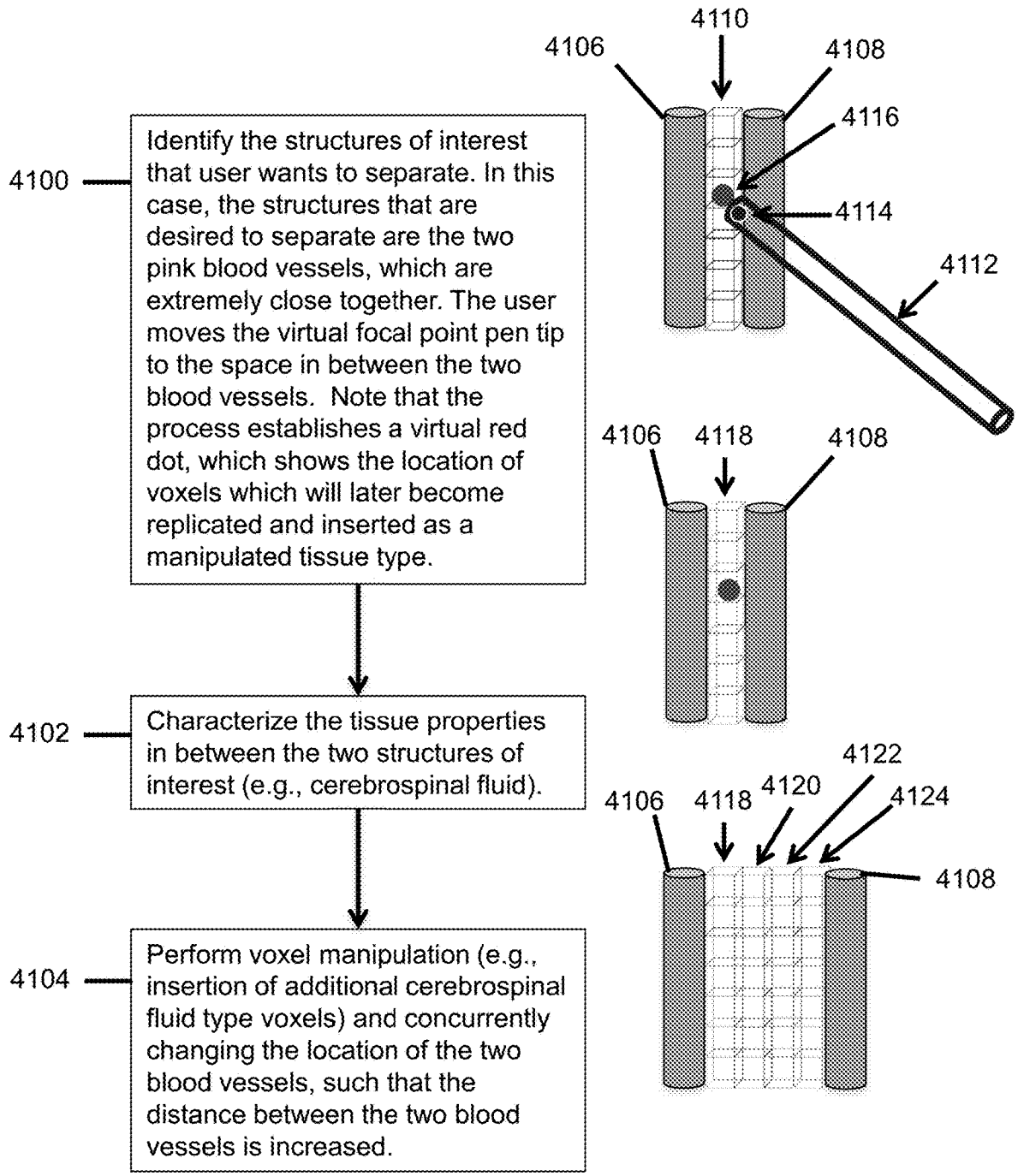
FIG. 41 illustrates a virtual focal point pen guiding voxel manipulation.

FIG. 41 illustrates a virtual focal point pen guiding voxel manipulation. The movement of the virtual focal point pen would be controlled by medical person viewing the medical images. This figure illustrates expanding distance between blood vessels which are closely space, overlapping and difficult to differentiate and a process to expand the distance between blood vessels. If an arterioveous malformation occurs in the brain in a region where multiple blood vessels are close together, it is difficult to identify which of these blood vessels to inject treatment material. Expanding the distance digitally can help identify the proper blood vessel for injection. Two conditions will be discussed. First, non-blood vessel tissue separates the blood vessels. Second, several blood vessels are in a cluster with little or no non-blood vessel tissue separating the blood vessels. If different types of tissue separate the blood vessels, then: a) segmentation to determine types of tissue present in the volume of interest; b) for all non-blood and non-blood vessel type of tissue, expand the volume by a multiplicative or additive factor; c) adjust the coordinates of blood and blood vessels to account for the expansion of the non-blood and non-blood vessel type of tissue. Next, to illustrate the cluster: d) perform segmentation to determine which voxels are predominately blood and which voxels are tissue (i.e., blood vessels); e) temporarily eliminate the tissue voxels; c) then use a multiplicative (or additive factor) to all coordinates of blood voxels; f) apply smoothing routine to blood vessels (optional); g) encase the blood voxels with tissue vessels. The display for the medical person viewing the medical images show the expanded blood vessel structure and thereby facilitate treatment. One of the problems encountered in radiology is the difficulty understanding the relationship between multiple complex anatomical structures. An example is a cerebral arteriovenous malformation (AVM). A complex cerebral AVM can consist of multiple tortuous feeding arteries, a tangle of nidus with aneurysms and multiple draining veins. It is extremely difficult to understand the precise anatomy of this complex structure. A process is illustrated as follows. In the first step 4100, identify the structures of interest that user wants to separate. In this case, the structures that are desired to separate are the two pink blood vessels, which are extremely close together. The user moves the virtual focal point pen tip to the space in between the two blood vessels. Note that the process establishes a virtual red dot 4116, which shows the location of voxels which will later become replicated and inserted as a manipulated tissue type. In the second step 4102, characterize the tissue properties in between the two structures of interest (e.g., cerebrospinal fluid). In the third step 4104, perform voxel manipulation (e.g., insertion of additional cerebrospinal fluid type voxels) and concurrently changing the location of the two blood vessels, such that the distance between the two blood vessels is increased. A first blood vessel 4106 and a second blood vessel 4108 are closely spaced with only a sliver of intervening cerebrospinal fluid type voxels 4110. A virtual pointer 4112 is shown. The tip of the virtual pointer 4114 is also shown. A virtual symbol (e.g., red dot 4116) is also shown to mark the location in the imaging volume that will be manipulated. Then, the tissue properties in between the two structures of interest (e.g., cerebrospinal fluid) can be assigned a particular tissue property. To illustrate this, the borders of each of these voxels has changed to a light blue 4118. Note that at this point, a first blood vessel 4106 and a second blood vessel 4108 are still closely spaced to one another. Then, to separate the first blood vessel 4106 from the second blood vessel 4108, three additional columns of cerebrospinal fluid voxels 4120, 4122 and 4124 are inserted. Note that the spacing between the first blood vessel 4106 and the second blood vessel 4108 has been increased. This is useful in that 3D viewing may now be improved with better ability to see and understand the relationship between closely spaced structures.

FIGS. 42A, 42B and 42C illustrate an example dashboard, message board, and body icon. FIG. 42A illustrates the virtual dashboard, which contains information, such as the demographics, prior history, current complaint and vitals. FIG. 42B illustrates the management board, which includes new information presented to the video game player from an event that occurred during the game, such as blood pressure rising now 180/112. FIG. 42C illustrates the human icon, which can help keep the video game player oriented.

FIGS. 43A and 43B illustrate the competitive structure of the game example scoring process. FIG. 43A illustrates a sample scoring process for a multiplayer game, which factors in difficulty level and time completed to achieve the best total score. FIG. 43B illustrates a sample scoring process for a multiplayer game, which factors in the number of cancers found, the stage, the number of metastasis and the total time to determine the score.

FIG. 44 illustrates learning objectives of different aspects of the games and example scenarios. This illustration serves as a summary of the type of games that are expected to be created out of this patent.

The invention claimed is:

1. A method comprising:
performing geo-registration of a virtual object to a first tangible object:
wherein the virtual object has location coordinates in physical space;
wherein a change in the first tangible object's position causes a corresponding change in the virtual object's position; and
wherein a change in the first tangible object's orientation causes a corresponding change in the virtual object's orientation;
performing geo-registration of a virtual tool to a second tangible object:
wherein the second tangible object is held in a user's hand;
wherein the virtual tool has location coordinates in physical space;
wherein a change in the second tangible object's position causes a corresponding change in the virtual tool's position; and
wherein a change in the second tangible object's orientation causes a corresponding change in the virtual tool's orientation;
tracking the first tangible object's position and orientation and the second tangible object's position and orientation;
determining a change in the virtual object's position and orientation, which corresponds to a change in the first tangible object's position and orientation;
determining a change in the virtual tool's position and orientation, which correspond to a change in the second tangible object's position and orientation;
causing the virtual object to be manipulated by the virtual tool:
wherein the manipulation occurs in response to placement of the virtual tool into the virtual object; and
wherein the manipulation comprises an alteration of the virtual object's three-dimensional structure;
assigning a virtual task to the user, in which the user manipulates the virtual object using the virtual tool to perform the assigned virtual task, wherein assigning the virtual task to the user comprises assigning a medical procedure; and
displaying the manipulated virtual object to the user wearing an extended reality head display unit.

2. The method of claim 1 further comprising:
assigning a set of coordinates on the virtual object designated as a spot; and
performing a programmed response when the spot is touched by the virtual tool.

3. The method of claim 2 wherein the programmed response is an information box.

4. The method of claim 1 wherein the virtual tool comprises a grabbing tool.

5. The method of claim 1 wherein the virtual tool comprises a pointing tool.

6. The method of claim 1 wherein the virtual tool comprises a cutting tool.

7. The method of claim 1 wherein the virtual tool comprises a writing tool.

8. The method of claim 1 comprising detecting by using an eye tracking system a location in the virtual object upon which the user's eyes are focused and providing an indication of the location in the virtual object upon which the user's eyes are focused to a second user who is wearing a second extended reality head display unit and looking at the virtual object.

9. The method of claim 1 comprising prompting performance of an additional task selected from the group consisting of: treating a stroke; treating an aneurysm; emplacing a virtual stent; performing a chemoembolization; and conducting a lung biopsy.

10. The method of claim 1 comprising scoring performance of the virtual task based on manipulation of the item virtual object.

11. The method of claim 1 comprising scoring performance based on correct identification of medical terminology for differing parts of anatomy and associated bodily functions.

12. The method of claim 1 comprising scoring performance based on accuracy and completeness of a diagnosis.

13. The method of claim 1 comprising scoring performance based on accuracy and time to complete a surgical operation.

14. The method of claim 1 comprising scoring performance based on accuracy and time to complete an interventional operation.

15. An apparatus comprising:
a first tangible object;
a second tangible object;
an extended reality head display unit; and
an image processor comprising a program stored on a computer-readable non-transitory media, the program comprising instructions for:
  performing geo-registration of a virtual object to a first tangible object:
    wherein the virtual object has location coordinates in physical space;
    wherein a change in the first tangible object's position causes a corresponding change in the virtual object's position; and
    wherein a change in the first tangible object's orientation causes a corresponding change in the virtual object's orientation;
  performing geo-registration of a virtual tool to a second tangible object:
    wherein the second tangible object is held in a user's hand;
    wherein the virtual tool has location coordinates in physical space;
    wherein a change in the second tangible object's position causes a corresponding change in the virtual tool's position; and
    wherein a change in the second tangible object's orientation causes a corresponding change in the virtual tool's orientation;
  tracking the first tangible object's position and orientation and the second tangible object's position and orientation;
  determining a change in the virtual object's position and orientation, which corresponds to a change in the first tangible object's position and orientation;
  determining a change in the virtual tool's position and orientation, which correspond to a change in the second tangible object's position and orientation;
  causing the virtual object to be manipulated by the virtual tool:
    wherein the manipulation occurs in response to placement of the virtual tool into the virtual object; and
    wherein the manipulation comprises an alteration of the virtual object's three-dimensional structure;
  assigning a virtual task to the user, in which the user manipulates the virtual object using the virtual tool to perform the assigned virtual task, wherein assigning the virtual task to the user comprises assigning a medical procedure; and
  displaying the manipulated virtual object to the user wearing an extended reality head display unit.

16. The apparatus of claim 15 further comprising instructions for:
assigning a set of coordinates on the virtual object designated as a spot; and
performing a programmed response when the spot is touched by the virtual tool.

17. The apparatus of claim 16 wherein the programmed response is an information box.

18. The apparatus of claim 15 wherein the virtual tool comprises a grabbing tool.

19. The apparatus of claim 15 wherein the virtual tool comprises a pointing tool.

20. The apparatus of claim 15 wherein the virtual tool comprises a cutting tool.

21. The apparatus of claim 15 wherein the virtual tool comprises a writing tool.

22. The apparatus of claim 15 comprising an eye tracking system that detects a location in the virtual object upon which the user's eyes are focused and an image generator that provides an indication of the location in the virtual object upon which the user's eyes are focused to a second user who is wearing a second extended reality head display unit and looking at the virtual object.

23. The apparatus of claim 15 comprising an additional task selected from the group consisting of: treating a stroke; treating an aneurysm; emplacing a virtual stent; performing a chemoembolization; and conducting a lung biopsy.

24. The apparatus of claim 15 comprising a processor that calculates a performance score for the virtual task based on manipulation of the item virtual object.

25. The apparatus of claim 15 comprising a processor that calculates a performance score for the virtual task based on correct identification of medical terminology for differing parts of anatomy and associated bodily functions.

26. The apparatus of claim 15 comprising a processor that calculates a performance score for the virtual task based on accuracy and completeness of a diagnosis.

27. The apparatus of claim 15 comprising a processor that calculates a performance score for the virtual task based on accuracy and time to complete a surgical operation.

28. The apparatus of claim 15 comprising a processor that calculates a performance score for the virtual task based on accuracy and time to complete an interventional operation.

* * * * *